(12) United States Patent
Whitman et al.

(10) Patent No.: US 8,229,549 B2
(45) Date of Patent: Jul. 24, 2012

(54) SURGICAL IMAGING DEVICE

(75) Inventors: Michael P. Whitman, New Hope, PA (US); Donald Malinouskas, Monroe, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1412 days.

(21) Appl. No.: 10/888,285

(22) Filed: Jul. 9, 2004

(65) Prior Publication Data

US 2006/0020213 A1  Jan. 26, 2006

(51) Int. Cl.
*A61B 6/00* (2006.01)

(52) U.S. Cl. ......... 600/478; 600/407; 600/425; 600/476

(58) Field of Classification Search .................. 600/476, 600/478, 160, 178
See application file for complete search history.

(56) References Cited

U.S. PATENT DOCUMENTS

| | | |
|---|---|---|
| 3,256,875 A | 6/1966 | Tsepelev et al. |
| 3,858,577 A | 1/1975 | Bass et al. |
| 3,859,986 A | 1/1975 | Okada et al. |
| 4,027,510 A | 6/1977 | Hiltebrandt |
| 4,085,756 A | 4/1978 | Weaver |
| 4,198,960 A | 4/1980 | Utsugi |
| 4,250,873 A | 2/1981 | Bonnet |
| 4,273,109 A | 6/1981 | Enderby |
| 4,273,111 A | 6/1981 | Tsukaya |
| 4,286,585 A | 9/1981 | Ogawa |
| 4,367,729 A | 1/1983 | Ogiu |
| 4,379,457 A | 4/1983 | Gravener et al. |
| 4,402,311 A | 9/1983 | Hattori |
| 4,445,892 A | 5/1984 | Hussein et al. |
| 4,448,188 A | 5/1984 | Loeb |
| 4,494,549 A | 1/1985 | Namba et al. |

(Continued)

FOREIGN PATENT DOCUMENTS

DE  42 13 426  10/1992

(Continued)

OTHER PUBLICATIONS

New York Magazine, Jun. 10, 2002 The Best Doctors in New York, p. 80.

(Continued)

*Primary Examiner* — Tse Chen
*Assistant Examiner* — Baisakhi Roy

(57) ABSTRACT

A surgical imaging device includes at least one light source for illuminating an object, at least two image sensors configured to generate image data corresponding to the object in the form of an image frame, and a video processor configured to receive from each image sensor the image data corresponding to the image frames and to process the image data so as to generate a composite image. The video processor may be configured to normalize, stabilize, orient and/or stitch the image data received from each image sensor so as to generate the composite image. Preferably, the video processor stitches the image data received from each image sensor by processing a portion of image data received from one image sensor that overlaps with a portion of image data received from another image sensor. Alternatively, the surgical device may be, e.g., a circular stapler, that includes a first part, e.g., a DLU portion, having an image sensor a second part, e.g., an anvil portion, that is moveable relative to the first part. The second part includes an arrangement, e.g., a bore extending therethrough, for conveying the image to the image sensor. The arrangement enables the image to be received by the image sensor without removing the surgical device from the surgical site.

40 Claims, 32 Drawing Sheets

U.S. PATENT DOCUMENTS

| | | |
|---|---|---|
| 4,499,895 A | 2/1985 | Takayama |
| 4,559,928 A | 12/1985 | Takayama |
| 4,593,679 A | 6/1986 | Collins |
| 4,672,961 A | 6/1987 | Davies |
| 4,674,515 A | 6/1987 | Andou et al. |
| 4,732,156 A | 3/1988 | Nakamura |
| 4,742,815 A | 5/1988 | Ninan et al. |
| 4,756,309 A | 7/1988 | Sachse et al. |
| 4,760,840 A | 8/1988 | Fournier, Jr. et al. |
| 4,815,469 A | 3/1989 | Cohen et al. |
| 4,819,632 A | 4/1989 | Davies |
| 4,880,015 A | 11/1989 | Nierman |
| 4,890,602 A | 1/1990 | Hake |
| 4,893,613 A | 1/1990 | Hake |
| 4,907,588 A | 3/1990 | Burston |
| 4,907,973 A | 3/1990 | Hon |
| 4,928,699 A | 5/1990 | Sasai |
| 4,930,494 A | 6/1990 | Takehana et al. |
| 4,941,454 A | 7/1990 | Wood et al. |
| 4,944,443 A | 7/1990 | Oddsen et al. |
| 4,955,882 A | 9/1990 | Hakky |
| 4,976,710 A | 12/1990 | Mackin |
| 4,982,726 A | 1/1991 | Taira |
| 4,994,060 A | 2/1991 | Rink et al. |
| 5,133,713 A | 7/1992 | Huang et al. |
| 5,134,281 A | 7/1992 | Bryenton et al. |
| 5,186,714 A | 2/1993 | Boudreault et al. |
| 5,197,649 A | 3/1993 | Bessler et al. |
| 5,201,325 A | 4/1993 | McEwen et al. |
| 5,201,730 A | 4/1993 | Easley et al. |
| 5,217,003 A | 6/1993 | Wilk |
| 5,251,613 A | 10/1993 | Adair |
| 5,258,008 A | 11/1993 | Wilk |
| 5,261,404 A * | 11/1993 | Mick et al. ................ 600/425 |
| 5,305,121 A | 4/1994 | Moll |
| 5,306,234 A | 4/1994 | Johnson |
| 5,322,055 A | 6/1994 | Davison et al. |
| 5,330,486 A | 7/1994 | Wilk |
| 5,333,772 A | 8/1994 | Rothfuss et al. |
| 5,354,266 A | 10/1994 | Snoke |
| 5,368,015 A | 11/1994 | Wilk |
| 5,383,880 A | 1/1995 | Hooven |
| 5,395,030 A | 3/1995 | Kuramoto et al. |
| 5,411,508 A | 5/1995 | Bessler et al. |
| 5,437,636 A | 8/1995 | Snoke et al. |
| 5,441,507 A | 8/1995 | Wilk |
| 5,460,182 A | 10/1995 | Goodman et al. |
| 5,496,269 A | 3/1996 | Snoke |
| 5,531,687 A | 7/1996 | Snoke et al. |
| 5,540,711 A | 7/1996 | Kieturakis et al. |
| 5,603,688 A | 2/1997 | Upsher |
| 5,604,531 A | 2/1997 | Iddan et al. |
| 5,609,560 A | 3/1997 | Ichikawa et al. |
| 5,630,782 A | 5/1997 | Adair |
| 5,653,677 A | 8/1997 | Okada et al. |
| 5,662,680 A | 9/1997 | Desai |
| 5,667,473 A | 9/1997 | Finn et al. |
| 5,667,478 A | 9/1997 | McFarcin et al. |
| 5,667,517 A | 9/1997 | Hooven |
| 5,797,835 A | 8/1998 | Green |
| 5,797,944 A | 8/1998 | Nobles et al. |
| 5,815,640 A | 9/1998 | Wang et al. |
| 5,820,545 A * | 10/1998 | Arbter et al. ................ 600/117 |
| 5,855,583 A | 1/1999 | Wang et al. |
| 5,857,996 A | 1/1999 | Snoke |
| 5,865,728 A | 2/1999 | Moll et al. |
| 5,868,760 A | 2/1999 | McGuckin, Jr. |
| 5,878,193 A | 3/1999 | Wang et al. |
| 5,882,331 A | 3/1999 | Sasaki |
| 5,907,664 A | 5/1999 | Wang et al. |
| 5,920,390 A | 7/1999 | Farahi et al. |
| 5,935,143 A | 8/1999 | Hood |
| 5,941,818 A | 8/1999 | Hori et al. |
| 5,954,634 A | 9/1999 | Igarashi |
| 5,954,642 A | 9/1999 | Johnson et al. |
| 5,968,060 A | 10/1999 | Kellogg |
| 5,989,184 A | 11/1999 | Blair |
| 5,989,274 A | 11/1999 | Davison et al. |
| 5,993,378 A | 11/1999 | Lemelson |
| 5,995,645 A | 11/1999 | Soenksen et al. |
| 6,015,969 A | 1/2000 | Nathel et al. |
| 6,027,515 A | 2/2000 | Cimino |
| 6,056,735 A | 5/2000 | Okada et al. |
| 6,063,095 A | 5/2000 | Wang et al. |
| 6,066,090 A | 5/2000 | Yoon |
| 6,068,627 A | 5/2000 | Orszulak et al. |
| 6,068,647 A | 5/2000 | Witt et al. |
| 6,069,689 A | 5/2000 | Zeng et al. |
| 6,074,402 A | 6/2000 | Peifer et al. |
| 6,077,285 A | 6/2000 | Boukhny |
| 6,083,191 A | 7/2000 | Rose |
| 6,099,466 A | 8/2000 | Sano et al. |
| 6,099,537 A | 8/2000 | Sugai et al. |
| 6,117,152 A | 9/2000 | Huitema |
| 6,124,597 A | 9/2000 | Shehada et al. |
| 6,126,591 A | 10/2000 | McGarry et al. |
| 6,134,003 A | 10/2000 | Tearney et al. |
| 6,139,561 A | 10/2000 | Shibata et al. |
| 6,142,930 A | 11/2000 | Ito et al. |
| 6,159,225 A | 12/2000 | Makower |
| 6,163,378 A | 12/2000 | Khoury |
| 6,208,749 B1 | 3/2001 | Gutkowicz-Krusin et al. |
| 6,208,887 B1 | 3/2001 | Clarke |
| 6,211,904 B1 | 4/2001 | Adair et al. |
| 6,215,550 B1 | 4/2001 | Baer et al. |
| 6,216,025 B1 * | 4/2001 | Kruger ................ 600/407 |
| 6,224,227 B1 | 5/2001 | Klootz |
| 6,236,502 B1 | 5/2001 | Kitajima |
| 6,238,386 B1 | 5/2001 | Muller et al. |
| 6,240,305 B1 | 5/2001 | Tsuchiya |
| 6,244,809 B1 | 6/2001 | Wang et al. |
| 6,245,058 B1 | 6/2001 | Suzuki |
| 6,251,101 B1 | 6/2001 | Glockler |
| 6,261,226 B1 * | 7/2001 | McKenna et al. ................ 600/109 |
| 6,263,227 B1 | 7/2001 | Boggett et al. |
| 6,319,199 B1 | 11/2001 | Sheehan et al. |
| 6,331,181 B1 | 12/2001 | Tierney et al. |
| 6,352,503 B1 | 3/2002 | Matsui et al. |
| 6,364,888 B1 | 4/2002 | Niemeyer et al. |
| 6,398,726 B1 | 6/2002 | Ramans et al. |
| 6,442,432 B2 | 8/2002 | Lee |
| 6,443,973 B1 | 9/2002 | Whitman |
| 6,459,822 B1 | 10/2002 | Hathaway et al. |
| 6,471,637 B1 | 10/2002 | Green et al. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,533,157 B1 | 3/2003 | Whitman |
| 2001/0001812 A1 | 5/2001 | Valley et al. |
| 2001/0016725 A1 | 8/2001 | Valley et al. |
| 2001/0031975 A1 | 10/2001 | Whitman et al. |
| 2002/0026094 A1 | 2/2002 | Roth |
| 2002/0032451 A1 | 3/2002 | Tierney et al. |
| 2002/0032452 A1 | 3/2002 | Tierney et al. |
| 2002/0042620 A1 | 4/2002 | Julian et al. |
| 2002/0049454 A1 | 4/2002 | Whitman et al. |
| 2002/0055795 A1 | 5/2002 | Niemeyer et al. |
| 2002/0092533 A1 | 7/2002 | Boyd et al. |
| 2002/0159529 A1 | 10/2002 | Wang et al. |
| 2002/0161280 A1 | 10/2002 | Chatenever et al. |
| 2002/0161282 A1 | 10/2002 | Fulghum |
| 2002/0165444 A1 | 11/2002 | Whitman |
| 2003/0135092 A1 * | 7/2003 | Cline et al. ................ 600/160 |
| 2003/0176794 A1 * | 9/2003 | Whitman ................ 600/476 |
| 2006/0052708 A1 * | 3/2006 | Iddan et al. ................ 600/476 |

FOREIGN PATENT DOCUMENTS

| | | |
|---|---|---|
| EP | 0 667 115 | 8/1995 |
| GB | 2128881 | 5/1984 |
| GB | 2 291 980 | 2/1996 |
| GB | 2291980 | 2/1996 |
| JP | 59 223 079 | 12/1984 |
| WO | WO 82/03545 | 10/1982 |
| WO | WO 83/00992 | 3/1983 |
| WO | WO 92/16141 | 10/1992 |
| WO | WO 98/32380 | 7/1998 |

| | | |
|---|---|---|
| WO | WO 99/30610 | 6/1999 |
| WO | WO 99/32028 | 7/1999 |
| WO | WO 00/22975 | 4/2000 |
| WO | WO 00/76391 | 12/2000 |
| WO | WO 01/10291 | 2/2001 |
| WO | WO 01/35813 | 5/2001 |
| WO | WO 01/56460 A1 | 8/2001 |
| WO | WO 01/62163 | 8/2001 |
| WO | WO 02/055126 | 7/2002 |
| WO | WO 03/077769 | 9/2003 |

OTHER PUBLICATIONS

"Manometric Findings in Dysphagia Secondary to Left Atrial Dilatation Digestive Diseases and Sciences", vol. 36, May 1991, M. Cappell.

"Case Report: Late Pulmonary Embolization . . . ", Apr. 1985, E.D. Mayer et al.

"Fiberoptic examination of the inferior vena cava . . . ", Thorac. Cardiovascular Surgeon, 33, Jun. 1990, A. R. Hartman.

"Media Stinoscope: Another Use." Journal of Cardio Surgery, 27, Mar. 1986, P. R. Behl.

"Special Pacemaker Catheter Techniques: The Transmediastinal Placement of Sensing Electrodes", Apr. 1976, Kleinert et al.

"Endobronchial Resection with the ND-Yag Laser—Two Year Experience in an Australian Unit", Australia/New Zealnd Journal of Medicine, Apr. 1990, R. J. Pierce.

"Cardiovascular Fiberoptic Endoscopy: Development and Clinical Application", Apr. 1980, T. Tanabe et al.

European Search Report for corresponding EP05769530 date of mailing is Sep. 24, 2009 (3 pages).

European Search Report for EP 11001302 application, date of completion, Apr. 27, 2011.

European Search Report for corresponding EP11001301 date of mailing is Aug. 9, 2011 (3 pages).

* cited by examiner

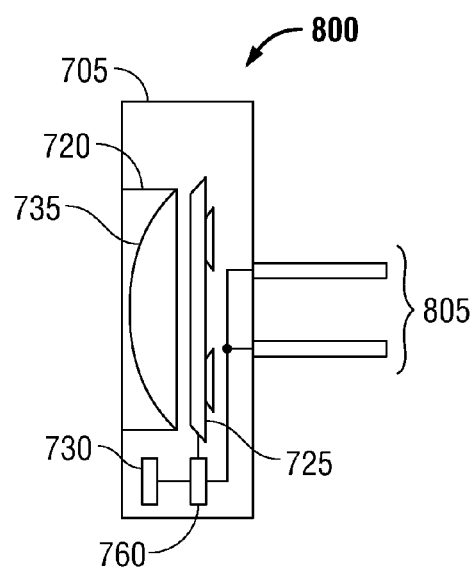
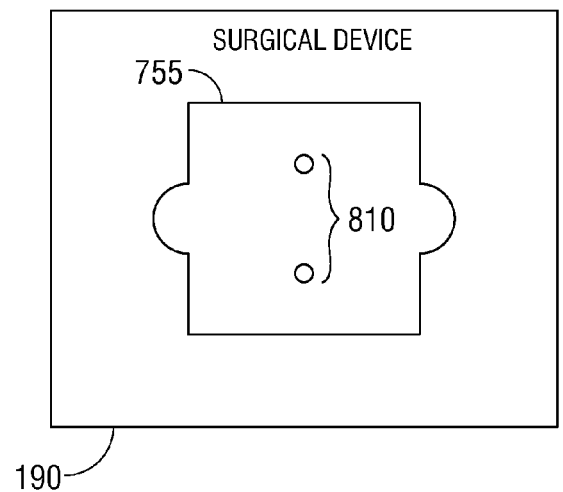
FIG. 8A  FIG. 8B
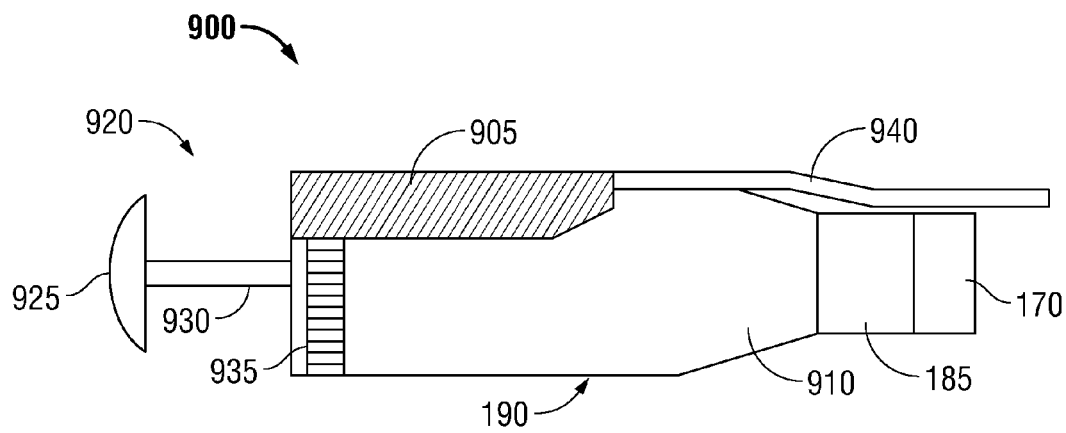
FIG. 9

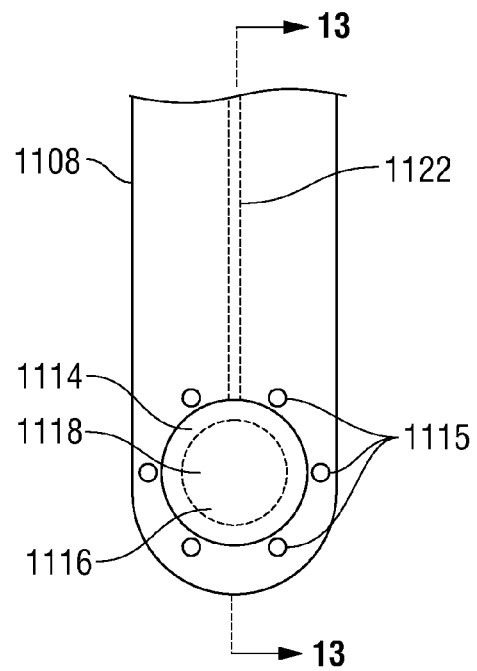
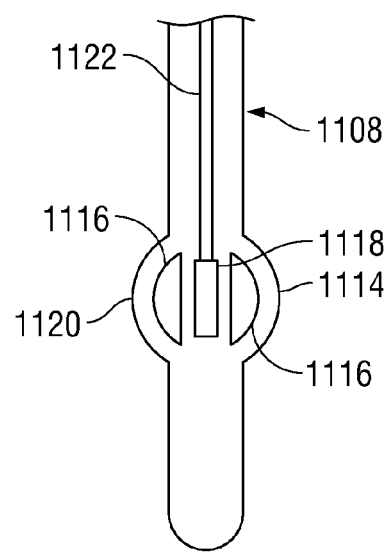
FIG. 12  FIG. 13
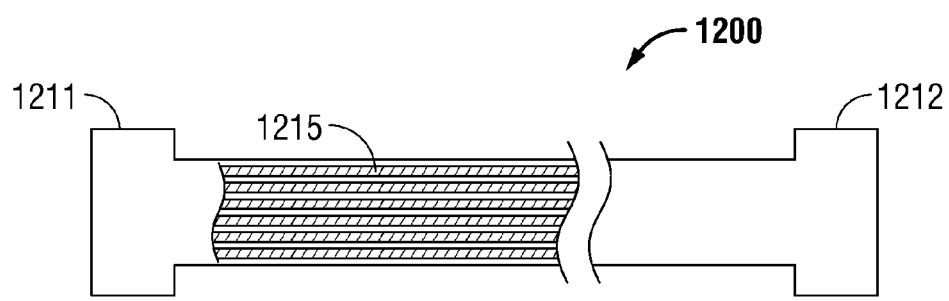
FIG. 14

ALIGNMENT
VECTOR

SURGICAL IMAGING DEVICE

CROSS-REFERENCE TO RELATED APPLICATIONS

This application relates to U.S. Patent Application Ser. No. 60/285,193, filed on Apr. 20, 2001, U.S. Patent Application Ser. No. 60/300,107, filed on Jun. 22, 2001, U.S. Patent Application Ser. No. 60/344,648, filed on Dec. 31, 2001, and U.S. Patent Application Ser. No. 60/352,726, filed on Jan. 30, 2002, each of which is expressly incorporated herein by reference in its entirety.

This application also relates to U.S. patent application Ser. No. 09/324,452, filed on Jun. 2, 1999 and issued as U.S. Pat. No. 6,443,973, U.S. application Ser. No. 09/723,715, filed on Nov. 28, 2000, U.S. application Ser. No. 09/324,451, filed on Jun. 2, 1999 and issued as U.S. Pat. No. 6,315,184, U.S. application Ser. No. 09/351,534, filed on Jul. 12, 1999 and issued as U.S. Pat. No. 6,264,087, U.S. application Ser. No. 09/510,923, filed on Feb. 22, 2000 and issued as U.S. Pat. No. 6,517,565, U.S. application Ser. No. 09/510,927, filed on Feb. 22, 2000, U.S. application Ser. No. 09/510,932, filed on Feb. 22, 2000 and issued as U.S. Pat. No. 6,491,201, U.S. application Ser. No. 09/836,781, filed on Apr. 17, 2001, U.S. patent application Ser. No. 09/887,789, filed on Jul. 22, 2001, U.S. application Ser. No. 10/127,310, filed on Apr. 22, 2002, and U.S. application Ser. No. 10/355,906, filed on Jan. 30, 2003, each of which is expressly incorporated herein in its entirety by reference.

FIELD OF THE INVENTION

The present invention relates to a surgical imaging device, and in particular to a surgical imaging device that is configured to provide image data of a surgical site.

BACKGROUND INFORMATION

It is typically important during a surgical procedure that a surgeon be able to view a surgical site so as to ensure that the surgical procedure is being performed correctly. However, there are many types of surgical procedures in which the surgeon is not able to see the surgical site. For instance, laparoscopic or endoscopic surgical procedures, in which a surgeon accesses a surgical site through very small incisions, prevent the surgeon from viewing the surgical site.

One method for performing surgical procedures of this type is to employ surgical devices that include arrangements for indicating the position of components of the surgical devices while in use. For instance, a surgical device for such a surgical procedure may include a remote status indicator that provides an indication of the position of a component of the surgical device. By knowing the position of the components of the surgical device, the surgeon may determine if the surgical device is being operated correctly during the surgical procedure. A remote status indicator may provide this information to the user via a LCD indicator which is coupled to an electromagnetic sensor. For example, a surgical instrument may include an anvil portion and a staple, blade and reservoir (SBR) portion. The surgical instrument may detachably couple to an electromechanical driver device via a shaft. The surgeon advances the shaft and the SBR portion of the attachment into the body cavity. The base of the anvil portion and the outer edge of the SBR housing may include an electromagnetic sensor which is coupled to the LCD indicator of the handle, thereby permitting the surgeon to know the position of the anvil and the SBR during the surgical procedure.

Another method for performing surgical procedures of this type is to employ a video camera or the like. For instance, various types of cameras may be configured to be inserted through an incision in a patient and into a surgical site. Such cameras provide video data of the surgical site during a surgical procedure, thereby allowing the surgeon to see the surgical procedure taking place in real time. However, because of the small size of the incision, once one of these cameras is inserted through an incision and into a surgical site, it may be difficult to maneuver. In addition, these cameras provide only a single view of the surgical site. If the surgeon needs to change the view of the surgical site, e.g., to examine the surgical site from a different angle, the surgeon typically is required to remove the camera from the first incision, to make another incision in the patient, and to reinsert the camera into the second incision.

For example, surgeons utilize various surgical instruments for inter-abdominal, inter-thoracic and other similar surgical procedures. Typically, surgeons desire to perform these procedures using minimally invasive surgical techniques. In an endoscopic procedure, for example, a small incision is made, e.g., in a patient's abdomen, etc., and an endoscope is inserted therein in order to view the body cavity in which the surgeon intends to perform the surgery. These types of surgical procedures typically require the use of an endoscope which enables the surgeon to obtain a view of the body cavity and the manipulation of a surgical device used during the surgery. Many times, the surgeon inserts both the endoscope and the surgical device either through the same incision or may use separate incisions for each device. In most surgical procedures using an endoscope, a member of the surgical team may continuously monitor the positioning of the endoscope in order maintain a suitable view of the body cavity and the manipulation of the surgical device.

Another problem that is experienced by conventional surgical imaging systems is that they do not provide an image that is adequately stable. For instance, U.S. Pat. No. 6,097,423, which is expressly incorporated herein in its entirety by reference, describes that, in conventional surgical imaging systems, movement of a camera typically causes undesired changes in the image that is eventually displayed to and viewed by a user, e.g., surgeon.

Thus, there is a need for an improved surgical imaging device that is configured to provide image data of a surgical site for display to a user.

SUMMARY

In accordance with one example embodiment of the present invention, a surgical imaging unit is provided, including a housing configured to detachably couple to an outer surface of a surgical device, and an image capture arrangement configured to generate image data; the imaging unit may also include a circuit arrangement disposed within the housing and electrically coupled to the image capture arrangement, in which the circuit arrangement is configured to communicate the image data to at least one remote device.

In accordance with another example embodiment of the present invention, a surgical attachment is provided, including a surgical device, and an imaging unit having a housing configured to detachably couple to an outer surface of the surgical device and an image capture arrangement configured to generate image data; the imaging unit may further include a circuit arrangement disposed within the housing and electrically coupled to the image capture arrangement, in which the circuit arrangement is configured to communicate the image data to at least one remote device.

In accordance with another example embodiment of the present invention, a surgical system is provided, including an electromechanical driver device, a surgical device detachably coupled to the electromechanical driver device, and an imaging unit having a housing configured to couple to an outer surface of the surgical device and an image capture arrangement configured to generate image data; the imaging unit may further include a circuit arrangement disposed within the housing and electrically coupled to the image capture arrangement, in which the circuit arrangement is configured to communicate the image data to at least one remote device.

In accordance with another example embodiment of the present invention, a surgical imaging device is provided, wherein the surgical imaging device is configured to be inserted into a surgical site and wherein the surgical imaging device includes a plurality of prongs. Each one of the prongs has an image sensor mounted thereon. The image sensors provide different image data corresponding to the surgical site, thus enabling a surgeon to view a surgical site from several different angles.

The prongs may be moveable between a first position, in which the prongs are substantially parallel to each other, and a second position, in which the prongs are not substantially parallel to each other. In the substantially parallel configuration, e.g., the first position, the prongs are configured to be inserted through an incision into the surgical site. Once inserted through the incision into the surgical site, the prongs may be radially separated from each other by a user rotating control levers that are connected to the prongs by legs.

In addition, the prongs may be bendable between an extended position, in which the prongs are substantially perpendicular to their respective legs, and a retracted position, in which the prongs are not substantially perpendicular to their respective legs. Advantageously, the prongs are configured to bend in conformance with a shape of a cavity that is formed in the surgical site by the actuation of an actuator configured to form such a cavity.

The surgical imaging device may be configured for operation in a wired format, a wireless format, or both. In the wired format, the device may include a body portion having a slot in electrical communication with the image sensors, a video display device configured to display the image data, and a control cable that is configured to the transmit image data from the image sensor to the video display device. In the wired format, the device may also include a power supply coupleable to the control cable for supplying power to the device. In the wireless format, the device may include a body portion having a first antenna and a remote control device having a second antenna, wherein the remote control device is configured to provide a wireless control signal via the second antenna to the device via the first antenna. In addition, in the wireless format, the device may include a video display device having an antenna, wherein the device is configured to generate via the first antenna a wireless signal corresponding to image data from the image sensors, and wherein the video display device is configured to receive the wireless signal and to provide a display corresponding to the image data. In the wireless format, the device may also include a local power supply for providing power to the device.

In accordance with another example embodiment of the present invention, a surgical imaging device is provided, which includes at least one light source for illuminating an object. The surgical imaging device also includes at least two image sensors, each image sensor configured to generate image data corresponding to the object in the form of an image frame. The surgical imaging device further includes a video processor configured to receive from each image sensor the image data corresponding to the image frames and to process the image data so as to generate a composite image. The video processor may be configured to normalize, stabilize and/or orient the image data received from each image sensor. In addition, the video processor may be configured to stitch the image data received from each image sensor so as to generate the composite image. Preferably, the video processor stitches the image data received from each image sensor by processing a portion of image data received from one image sensor that overlaps with a portion of image data received from another image sensor.

In accordance with another example embodiment of the present invention, a surgical device for insertion into a surgical site is provided. The surgical device, e.g., a circular stapler, includes a first part, e.g., a DLU portion, that includes an image sensor configured to receive an image. The surgical device includes a second part, e.g., an anvil portion, that is moveable relative to the first part. The second part includes an arrangement, e.g., a bore extending therethrough, for conveying the image to the image sensor. The arrangement enables the image to be received by the image sensor without removing the surgical device from the surgical site. The surgical device may also include a video processor in communication with the image sensor and configured to provide image data corresponding to the image to a display unit. In one embodiment, the image sensor and the arrangement are automatically aligned, for instance by the image and the arrangement being centrally disposed, e.g., "on-axis", within the first and second parts, respectively. In another embodiment, the image and the arrangement are non-centrally disposed, e.g., "off-axis", within the first and second parts, respectively, and the image sensor and the arrangement are rotationally aligned via alignment mechanisms.

BRIEF DESCRIPTION OF THE DRAWINGS

FIG. 4b is a side view of the image capture arrangement illustrated in FIG. 4a.

FIG. 8a illustrates another exemplary imaging pod, according to one embodiment of the present invention.

FIG. 8*b* illustrates an exemplary receptacle of a surgical device configured to receive the imaging pod illustrated in FIG. 8*a*.

FIG. 9 illustrates another exemplary surgical attachment, according to one embodiment of the present invention.

FIG. 12 illustrates a prong having a camera, according to one embodiment of the present invention.

FIG. 13 is a cross-sectional view of the prong shown in FIG. 12, taken along the lines A-A.

FIG. 14 illustrates a control cable, according to one embodiment of the present invention.

FIG. 25(*b*) illustrates a current image frame according to one example embodiment of the present invention.

FIG. 25(*c*) is a flow chart that illustrates, according to one example embodiment of the present invention, a frame stabilization procedure that may be employed by the processor.

FIG. 26(*b*) illustrates first image regions translating to second image regions as a result of alignment vectoring.

FIG. 26(*c*) is a flow chart that illustrates, according to one example embodiment of the present invention, a frame stitching procedure that may be employed by the processor.

FIG. 29(*b*) is a side view of the image capturing device, according to one embodiment of the present invention.

DETAILED DESCRIPTION

Figure 1:
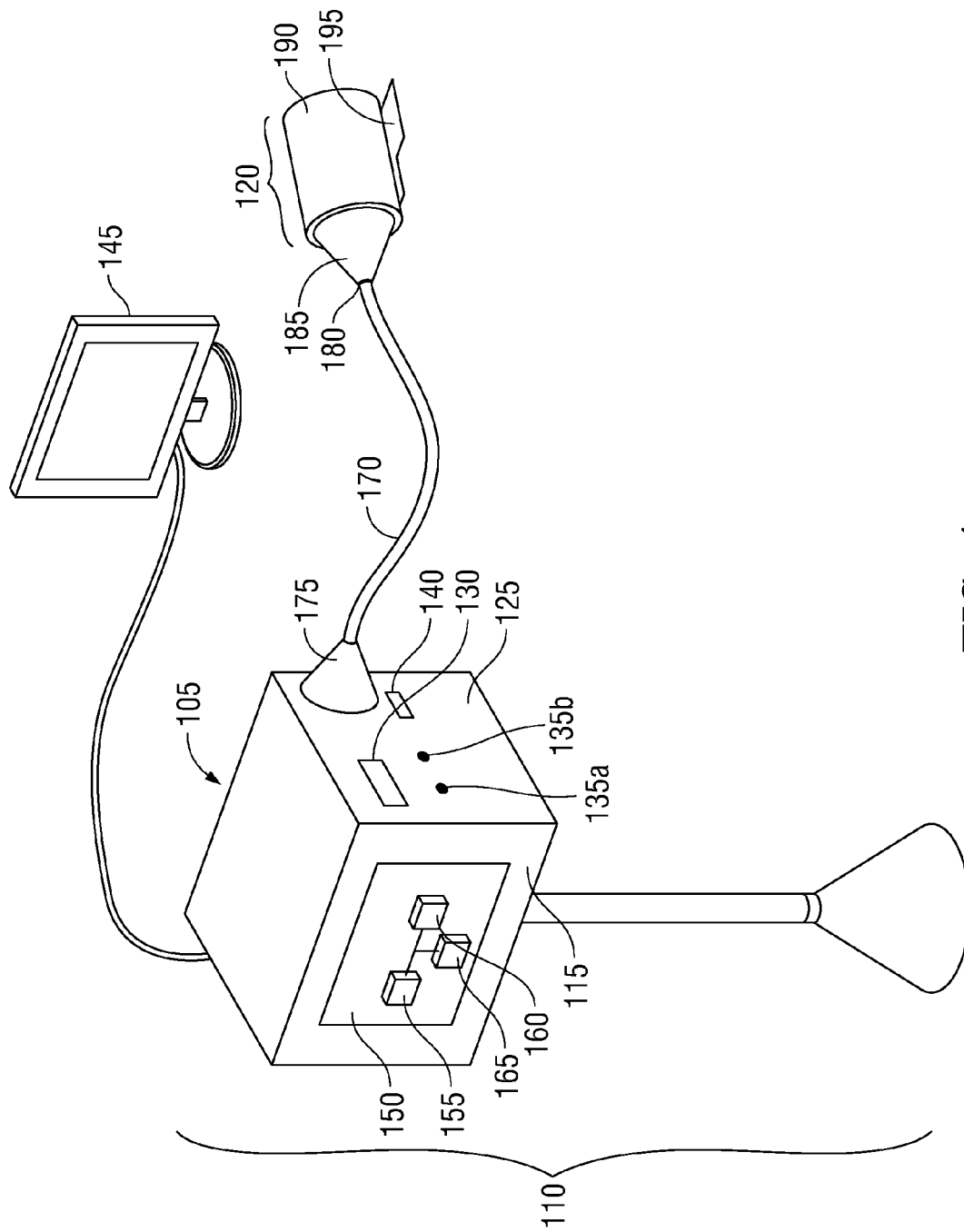
FIG. 1 illustrates an exemplary surgical system, according to one embodiment of the present invention.

Referring now to FIG. 1, there is seen a surgical system 100. Surgical system 100 includes an electromechanical driver device 110 detachably coupled to a surgical attachment 120. Such an electro-mechanical driver device is described in, for example, U.S. patent application Ser. No. 09/723,715, entitled "Electro-Mechanical Surgical Device," filed on Nov. 28, 2000, U.S. patent application Ser. No. 09/836,781, entitled "Electro-Mechanical Surgical Device, filed on Apr. 17, 2001, and U.S. patent application Ser. No. 09/887,789, entitled "Electro-Mechanical Surgical Device," filed on Jun. 22, 2001, each of which is expressly incorporated herein in its entirety by reference. Electro-mechanical driver device 110 may include, for example, a remote power console (RPC) 105, which includes a housing 115 having a front panel 125. Mounted on front panel 125 are a display device 130 and indicators 135*a*, 135*b*. A connection slot 140 is also provided on front panel 125. Electro-mechanical driver device 110 may also include a video display 145, e.g., a television monitor, computer monitor, CRT or other viewing device, attached to the RPC 105. Video display 145 may receive, for example, image signals (e.g., video signals) from an imaging device 195. The electromechanical driver device 110 may also include a reception system 150 having a receiver or transceiver 155 and circuitry 160 operable to convert signals received from the imaging device 195 into a form suitable for display on video display 145. The reception system 150 may also include a memory device 165 for buffering and/or storing processed image data received from the imaging device 195.

A flexible shaft 170 may extend from housing 115 and may be detachably secured thereto via a first coupling 175. The distal end 180 of flexible shaft 170 may include a second coupling 185 adapted to detachably secure the surgical attachment 120 to the distal end 180 of the flexible shaft 170.

Disposed within the interior channel of the flexible shaft 170, and extending along the length thereof, may be rotatable shafts, steering cables, one or more data transfer cables and power transfer leads, all of which terminate at the second coupling 185 at the distal end 180 of the flexible shaft 170. The electro-mechanical driver device 110 may include a motor system (not shown), which includes one or more motors configured to rotate the drive shafts and to apply tension or otherwise drive the steering cables to thereby steer the distal end 180 of the flexible shaft 170.

Figure 2A:
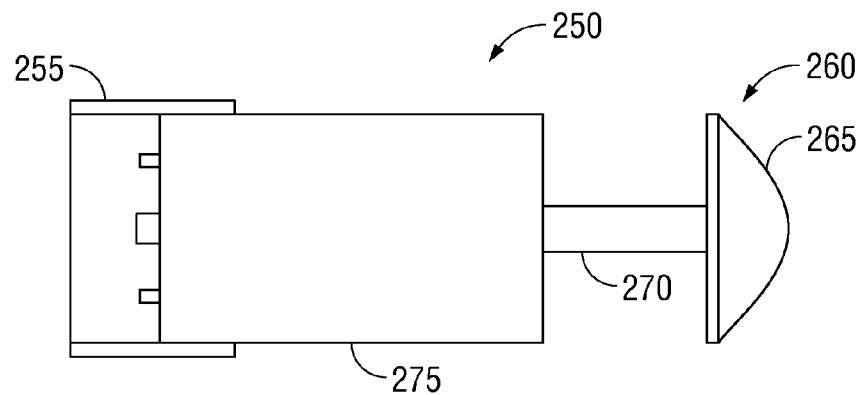
FIG. 2a illustrates a circular surgical stapler attachment, according to one embodiment of the present invention.

Various types of surgical devices 190 may be attached to the distal end 180 of the flexible shaft 170, such as a circular surgical stapler attachment (CSS) 250, shown schematically in FIG. 2*a*. Referring to FIG. 2(*a*), the CSS 250 includes a coupling 255 adapted by size and configuration to cooperate with the second coupling 185 of flexible shaft 170 to detachably couple the CSS 250 thereto. CSS 250 includes an anvil portion 260 having an anvil 265 mounted on the distal end of an anvil stem 270. The anvil stem 270 is extended and retracted by the operation of an anvil drive shaft (not shown), which is rotatably secured within the body portion 275 of the CSS 250. CSS 250 further includes a staple driver/cutter mechanism (not shown) within the body portion 275. In operation, the extension and retraction of the anvil 265 and the staple driver/cutter may be effected by the operation of motors within the electro-mechanical driver device 110.

Movement and control of the anvil 265 and staple driver/cutter may be performed through the use of a remote control unit (not shown). The position and location of the anvil 265 and staple driver/cutter are indicated by signals transmitted to the electromechanical driver device 110 and displayed for the user on the display device 130 and indicators 135a, 135b. CSS 250 further includes a data connector (not shown) adapted to electrically and communicatively couple to second coupling 185.

Figure 2B:
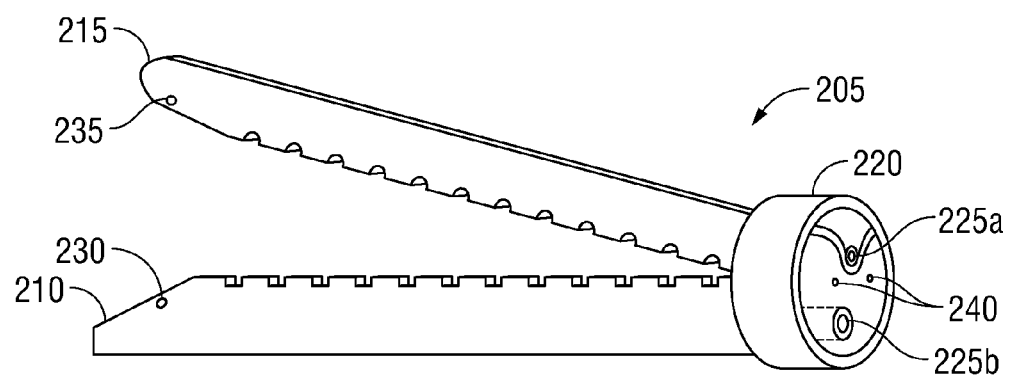
FIG. 2b illustrates a linear surgical stapler, according to one embodiment of the present invention.

Referring now to FIG. 2b, there is seen another exemplary surgical device 190 as a linear surgical stapler 205, such as described in detail in U.S. Pat. No. 6,443,973 which is expressly incorporated herein by reference in its entirety. The linear surgical stapler 205 may include a separating jaw system comprising a lower jaw 210, an upper jaw 215 and a coupling 220. Coupling 220 may include two hexagonal shaped sockets 225a, 225b into which second coupling 185 of flexible shaft 170 is detachably received. At the distal tip of the upper jaw 215 and lower jaw 210 may be situated two opposing magnetic sensors 230, 235, each coupled to a circuit component (not shown) which connects to the electromechanical driver device 110 via flexible shaft 170. When the lower and upper jaws 210, 215 come together, the circuit is closed and indicators 135a, 135b of the electromechanical driver device 110 provide a signal indicating that the stapling mechanism (not shown) of lower jaw 210 may be safely fired. The linear surgical stapler 205 may also include a shaft and driver component configured to close jaws 210, 215 onto tissue and to drive staples into the tissue for closure. The magnetic sensors 230, 235 and circuitry associated with the linear surgical stapler attachment 205 may also, for example, provide a user with an indication when a section of tissue has been fully clamped.

The linear surgical stapler 205 may also include electrodes (not shown).

The electrodes may receive RF energy through contacts 240 and enable the coagulation and/or anastomosing of tissue. The linear surgical stapler attachment 205 may incorporate various electrode and/or stapling configurations, as described in U.S. Patent Application Ser. No. 60/285,113, entitled "A Surgical Linear Clamping, Stapling, and Cutting Device", filed on Apr. 20, 2001 and U.S. Patent Application Ser. No. 60/289,370, entitled "Bipolar Surgical Device" filed on May 8, 2001, each of which is expressly incorporated herein by reference in its entirety.

Although FIG. 2a, 2b show only a circular surgical stapler and a linear surgical stapler, respectively, it should be appreciated that the surgical device 190 may include other arrangements. For example, surgical device 190 may include a trocar device, as described in U.S. patent application Ser. No. 10/098,217, filed on Mar. 14, 2002, which is expressly incorporated herein by reference.

Figure 3A:
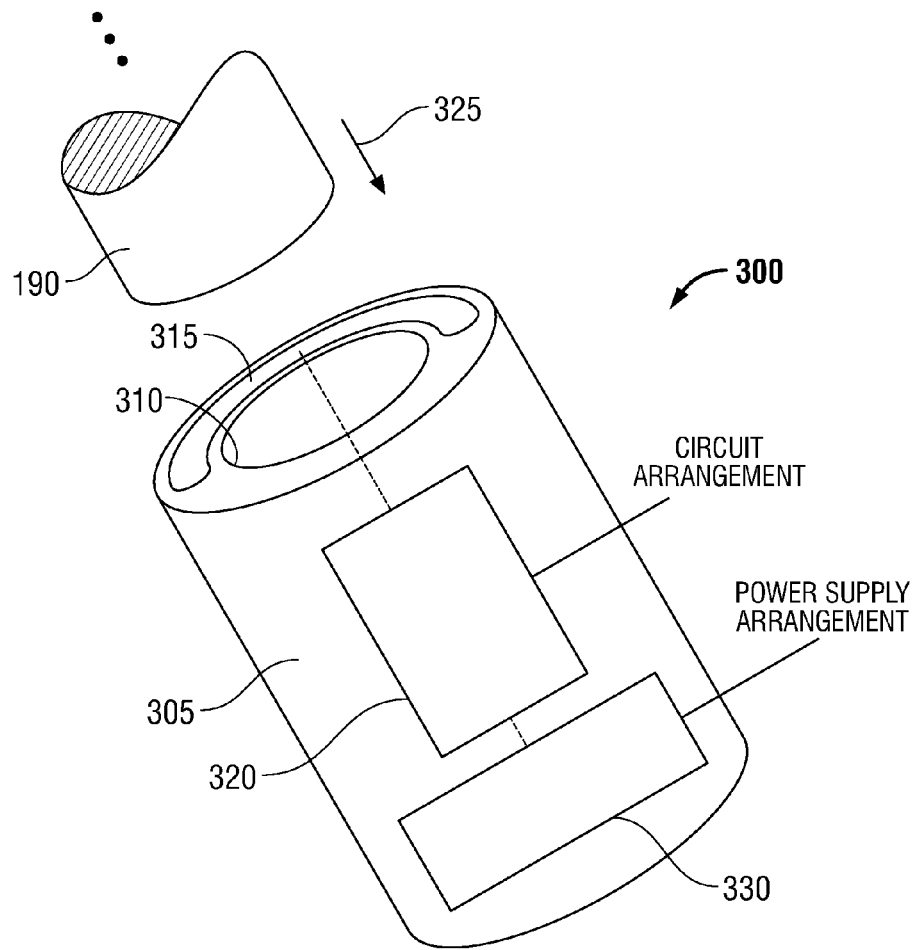
FIG. 3a illustrates a first exemplary imaging device configured to couple to a surgical device, according to one embodiment of the present invention.

Referring now to FIG. 3a, there is seen a first exemplary imaging device 300 configured to couple to the surgical device 190, for example, a linear stapler or a circular surgical stapler. Imaging device 300 includes a housing 305 having a bore 310, an image capture arrangement 315 (e.g., a camera), a circuit arrangement 320 electrically coupled to the image capture arrangement 315, and a power supply arrangement 330 for supplying power to the imaging device 300.

Figure 3B:
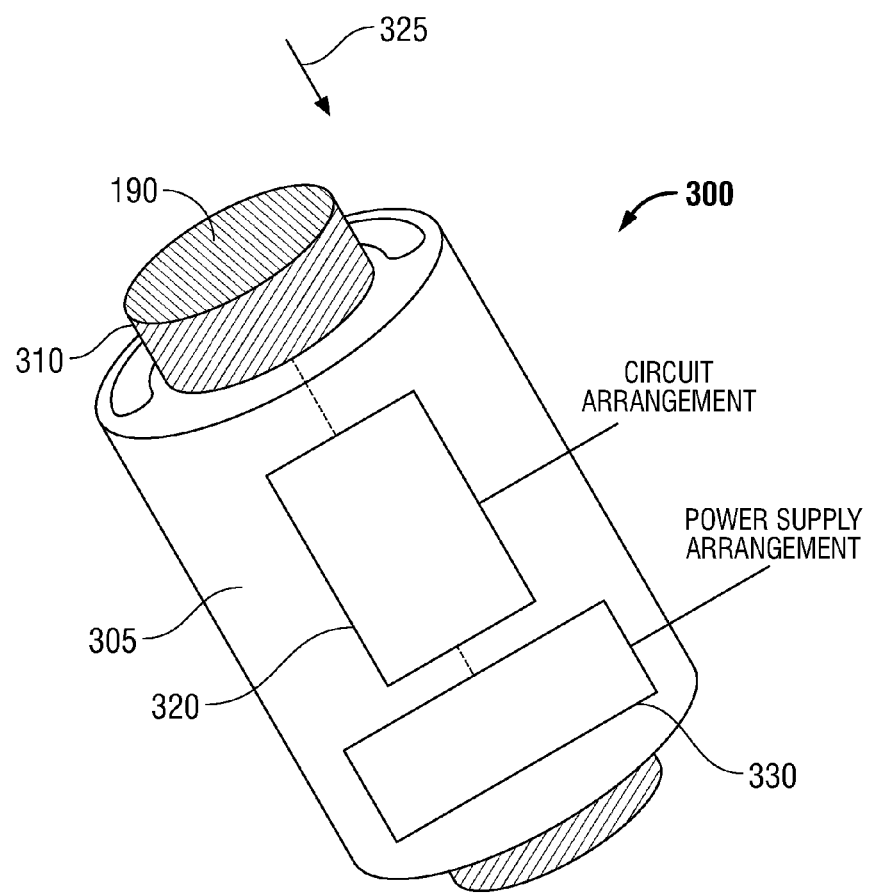
FIG. 3b illustrates the imaging device of FIG. 3a, with the surgical device coupled to the imaging device.

The imaging device 300 is suitably configured to slidably receive the surgical device 190 within bore 310. For this purpose, the surgical device 190 may be inserted into the bore 310 in a first direction 325, as shown in FIG. 3b. Once inserted, a coupling mechanism (not shown) may hold the surgical device 190 in place within the bore 310.

It should be appreciated that the coupling mechanism may include any arrangement suitable for detachably holding the surgical device 190 in place within the bore 310, such as, clamps, nuts, bolts, clasps, straps, a frictional-fit arrangement, a snap-fit arrangement, etc. Thus, the imaging device 300 may be detachably coupled to or mounted on an outer surface of the surgical device 190. Configured in this manner, after the imaging device 300 is used with the surgical device 190, the imaging device 300 may be removed from the surgical device 190 and reused on another surgical device. This may be particularly advantageous if, for example, the surgical devices are disposable with and it is desired to reuse the imaging device 300 several times. Of course, in an alternate embodiment, the surgical device 190 may be permanently coupled to the imaging device 300.

Although FIGS. 3a, 3b show bore 310 having a cylindrical shape, it should be appreciated that bore 310 may be suitably shaped and configured to provide compatible attachment to other surgical devices, which may or may not be cylindrical in shape.

Figure 4A:
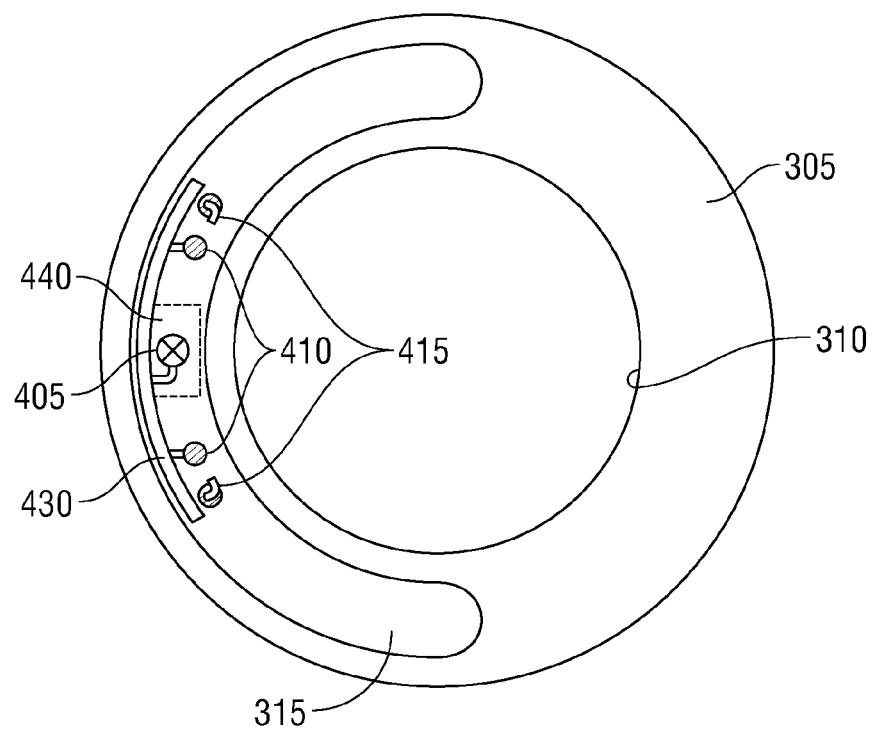
FIG. 4a illustrates an exemplary image capture arrangement, according to one embodiment of the present invention.

Referring now to FIG. 4a, there is seen a frontal view of the image capture arrangement 315 illustrated in FIGS. 3a, 3b showing further detail. As shown in FIG. 4a, the image capture arrangement 315 includes a lens 405, a light source 410 for illuminating an object to be imaged (e.g., fiber optic light sources, light bulbs, LEDs, etc.), an image sensor 440 (e.g., a light sensitive device such as a CCD or CMOS-type image sensor) positioned to capture an image via the lens 405. In one embodiment, the image capture arrangement 315 may further include a cleaning arrangement 415 for cleaning debris from the lens 405. Each of the lens 405, the light source 410, the image sensor 440, and the cleaning arrangement 415 is communicatively coupled to data bus 430.

In operation, the image sensor 440 receives an image as seen, for example, from the distal end of the surgical device 190 via lens 405. The image capture arrangement 315 generates image data in accordance with the image and communicates the image data to the circuit arrangement 320 via data bus 430.

In the exemplary embodiment shown, the image sensor 440 is positioned behind the lens 405. However, the image sensor 440 may be arranged in a position remote from the lens 405, with light from the lens 405 being transmitted to the image sensor 440 via, for example, fiber optic connections. In one exemplary embodiment, the image sensor 440 is positioned in the housing 305. In another exemplary embodiment, the image sensor 440 is positioned in the flexible shaft 170, a coupling thereto, and/or the electromechanical driver device 110. In any event, image data may be transmitted to the electro-mechanical driver device via a wireless or wired connection.

Figure 4B:
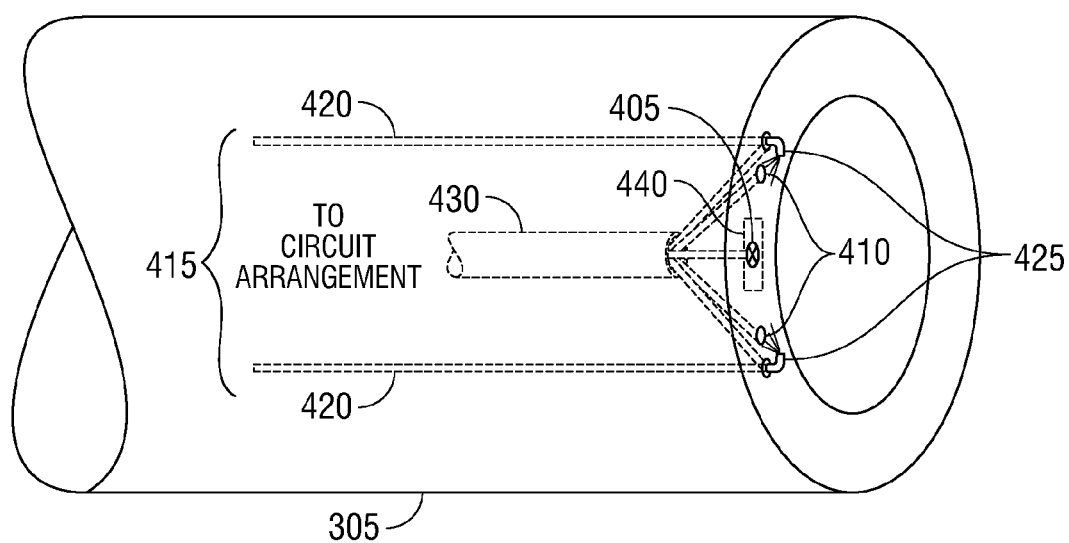

Referring now to FIG. 4b, there is a side view of the image capture arrangement 315 illustrated in FIG. 4a. The cleaning arrangement 415 may include, for example, hollow stems 420 for dispersing an air/water mixture across lens 405. For this purpose, proximal ends (not shown) of the hollow stems 420 may receive the air/water mixture from a remote source (not shown), for example, the electro-mechanical driver device 110. The air/water mixture is propelled through the hollow stems, exiting the distal ends 425 of the hollow stems 420. In this manner, the air/water mixture is dispersed across the lens 405 to help clean debris from the lens 405 during use.

In addition to communicating the image data to the circuit arrangement 320 via data bus 430, the image capture arrangement 315 receives control data from the circuit arrangement 320 via the data bus 430. The control data may, for example, control zooming of the lens 405, control the illumination produced by the light source 410, and/or control the flow rate of the air/water mixture propelled through the hollow stems 420 of the cleaning arrangement 415.

It should be appreciated that the image capture arrangement 315 may include one or more lenses 405, one or more image sensors 440, and/or one or more light sources 410. Multiple lenses 405 and/or image sensors 440 may permit a user to switch between different lenses 405 to obtain multiple views at different perspectives. For example, the user may view different images through every step of a surgical procedure. Furthermore, multiple lenses may permit panoramic or wide views.

Figure 5:
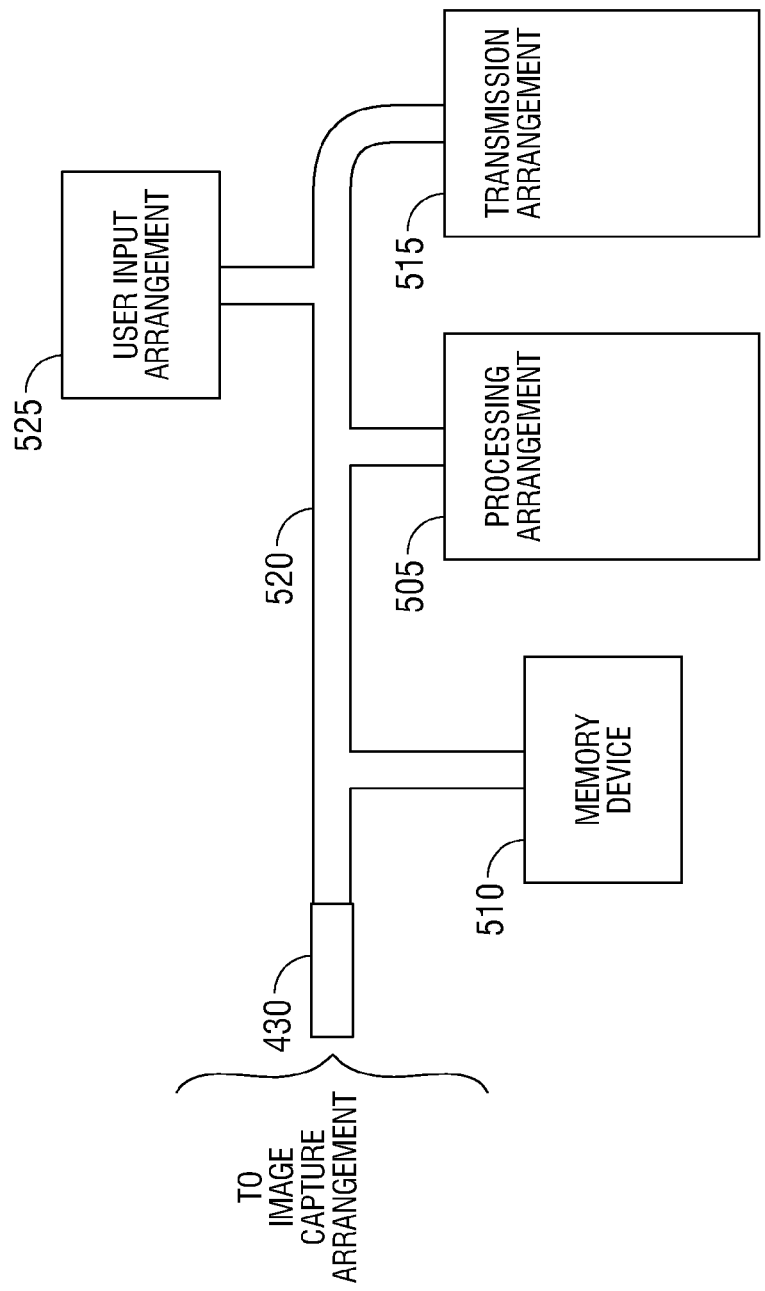
FIG. 5 illustrates an exemplary circuit arrangement, according to one embodiment of the present invention.

Referring now to FIG. 5, there is seen further detail of the circuit arrangement 320 illustrated in FIGS. 3a, 3b. The circuit arrangement 320 includes circuitry suitable for receiving the image data from the image capture arrangement 315 and communicating the image data to a remote source, such as the electro-mechanical driver device 110. The circuitry may be physically situated, for example, on a rigid or flexible circuit board situated within the housing 305 of the imaging device 300. Circuit arrangement 320 may include a processing arrangement 505, a memory device 510, user input arrangement 525, and a transmission arrangement 515, each of which is communicatively coupled via data bus 520. The data bus 430 of the image capture arrangement 315 is also communicatively coupled to the data bus 520. In this manner, the image data may be received from the image capture arrangement 315 and communicated to the processing arrangement 505 and/or the memory device 510 via data bus 520.

The memory device 510 may include any read/writable memory device capable of storing the image data, such as RAM, FLASH, EPROM, EEPROM, etc. The image data received from the image capture arrangement 315 may be, for example, stored directly on the memory device 510 for subsequent processing by the processing arrangement 505. In this manner, the memory device 510 receives the image data from the image capture arrangement 315 and then communicate the image data to the processing arrangement 505. Alternatively, the image data may be transmitted directly to the processing arrangement 505 for processing. In this manner, the processing arrangement 505 receives the image data from the image capture arrangement 315 directly via the data bus 520. Additionally, the memory device 510 may receive and store processed image data from the processing arrangement 505 for subsequent additional processing and/or for direct transmission to the remote device via the transmission arrangement 515. Alternatively, the image data may be transmitted directly from the image capture arrangement 315 to a processor of the electromechanical driver device 110.

The user input arrangement 525 is configured to receive commands from a user. The commands may include, for example, commands to zoom the lens 405, to switch between different views, to receive continuous (e.g., video) or still images, to control the illumination produced by the light source 410, to control the flow rate of the air/water mixture propelled through the hollow stems 420 of the cleaning arrangement 415, to switch to panoramic view, etc.

For this purpose, the user input arrangement 520 may include, for example, a wireless receiver for receiving the commands wirelessly from a remote control unit. Alternatively, the user input arrangement 520 may include, for example, electrical contacts for communicatively coupling to the electromechanical driver device 110 via wires disposed within the flexible shaft 170 or external to the flexible shaft 170. In this manner, the user input arrangement 520 may receive the commands via the remote power console 105 of the electromechanical driver device 110.

The user input arrangement 520 generates user input data in accordance with the commands received from the user and communicates the user input data to the processing arrangement 505 via the data bus 520. The processing arrangement 505 is configured to control the image capture arrangement 315 and process the image data in accordance with the user input data received from the user input arrangement 520.

To control the image capture arrangement 315, the processing arrangement 505 may generate control data for controlling the various functions of the image capture arrangement 315 in accordance with the user input data received from the user input arrangement 520. For this purpose, the processing arrangement 505 communicates the control data to the image capture arrangement 315 via data buses 430, 520. The control data may, for example, control zooming of the lens 405, control the illumination produced by the light source 410, and/or control the flow rate of the air/water mixture propelled through the hollow stems 420 of the cleaning arrangement 415.

The processing arrangement 505 also processes the image data in accordance with the user input data received from the user input arrangement 520. In this manner, the processing arrangement 505 may process the image data to communicate continuous or still images, to perform a digital zoom, etc. In this manner, the imaging device 300 may provide a surgeon with a video image as the surgical attachment 120 is inserted and probed through, for example, the colon area of a patient. Both moving and still images may be provided to surgeon via the imaging device 300. For example, while the surgeon is probing the colon to locate cancerous tissue, the imaging device 300 may supply a continuous image of the colon. Should the surgeon encounter an image that he or she would prefer to view as a still image, the surgeon may instantaneously freeze the moving image by activating the corresponding control mechanisms. Accordingly, the freeze frame image may be manipulated as desired, i.e., rotated, zoomed and/o magnified. The moving images may also be stored and manipulated as desired for subsequent visual analysis.

The transmission arrangement 515 receives the processed image data from the processing arrangement 505 via the data bus 520 and communicates the processed image data to the remote device (not shown). For this purpose, the transmission arrangement 515 may include a wireless transmitter operable to convert the processed image data into an RF transmission to be wirelessly received by the remote device. Alternatively, the transmission arrangement 515 may include, for example, electrical contacts for communicatively coupling to the electro-mechanical driver device 110 via wires disposed within or external to the flexible shaft 170. In this manner, the transmission arrangement 515 may communicate the processed image data to the video display 145 of the electromechanical driver device 110.

Figure 6:
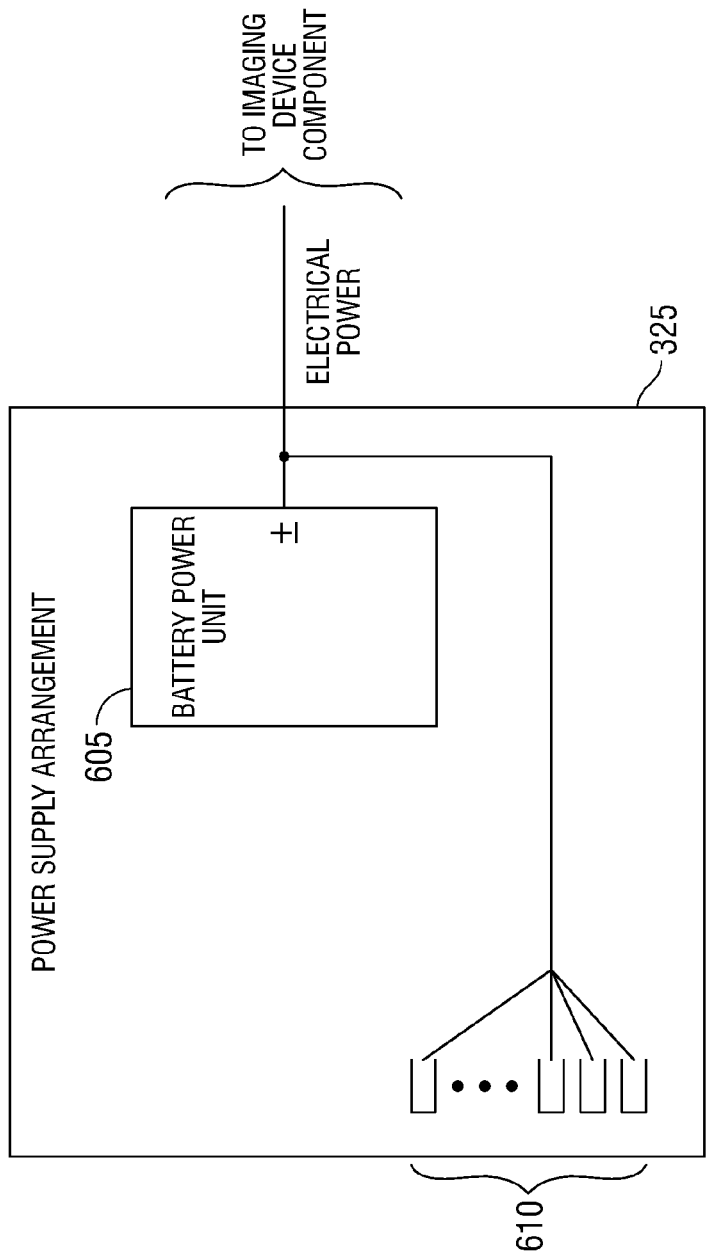
FIG. 6 illustrates an exemplary power supply arrangement for providing electrical power to an imaging device, according to one embodiment of the present invention.

Referring now to FIG. 6, there is seen further detail of the exemplary power supply arrangement 325 illustrated in FIGS. 3a, 3b. Power supply arrangement 325 includes a battery power unit 605 for providing electrical power to the imaging device 300. The battery power unit 605 may include, for example, nickel cadmium batteries, nickel metal-hydride batteries, lithium batteries, etc. In addition to or in lieu of the battery power unit 605, power supply arrangement 325 may include power contacts 610 for receiving electrical power from an external source (not shown), for example, the electromechanical driver device 110. In this manner, the electromechanical driver device 110 may transmit the electrical power to the power supply arrangement 325 via wires disposed within or external to the flexile shaft 170.

The battery power unit 605 may be configured, for example, to provide electrical power to the imaging device 300 if the power contacts 610 are not receiving electrical power from the external source, for example, from the electro-mechanical driver device 110. In this manner, the battery power unit 605 may function as a "battery-backup," to ensure that the imaging device 300 receives electrical power in the event power transmission from the external source is interrupted and/or removed.

Figure 7A:
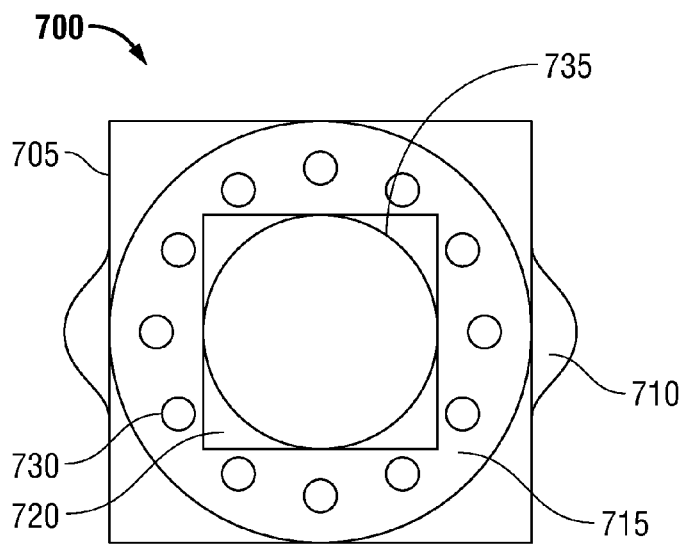
FIG. 7a illustrates another exemplary imaging device in the form of an imaging pod, according to one embodiment of the present invention.

Referring now to FIG. 7a, there is seen another exemplary imaging device in the form of imaging pod 700. The imaging pod 700 includes a housing 705 having an attachment arrangement 710 and an image capture arrangement 715 situated within the housing. The image capture arrangement 715 includes one or more light sources 730 and an optical system 720 with a focusing lens 735. The attachment arrangement 710 may include, for example, pins, spring loaded bearings, ridges, etc. configured to detachably couple the imaging pod 700 to a corresponding receptacle of the surgical device 190. The housing 705 may be formed of, for example, a transparent plastic material, although the housing may be formed of other materials as well.

Figure 7B:
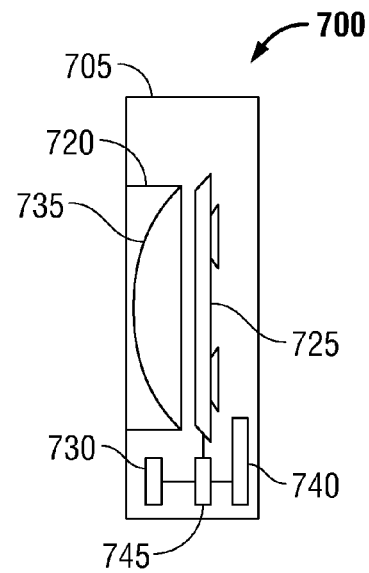
FIG. 7b is a side view of the imaging device illustrated in FIG. 7a showing further detail.

Referring now to FIG. 7b, there is seen further detail of imaging pod 700 illustrated in FIG. 7a. As seen in FIG. 7b, the image capture arrangement 715 further includes an imaging sensor, e.g., a light sensitive device such as a charged coupled device (CCD) 725. As the imaging pod is directed toward an object to be imaged, the focusing lens 735 focuses reflected light onto CCD 725. A wireless transmitter (or, e.g., a transceiver) 740 is situated in the housing 705 and communicatively coupled to the CCD 725. An example of such a wireless transmitter is described in U.S. Pat. No. 5,604,531, expressly incorporated herein by reference in its entirety. Additionally, a power source 745, such as a small battery, is situated in the housing 705 and operable to provide electrical power to the CCD 725, light sources 730, and the wireless transmitter 740. In operation, images captured by CCD 725 may be wirelessly transmitted via wireless transmitter 740 to a corresponding receiver (or transceiver) in a remote device, such as the electromechanical driver device 110.

Although, the present embodiment is described as using a CCD as an image sensor, other suitable image sensors may also be used, such as a CMOS (Complementary Metal Oxide Semiconductor) type image sensor. The CMOS sensor may require less power than a CCD image sensor, due to its greater sensitivity to light. A CMOS image sensor may include, for example, a photo diode and/or a photo transistor to detect reflected light from an object to be imaged. The CMOS image sensor may transmit the image data as an analog signal or, alternatively, as a digital signal after processing by an analog-digital converter.

Figure 7C:
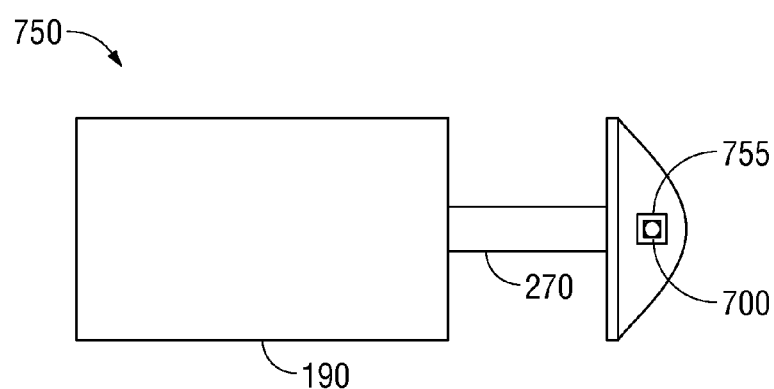
FIG. 7c illustrates a surgical attachment with an imaging pod coupled to a surgical device.

Referring now to FIG. 7c, there is seen a surgical attachment 750 including the imaging pod 700 coupled to surgical device 190. The imaging pod 700 is detachably received within a receptacle 755 of the surgical device 190. Accordingly, if the surgical device 190 is designed as a disposable unit, the imaging pod 700 may be removed from the surgical device 190 and reused in connection with another surgical device. Alternatively, the imaging pod 700 may be permanently secured to, or even integral with, the surgical device 190. In this regard, the permanently coupled imaging pod 700 would be disposed along with the surgical device 190.

Referring now to FIG. 8a, there is seen another exemplary imaging pod 800. Imaging pod 800 is similar to the imaging pod 700 described in connection with FIGS. 7a, 7b, 7c, except that imaging pod 800 includes wired connections for transmitting the image data to the remote device, such as the electromechanical driver device 110. As shown in FIG. 8, the imaging pod 800 includes contact pins 805 sized to be received in sockets of the receptacle 755 of the surgical device 190, thereby providing a plug-in type connection. When the imaging pod 800 is inserted in the surgical device 190, the contact pins 805 provide connections to circuitry 760, which supplies power to the appropriate components of the imaging pod 800 and transmits signals from the CCD 725 to a corresponding receiver in the remote device, such as the electromechanical driver device 110, through, for example, the surgical device 190 and the flexible shaft 170.

Referring now to FIG. 8b there is seen an exemplary receptacle 755 of the surgical device 190 configured to receive the imaging pod 180. As shown in FIG. 8b, the receptacle 755 includes sockets 810 sized to receive the contact pins 805 of the imaging pod 800. The sockets 810 electrically couple the contact pins 805 to electrical leads (not shown) in the surgical device 190. The electrical leads are electrically connected to the remote device (e.g., the electromechanical driver device 110) via wires situated, for example, within the flexible shaft 170 of the electro-mechanical driver device 110.

It should be appreciated that the imaging pod 800 may include a battery for power, and utilize wired transmission for signals from the CCD, or alternatively, receive power via a wired connection and utilize wireless transmission for the signals from the CCD.

Referring now to FIG. 9, there is seen another exemplary surgical attachment 900. In this embodiment, an imaging device 905 is configured to be coupled to or mounted on an external surface of the surgical device 190. Of course, the imaging device 905 may also be configured to mount on other surgical devices, such as those described in the U.S. applications incorporated by reference above.

In accordance with this exemplary embodiment, the surgical device 190 is a circular surgical stapler. The imaging device 905 is mounted to a body 910 of the surgical device 190. The surgical device 190 includes a coupling 915, an anvil portion 920 and a body 910. The anvil portion 920 includes an anvil 925 and anvil stem 930. A flexible wire assembly 940 is provided for communicating image data to a remote device, e.g., the electromechanical driver device 110 (not shown).

The imaging device 905 may slidingly fit over the body 910 and may be either permanently or removably mounted to the body 910. In the example embodiment shown in FIG. 9, the imaging device 905 is removably mounted to the body 910 via a resilient, e.g., plastic or elastic strap 935. Strap 935 may be removed, for example, which may permit the imaging device 905 to be reused with another surgical device or attachment. Alternatively, the imaging device 905 may be mounted to the surgical device 190 via a shoe (not shown) similar to the type used with a flash unit on a camera.

The video unit 100 may be coupled, for example, to a processor via a wireless connection or a wired connection via flexible wire assembly 940. The flexible wire assembly 940 may include power, control and data lines. The flexible wire assembly 940 may be coupled to, for example, a processor of a remote power console as described in, for example, U.S. patent application Ser. No. 09/836,781. Of course, in lieu of the flexible wire assembly 940, the wired connection between the imaging device 905 and, for example, the processor, may be effected via individual wires disposed within or external to the flexible shaft 170 of the electromechanical driver device 110.

It should be appreciated that the wires of the flexible wire assembly 940 and/or the wires disposed within or external to the flexible shaft 170 of the electro-mechanical driver device 110 for communicating image data from the imaging device 905 to, for example, the processor, may be replaced with fiber-optic connections.

Imaging device 905 may include analogous features to the imaging devices 300 and 700 described above. For example, imaging device 905 may include an image capture arrangement (e.g., a camera), a circuit arrangement electrically coupled to the image capture arrangement, and a power supply arrangement for supplying power to the imaging device 905.

The image capture arrangement of the imaging device 905 may include a lens, a light source for illuminating an object to be imaged (e.g., fiber optic light sources, light bulbs, LEDs, etc.), an image sensor (e.g., a CCD or CMOS-type image sensor) positioned to capture an image via the lens. In one embodiment, the image capture arrangement of the imaging device 905 may further include a cleaning arrangement for cleaning debris from a lens. Each of the lens, the light source, the image sensor, and the cleaning arrangement may also communicatively coupled to data bus.

Figure 10:
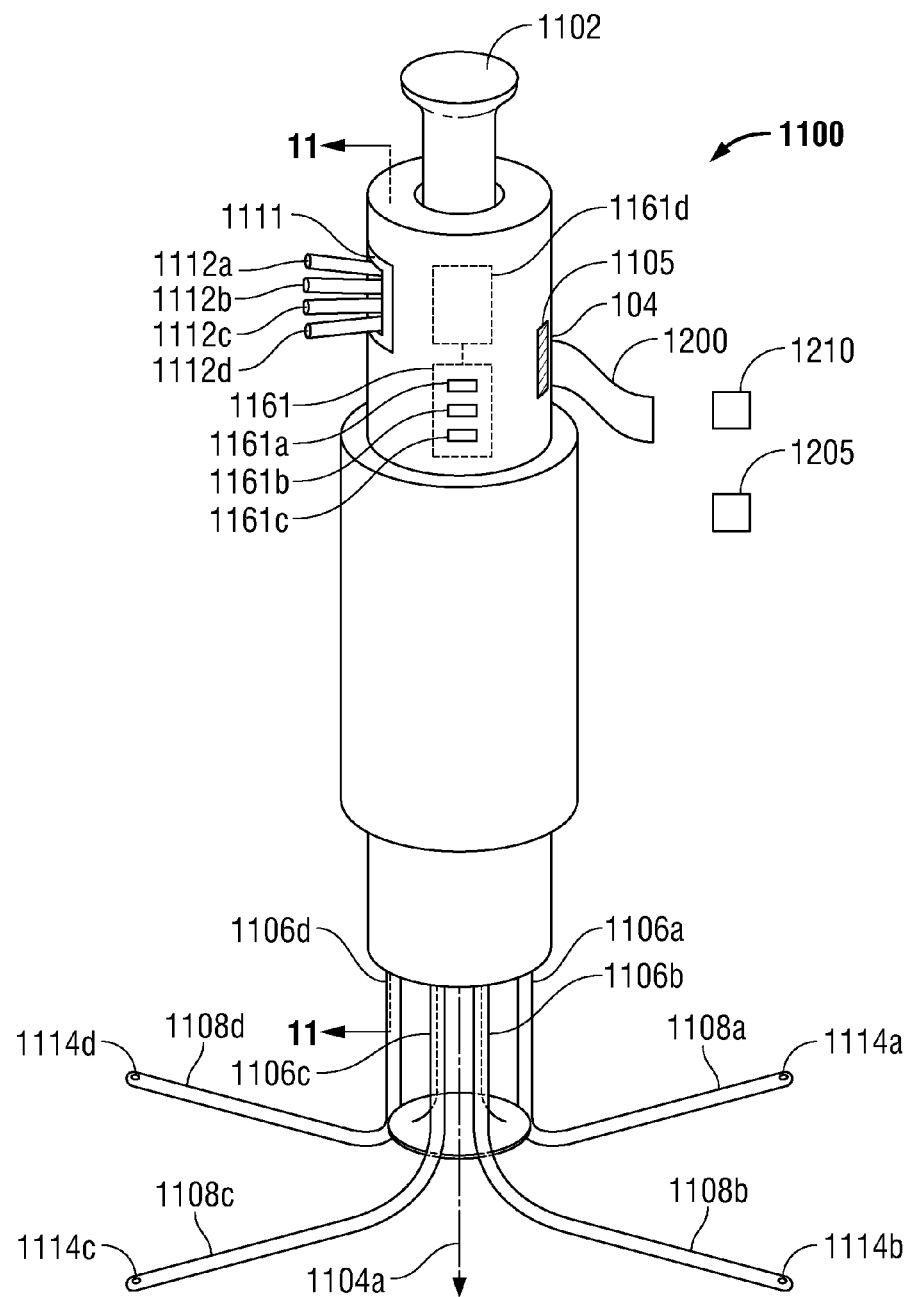
FIG. 10 shows a perspective view of a surgical imaging device, in accordance with one embodiment of the present invention.

FIG. 10 shows a perspective view of a surgical imaging device 100 according to another example embodiment of the present invention. The surgical imaging device 1100 includes a body portion 104 which encloses legs 1106a to 1106d and a retraction actuator 1102. The legs 1106a to 1106d are connected to levers 1112a to 1112d, respectively. Prongs 1108a to 1108d extend from legs 1106a to 1106d, respectively. Located at or near the distal tip of each prong 1108a to 1108d is a camera 1114a to 1114d, respectively.

According to one embodiment of the present invention, the legs 1106a to 1106d, along with their respective prongs 1108a to 1108d, are moveable. For instance, the legs 1106a to 1106d may be moveable within a cylindrical opening of the body portion 1104 (explained in more detail below) so that the legs 1106a to 1106d move radially around a central axis 1104a of the body portion 1104. In addition, the legs 1106a to 1106d may be rotatably moveable, e.g., rotatable around their own central axes, within the body portion 1104, so that the prongs 1108a to 1108d may be caused to swivel around the central axes of the legs 1106a to 1106d, respectively. The legs 1106a to 1106d may be moveable in both of these ways by the operation of the levers 1112a to 1112d, respectively, as further described below. The control levers 1112a to 1112d extend through opening 1111. Specifically, the movement of the legs 1106a to 1106d within the body portion 1104 is more fully described below in connection with FIGS. 15, 16 and 17.

In addition, the prongs 1108a to 1108d may be moveable relative to their respective legs 1106a to 1106d. For instance, the prongs 1108a to 1108d may be moveable between an extended position, in which each prong 1108a to 1108d is positioned in substantially the same plane, e.g., each being substantially perpendicular to its respective legs 1106a to 1106d, and a retracted position, in which each prong 1108a to 1108d is not positioned in substantially the same plane, e.g., is not substantially perpendicular to its respective legs 1106a to 1106d. The movement of the prongs 1108a to 1108d between an extended position and a retracted position is more fully described below in connection with FIG. 18.

The body portion 1104 may also include a memory device 1161. In one embodiment of the present invention, the memory device 1161 stores data corresponding to the surgical imaging device 1100. Data stored in the memory device 1161 may include model/serial number identification 1161a, usage data 1161b, image data 1161c and processing data 1161d. The model/serial number identification 1161a uniquely identifies the surgical imaging device 1100. The usage data 1161b may include, e.g., information concerning the number of hours the surgical imaging device 1100 has been used and the types of procedures that have been viewed using the surgical imaging device 1100. The image data 1161c may include, e.g., video clips, still frames, etc., which depict visual images of the body cavity. In one embodiment of the present invention, the user may label and categorize the image data 1161c while using the imaging device 1100 during a surgical procedure. In addition, the usage data 1161b and image data 1161c may be transferred for permanent storage on a storage device, e.g., floppy disk, CD, hard drive disk, etc., so that a surgeon may review the stored data at a future date.

The body portion 1104 may also include a processor 1161d. In one embodiment of the present invention, the processor 1161d is configured to process data, such as image data 1161c, and may include, e.g., an operating program which controls the operation of the surgical imaging device 1100 or that controls the processing of the data, e.g., the image data 1161c. For instance, the processor 1161d may include an operating program that controls or operates the various functions of the surgical imaging device 1100, such as lens movement, adjustment of light intensity, zoom magnification, color, brightness and focus.

The body portion 1104 of the surgical imaging device 1100 may also include a slot 1105 configured to receive a control cable 1200, as further described below in connection with FIG. 14. Generally, the control cable 1200 conveys data and/or power between the cameras 1114a to 1114d and a video display device 1205 and/or a power supply 1210.

Figure 11:
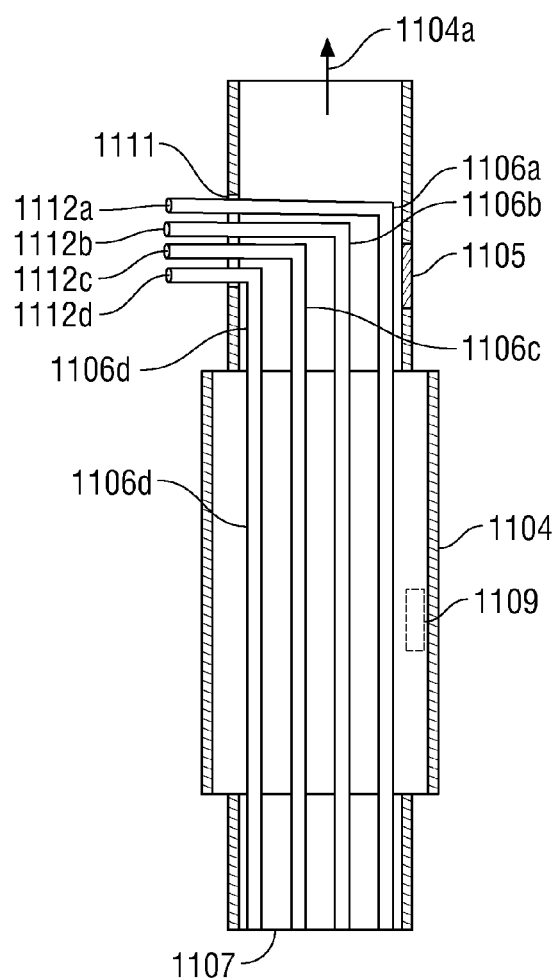
FIG. 11 illustrates a cross-sectional view of a body portion of the surgical imaging device shown in FIG. 10, taken along the lines B-B.

FIG. 11 illustrates a cross-sectional view of the body portion 1104 shown in FIG. 10, taken along the lines B-B. As previously mentioned, in this embodiment, the legs 1106a to 1106d connect to control levers 1112a to 1112d, respectively. The control levers 1112a to 1112d extend through opening 1111 and may be movable in a radial direction relative to the central axis 1104a of the body portion 1104. The legs 1106a to 1106d extend axially through the body portion 1104 and out of cylindrical opening 1107. The opening 1111 is configured so as to provide sufficient movement to the control levers 1112a to 1112d to enable the legs 1106a to 1106d to be moved between different positions in the cylindrical opening 1107 of the body portion 1107, as further described below.

As described above, located at or near the distal tip of prongs 1108a to 1108d are cameras 1114a to 1114d, respectively. FIGS. 12 and 13 illustrate a prong 1108 having a camera 1114, according to one embodiment of the present invention. In FIG. 12 there is shown a camera 1114 that includes a lens 1116 and an imaging sensor 1118. One or more light sources 1115 may be mounted adjacent to the camera 1114 and provide light to enable the imaging sensor 1118 to sense an image. The prong 1108 may also include a control line 1122 having control and power leads that transmit power to the imaging sensor 1118 and to the light sources 1155, and/or transmit image data signals to and from the imaging sensor 1118. The light sources 1115 may include, e.g., light-emitting diodes.

FIG. 13 is a cross-sectional view of the prong 1108 shown in FIG. 12, taken along the lines A-A. FIG. 13 illustrates the camera 1114 including a pair of lenses 1116, lens covers 1120 for protecting the lenses 1116, and the imaging sensor 1118. The imaging sensor 1118 may be, for example, a charged coupled device (hereinafter referred to as a "CCD"). The imaging sensor 1118 receives an image from lens 1116 and converts the image to image data, e.g., electronic signals, for transmission through the control line 1122. The camera 1114 may also include internal circuitry that converts images captured by the imaging sensor 1118 into electrical signals for transmission to a video display device.

Although one embodiment of the present invention employs a CCD as the imaging sensor 1118, other suitable imaging sensors may also be used. In another exemplary embodiment of the present invention, the imaging sensor 1118 is an integrated circuit using a Complementary Metal Oxide Semiconductor (hereinafter referred to as "CMOS") process. A CMOS type image sensor may include a photo diode or photo transistor as the light detecting element. Furthermore, a CMOS image sensor may transmit analog signals or use an analog-digital converter for signal transmission. The CMOS sensor may provide an alternative to the CCD sensor that would require less power during operation due to its greater sensitivity to light. U.S. patent application Ser. No. 10/127,310, filed on Apr. 27, 2002, which is expressly incorporated herein by reference in its entirety, describes other possible imaging devices and arrangements that may be used in connection with the example embodiment.

FIG. 14 illustrates a control cable 1200 according to one embodiment of the present invention. The control cable 1200 includes coupling 1211, leads 1215 and coupling 1212. The control cable 1200 is configured to attach, via coupling 1211, to slot 1105 located on body portion 1104. Leads 1215 transmit signals to and from the imaging sensors 1118 in each cameras 1114a to 1114d. In addition, leads 1215 may transmit power for energizing the various components of the cameras 1114a to 1114d. The coupling 1212 is configured to attach to the video display device 1205, such as a television monitor, computer monitor, CRT or similar viewing device, which receives and processes the image data for viewing, and/or to attach to a power supply 1205.

Figure 15:
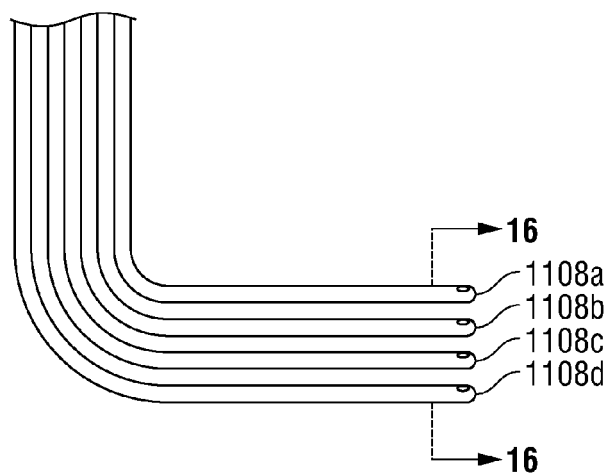
FIG. 15 illustrates the legs and prongs of the surgical imaging device in a first position, according to one embodiment of the present invention.
Figure 16:
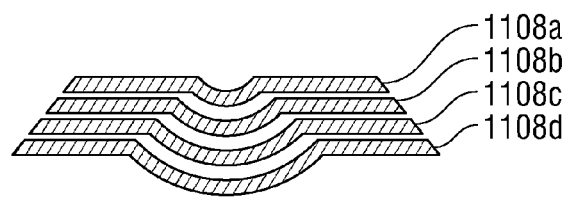
FIG. 16 illustrates a cross-sectional view of the prongs shown in FIG. 15, taken along the lines C-C.

As described above, in one embodiment of the present invention, the legs 1106a to 106d, along with their respective prongs 1108a to 1108d, are moveable between various positions. For instance, the legs 1106a to 1106d, along with their respective prongs 1108a to 1108d, may be moveable between a first position, in which the prongs 1108a to 1108d are parallel to each other, and a second position, in which the distal ends of the prongs 1108a to 1108d are not parallel to each other. FIG. 15 illustrates the legs 1106a to 1106d, along with their respective prongs 1108a to 1108d, in a first position. In this first position, the legs 1106a to 1106d are rotated in the body portion 1104 such that the distal ends of the prongs 1108a to 1108d, e.g., the ends of the prongs 1108a to 1108d having the cameras 1114a to 1114d, respectively, are positioned adjacent to each other. In one embodiment of the present invention, the prongs 1108a to 1108d are configured so as to fit together, thereby reducing the cross-sectional area of the distal ends of the prongs 1108a to 1108d. For instance, FIG. 16 illustrates a cross-sectional view of the prongs 1108a to 1108d shown in FIG. 15, taken along the lines C-C, wherein the distal ends of the prongs 1108a to 1108d each have a complementary cross-sectional shape relative to each other so as to minimize the cross-sectional areas of the prongs 1108a to 1108d when parallel to each other. This parallel position is suitable for maneuvering the prongs 1108a to 1108d into and out of an incision in a patient, as more fully described below.

FIG. 10, explained in detail above, illustrates the legs 1106a to 1106d, along with their respective prongs 1108a to 1108d, in the second position. In this second position, the legs 1106a to 1106d are rotated in the body portion 1104 such that the prongs 1108a to 1108d are moved within a substantially same plane, e.g., a plane that is substantially perpendicular to the central axis 1104a of the body portion 1104, so as to be not parallel to each other. For instance, FIG. 10 illustrates the legs 1106a to 1106d, along with their respective prongs 1108a to 1108d, rotated in the body portion 1104 such that the prongs 1108a to 1108d are radially separated relative to each other and positioned approximately 90 degrees apart from each other relative to the central axis 1104a of the body portion 1104.

Figure 17:
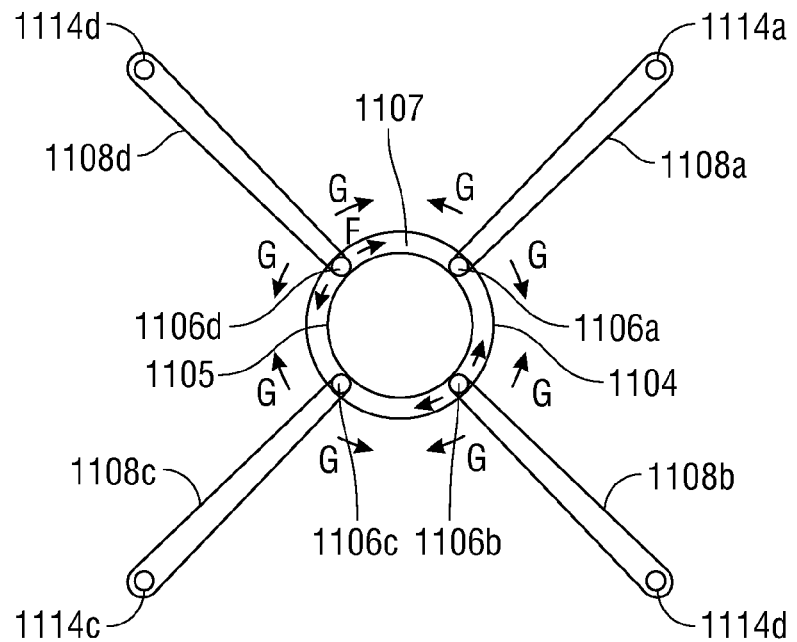
FIG. 17 is a bottom view of the surgical imaging device shown in FIG. 10.

Another view of the legs 1106a to 1106d and the prongs 1108a to 1108d in the second position is shown in FIG. 17. FIG. 17 is a bottom view of the surgical imaging device 1100 shown in FIG. 10. In the embodiment shown in FIG. 17, arrows F illustrate the directions that the legs 1106b, 1106c and 1106d may move within the cylindrical opening 1107 of the body portion 1104. In addition, arrows G illustrate the directions that the prongs 1108a to 1108d may move when their respective legs 1106a to 1106d are rotated around their respective central axes.

Figure 18:
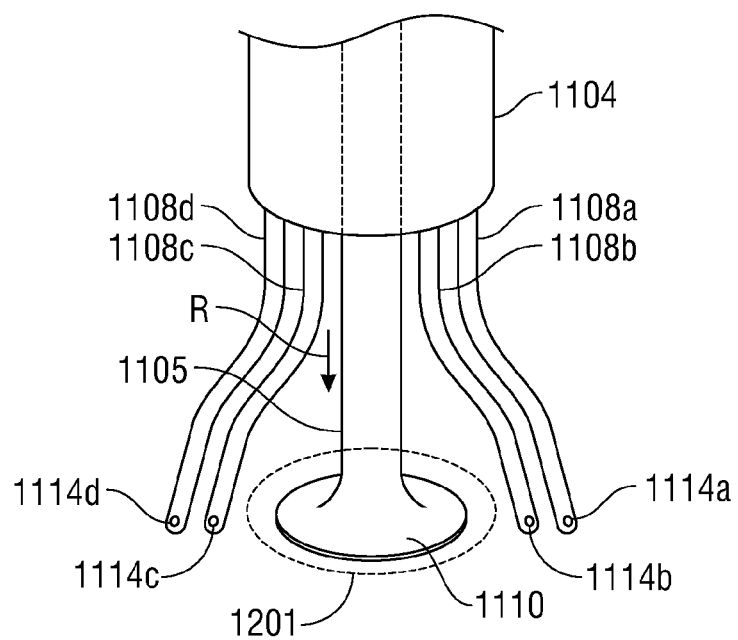
FIG. 18 illustrates the surgical imaging device shown in FIG. 10 in a retracted position, according to one embodiment of the present invention.

As previously mentioned, in addition to the movement of the legs 1106a to 1106d and their prongs 1108a to 1108d as shown in FIG. 17, the prongs 1108a to 1108d are also moveable between an extended position and a retracted position. FIG. 10, described above, illustrates the prongs 1108a to 1108d in an extended position, in which each prong 1108a to 1108d is in a substantially same plane, e.g., each being substantially perpendicular to its respective legs 1106a to 1106d. FIG. 18, on the other hand, illustrates the surgical imaging device 1100 in a retracted position. As mentioned previously, in the embodiment shown, the prongs 1108a and 1108b of the surgical imaging device 1100 are not substantially perpendicular to their respective legs 1106a to 1106d in the retracted position. In the retracted position, the prongs 1108a to 1108d of the surgical imaging device 1100 are moved relative to their respective legs 1106a to 1106d such that the camera 1114a to 1114d of each of the prongs 1108a to 1108b is directed to a region of space. In one embodiment of the present invention, the prongs 1108a to 1108d of the surgical imaging device 1100 are moved relative to their respective legs 1106a to 1106d such that the imaging sensor 1118 mounted in each of the prongs 1108a to 1108b is directed to the same region of space, such as region of space 1201 illustrated in FIG. 18. The region of space 1201 may be a region of space in which a surgical instrument is being used during a surgical procedure. Thus, in this embodiment, in the retracted position, the imaging sensor 1118 of each of the prongs 1108a to 1108b provide a view of a surgical site during a surgical procedure from a different angle. Alternatively, the prongs 1108a to 1108d of the surgical imaging device 1100 may be moved such that the imaging sensor 1118 of each of the prongs 1108a to 1108b are directed to different regions of space.

In one embodiment, the surgical imaging device 1100 is moved from an extended position into the retracted position by the actuation of the retraction actuator 1105. The retraction actuator 1105 moves axially relative to the body portion 1104 such that, during retraction, the bottom portion 1110 of the retraction actuator 1102 moves away from the body portion 1104 in the direction indicated by arrow R. The prongs 1108a to 1108d are preferably made of a flexible material, enabling the prongs 1108a to 1108d to bend when force is exerted thereon. For instance, as the bottom portion of the retraction actuator 1102 is moved into a body cavity, a force may be exerted on the prongs 1108a to 1108d by the walls of a body cavity. As a result, the prongs 1108a to 1108d may be caused to bend and may form, as shown in FIG. 18, a curved shape. In one embodiment, the curved shape of each of the prongs 1108a to 1108d conform to the walls of the body cavity in which the prongs 1108a to 1108d are disposed. In this manner, the imaging sensor 1118 positioned at the tip of each prong 1108a to 1108d may provide a user with multiple views of the body cavity area. In addition, the user may rotate each prong 1108*a* to 1108*d* in order to view the body cavity from various angles.

Figure 19:
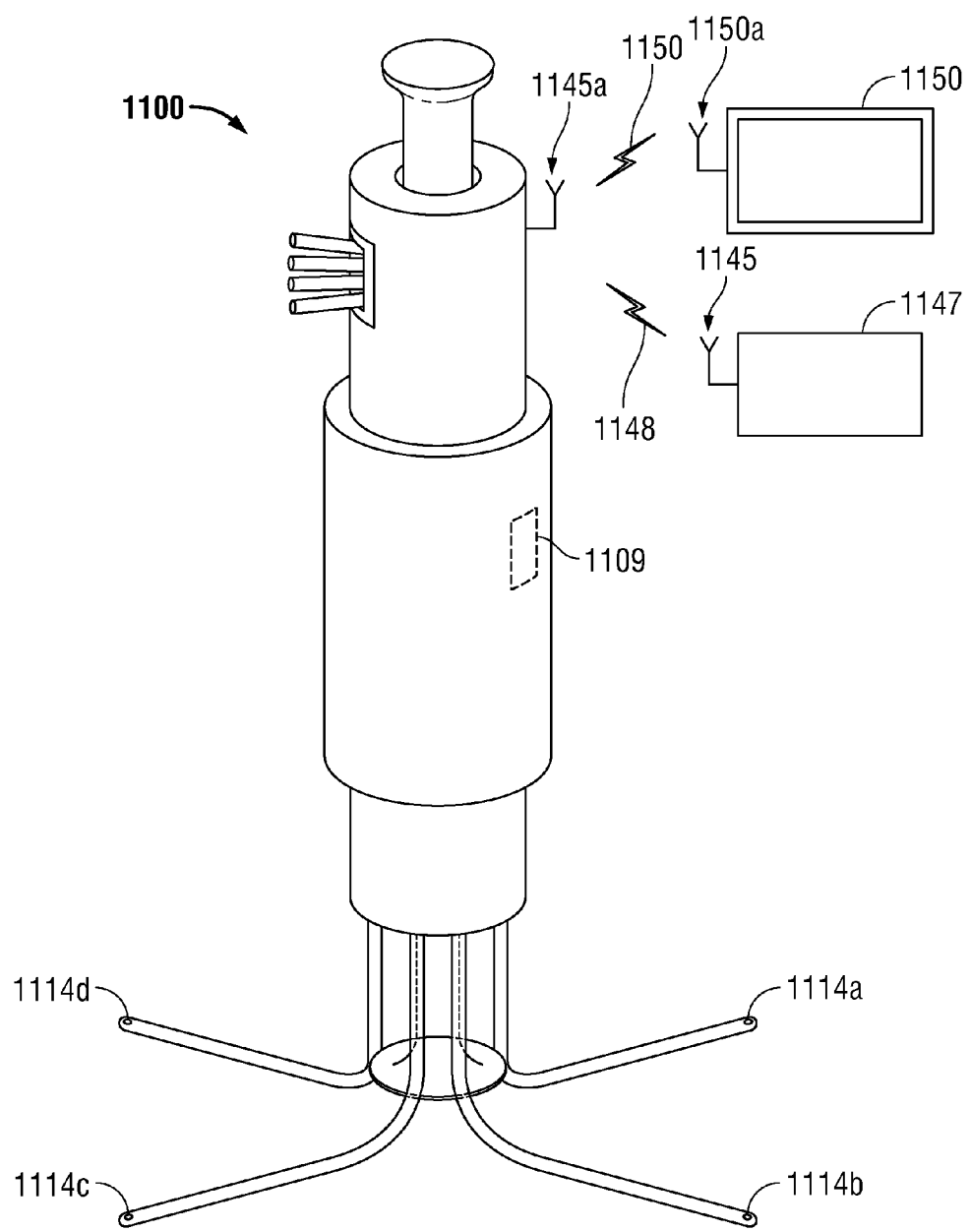
FIG. 19 illustrates a wireless arrangement for wirelessly transmitting image data for display on a video display device, according to one embodiment of the present invention.

As previously described, the image data may be transmitted via the control cable 1200 inserted at one end into the slot 1105 of the body portion 1104 and inserted at the other end to a video display device 1205. Alternatively, the image data may be transmitted wirelessly for display on a video display device. For instance, the surgical imaging device 1100 may include a wireless arrangement for wirelessly transmitting the image data for display on a video display device. FIG. 19 illustrates one embodiment of the present invention that employs a wireless arrangement for wirelessly transmitting the image data for display on a video display device. Specifically, and as illustrated in FIG. 19, the surgical imaging device 1100 may include an antenna 1145*a* configured to transmit image data and/or control signals. The antenna 1145*a* of the surgical imaging device 1100 may receive control signals 1148 from the antenna 1145*b* of a remote control unit 1147. These control signals may include, for instance, signals that control the imaging sensors 1118, the intensity of the light provided by the light sources 1115, or any other signals for controlling the operation of the surgical imaging device 1100. In addition, the surgical imaging device 1100 may transmits video signals 1158 via the antenna 1145*a* of the surgical imaging device 1100 to an antenna 1150*a* of a video display device 1150.

In another embodiment, the cameras 1114*a* to 1114*d* may include wireless circuitry that enables the transmission of wireless signals 1158 directly to the video display device 1150. Since the wireless embodiment of the surgical imaging device 1100 enables the control cable 1200 and the power supply 1210 to be eliminated, the surgical imaging device 1100 may, as shown in FIG. 19, include a local power source, e.g., a battery, 1109. The local power source 1109 may supply power to the imaging sensors 1118, the light sources 1115, any additional internal circuitry in the cameras 1114*a* to 1114*d*, etc. In this wireless embodiment of the present invention, the surgical imaging device 1100 may also eliminate the slot 1105 of the body portion 1104 (shown in FIG. 10) that is configured to receive the control cable 1200.

In still another embodiment, the surgical imaging device 1100 may be equipped to alternatively function in either a wired or wireless format. In this embodiment, the slot 1105 may have a cover which would enable the user to cover the slot 1105 when the imaging device 1100 is operated wirelessly. Should the user desire to operate the surgical imaging device 1100 in a wired format, the user may remove the cover and attach the control cable 1200 into the slot 1105. In this embodiment, the operating program for the imaging device 1100 is advantageously configured to detect when the control cable 1200 is or is not attached to the slot, and to operate the surgical imaging device 1100 in either the wired or the wireless formats in accordance therewith.

Figure 21:
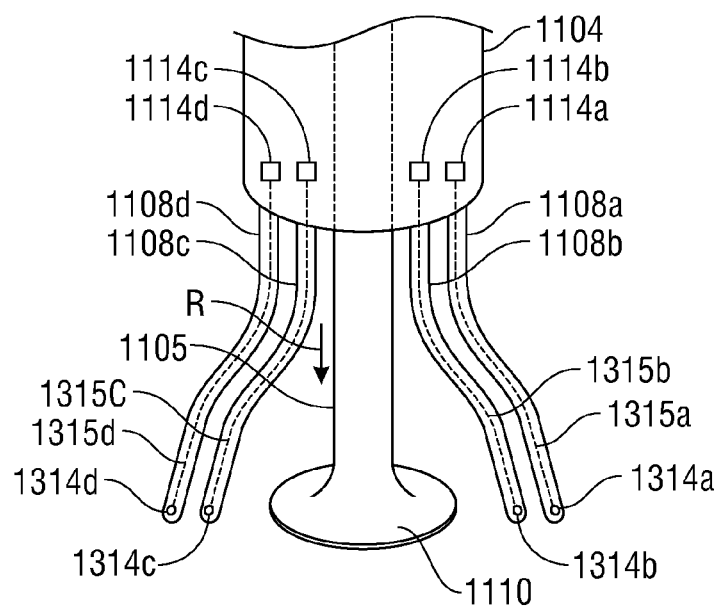
FIG. 21 illustrates a surgical imaging device having imaging sensors provided in a body portion, according to one example embodiment of the present invention.

In another example embodiment of the present invention, one or more imaging sensors, e.g., imaging sensors 1118, may be provided in the body portion, e.g., body portion 1104, or in a remote device. FIG. 21 illustrates one example embodiment having imaging sensors 1118 provided in the body portion 1104. In this embodiment, the prongs 1108*a* to 1108*d* include light guides, such as light guides 315*a* to 315*d*, and/or a lens system, such as lens systems 314*a* to 314*d*, which guide light reflected in the body cavity to the imaging sensors 1118*a* to 1118*d* in order to remotely capture an image of the body cavity. For example, fiber optics may be used in this regard.

Figure 20A:
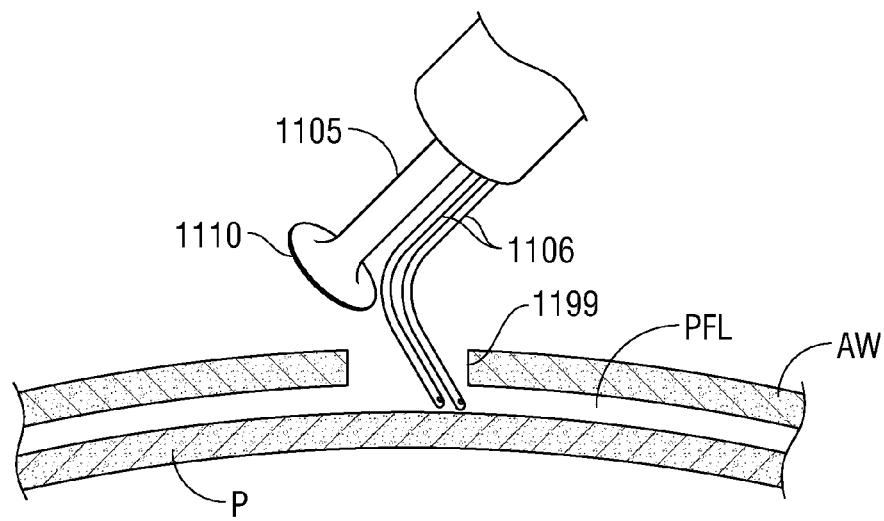
FIGS. 20(*a*) to 20(*c*) illustrate the operation of the surgical imaging device to perform an exemplary type of surgical procedure, according to one example embodiment of the present invention.
Figure 20B:
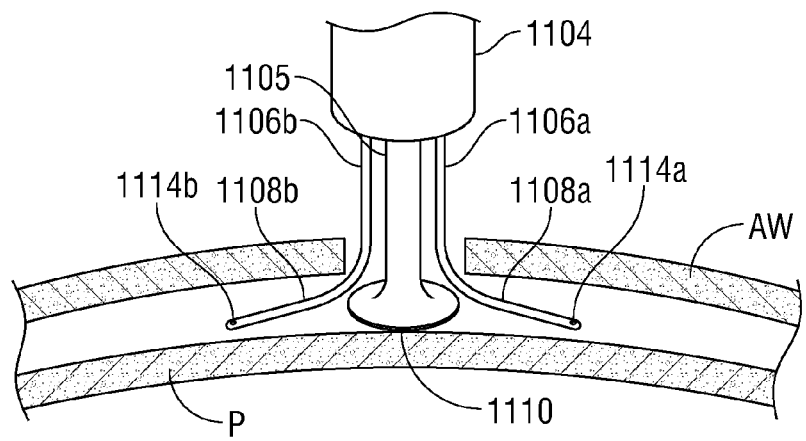
Figure 20C:
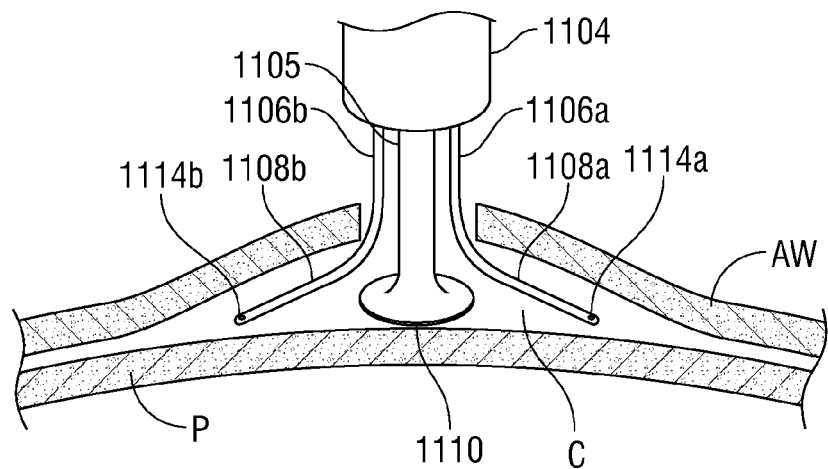

The surgical imaging device 1100 of the present invention may be used in various types of surgical procedures. FIGS. 20(*a*) to 20(*c*) illustrate the operation of the surgical imaging device 1100 to perform an exemplary type of surgical procedure, e.g., abdominal surgery. It should be recognized that this is merely one of many types of surgical procedures that may be performed with the surgical imaging device 1100 of the present invention. According to this exemplary procedure and referring to FIG. 20(*a*), an incision 1199 is made in the abdominal wall AW to the peritoneal fat layer PFL. The prongs 1108*a* to 1108*d* are inserted through the incision 1199. In order to facilitate the insertion of the prongs 1108*a* to 1108*d* and to minimize the size of the incision required, the prongs 1108*a* to 1108*d* may be positioned by the user in the first position, e.g., the first position illustrated in FIG. 15 wherein the prongs 1108*a* to 1108*d* are parallel to each other. As the prongs 1108*a* to 1108*d* are inserted they separate the peritoneum P from the properitoneal fat layer PFL.

After the prongs 1108*a* to 1108*d* and the bottom portion 1110 have been inserted into the incision, the user may use the control levers 1112*a* to 1112*d* to separate the prongs 1108*a* to 1108*d*. FIG. 20(*b*) illustrates the surgical imaging device 1100 after the prongs 1108*a* to 1108*d* and the bottom portion 1110 have been inserted into the incision and the prongs 1108*a* to 1108*d* have been separated. As shown in FIG. 20(*b*), the prongs 1108*a* to 1108*d* may be separated until the prongs 1108*a* to 1108*d* are in the second position, e.g., the second position illustrated in FIGS. 10 and 17 wherein the prongs 1108*a* to 1108*d* are approximately 90 degrees apart from each other relative to the central axis 1104*a* of the body portion 1104.

After the prongs 1108*a* to 1108*d* are separated the user may apply downward pressure to the retraction actuator 1102. As the user extends retraction actuator 1102 through the incision, the bottom portion 1110 of the retraction actuator 1102 pushes on the peritoneum P so that the peritoneum P is detached from the properitoneal fatty layer PFL, but without piercing the peritoneum P. In this manner, a cavity C is formed between the abdominal wall AW and the peritoneum P, allowing a surgeon with space to perform a surgical procedure. FIG. 20(*c*) illustrates the surgical imaging device 1100 after the bottom portion 1110 of the retraction actuator 1102 has pushed the peritoneum P so as to form the cavity C between the abdominal wall AW and the peritoneum P. FIG. 20(*c*) also illustrates that during the extension of retraction actuator 1102 and as the cavity C is formed between the abdominal wall AW and the peritoneum P, the prongs 1108*a* to 1108*d* are caused to bend in conformance with the curvature of the properitoneal fatty layer PFL. Once the prongs 1108*a* to 1108*d* are placed in the retracted position as shown in FIG. 20(*c*), the surgeon may provide power via power supply 1210 to the light sources 1115 and to the imaging sensors 1118 so as to generate image data of the cavity C. In this retracted position, the image sensors 1118 of each of the prongs 1108*a* to 1108*d* provide multi-directional views of the cavity C, allowing a surgeon to view the surgical procedure being performed in the cavity C from various angles. If additional views are required, the surgeon may manipulate the control levers 1112*a* to 1112*d* until the desired view is obtained.

Thus, the surgical imaging device of the present invention in accordance with various embodiments thereof, may reduce the difficulty in obtaining different views of a surgical site in a body cavity. Unlike conventional surgical cameras, which require a surgeon to remove the camera from a first incision, to make another incision in the patient, and to reinsert the camera into the second incision in order to change the view of the surgical site and/or to examine the surgical site from a different angle, the surgical imaging device of the present invention permits multiple views to be seen without removing the device. Instead, the surgeon may view the surgical site from different angles simply by viewing the image data from the various image sensors situated in different locations within the surgical site. Furthermore, if these views are inadequate, the surgeon may move the prongs 1108a to 1108d as desired via the control levers 1112a to 1112d to obtain new views without the need to remove the device or make additional surgical incisions. Still further, the surgical imaging device of the present invention in accordance with various embodiments thereof provides for a single device that enables a cavity to be formed in the surgical site, thereby providing space for performing the surgical procedure. In addition, the surgical imaging device of the present invention in accordance with various embodiments thereof provides for one or more light sources that provide light in the surgical site, thereby enabling the image sensors to provide useful image data without the need for making additional incisions to insert additional light sources.

Figure 22:
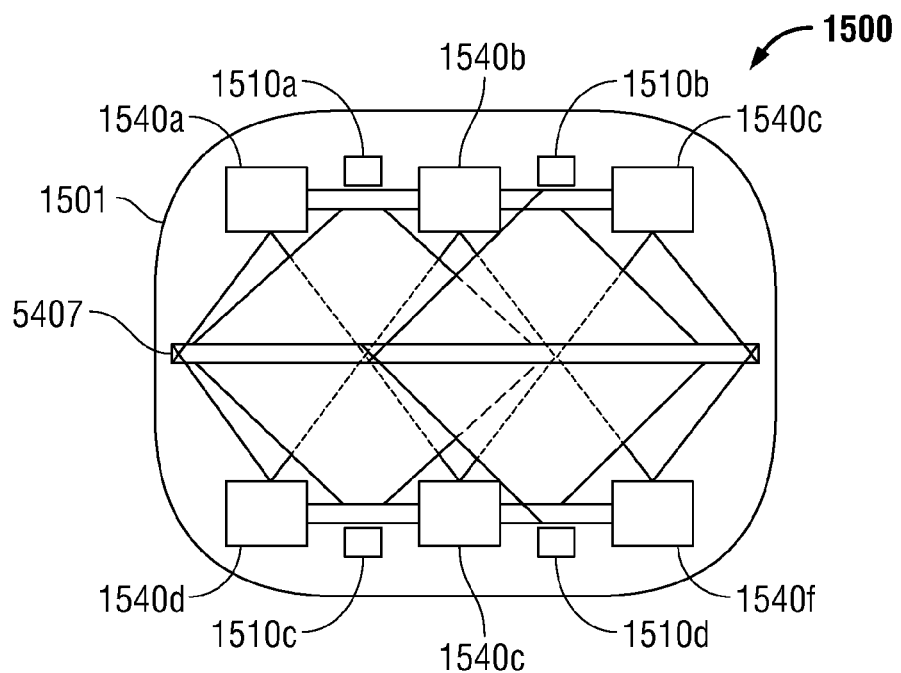
FIG. 22 is a schematic diagram that illustrates an exemplary surgical image capture arrangement, in accordance with another embodiment of the present invention.

FIG. 22 is a schematic diagram that illustrates an exemplary surgical image capture arrangement 1500, in accordance with one embodiment of the present invention. As shown in FIG. 22, the image capture arrangement 1500 includes at least one light source 1510, such as light sources 1510a, 1510b, 1510c and 1510d. It should be recognized that any number of light sources 1510 may be employed. The light source 1510 is configured to illuminate an object to be imaged. As set forth more fully above, the light source 1510 may be, for example, a fiber optic light source, light bulbs, LEDs, etc. FIG. 22 illustrates one possible arrangement, having four light sources 1510, such as might be employed to illuminate an abdominal cavity (shown schematically as cavity 1501), or any other cavity, of a patient. For the purposes of example only, the arrangement described below refers to a surgical image capture arrangement 1500 that is employed within an abdominal cavity 1501 of a patient. Preferably, the light sources 1510 are positioned within the abdominal cavity 1501 so as to illuminate the abdominal cavity 1501 from various angles so as to insure that the abdominal cavity and objects within the abdominal cavity 1501 are adequately illuminated from all angles.

The image capture arrangement 1500 also includes at least two image sensors 1540. In the embodiment shown, the image capture arrangement 1500 includes six image sensors 1540, shown here as image sensors 1540a, 1540b, 1540c, 1540d, 1540e and 1540f. It should be recognized that any number of image sensors 1540 may be employed. The image sensors 1540 are each configured to capture an image, e.g., via a lens. As set forth more fully above, the image sensor 1540 may be, for example, a light sensitive device such as a CCD or CMOS-type image sensor. Preferably, the image sensors 1540 are positioned within the abdominal cavity 1501 so as to capture images that correspond collectively to the entire abdominal cavity 1501. However, it should be recognized that, while the image sensors 1540 are preferably positioned within the abdominal cavity 1501 so as to capture images that correspond collectively to the entire abdominal cavity 1501, in other embodiments, the image sensors 1540 are positioned within the abdominal cavity 1501 so as to capture images that correspond collectively to a portion less than the entirety of the abdominal cavity 1501. In addition, the image sensors 1540 are preferably positioned within the abdominal cavity 1501 relative to the light sources 1510 that are also positioned within the abdominal cavity 1501 so as to capture images that are adequately illuminated by the light sources 1510.

Figure 23:
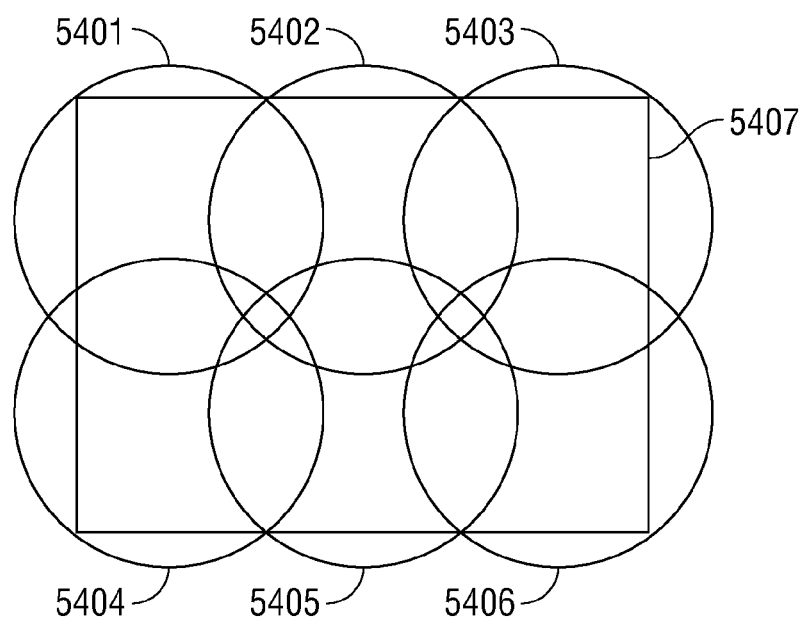
FIG. 23 is a schematic diagram that illustrates a plurality of image frames.

An image that is captured by each respective image sensor 1540 is referred to herein as an image frame. FIG. 23 is a schematic diagram that illustrates a plurality of image frames 5400. As shown in FIG. 23, each image frame 5400 corresponds to an image that is captured by an image sensors 1540. For instance, the image frame 5401 corresponds to the image that is captured by the image sensor 1540a. Likewise, the image frames 5402, 5403, 5404, 5405 and 5406 correspond to the images that are captured by the image sensors 1540b, 1540c, 1540d, 1540e and 1540f, respectively.

Preferably, the image sensors 1540 are positioned within the abdominal cavity 1501 such that the image frames captured by each image sensor 1540 overlap to form a composite image. FIG. 23 illustrates that the image frames 5401 to 5406 captured by the image sensors 1540a to 1540f, respectively, overlap to form a composite image 5407. The composite image 5407 may include selected portions of each of the image frames 5401 to 5406. As stated above, the composite image 5407 preferably corresponds to an image of the entire abdominal cavity 1501. However, in other embodiments, the composite image 5407 corresponds to an image of a portion of the abdominal cavity 1501. In one embodiment, the composite image 5407 has an aspect ratio of 16:9. In another embodiment, the composite image 5407 has an aspect ratio of 4:3. It should be recognized that the composite image 5407 may have any conceivable aspect ratio. It is noted that, while FIG. 23 illustrates the composite view 5407 of the abdominal cavity 1501 in a front view, FIG. 22 also illustrates the composite view 5407, but in a top view. Thus, FIG. 22 illustrates one manner in which multiple image sensors 1540 may be employed to generate the composite view 5407.

Figure 24:
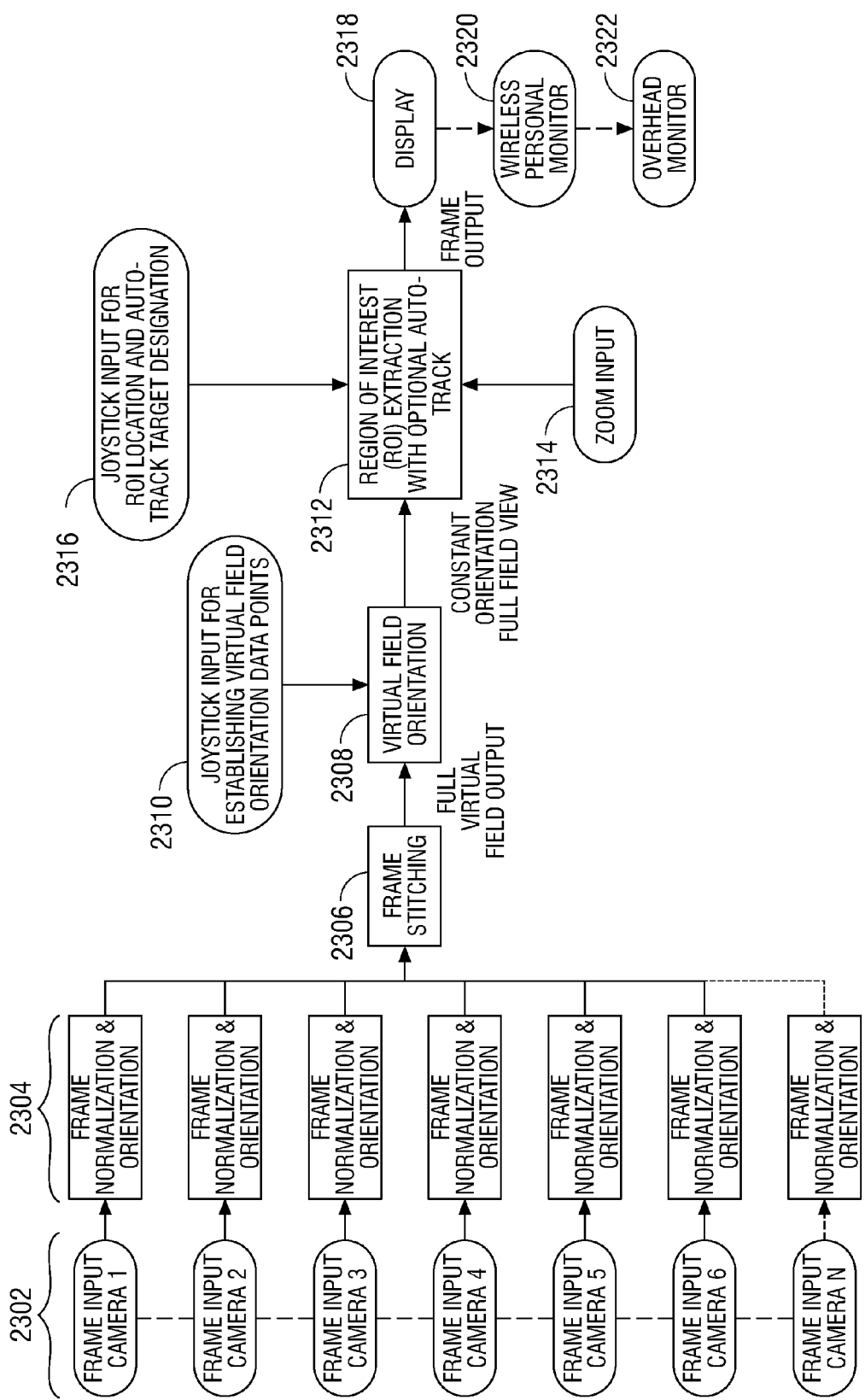
FIG. 24 illustrates a flowchart of a video processing program, the steps of which are performed during the operation of the surgical device in accordance with one example embodiment of the present invention.

FIG. 24 illustrates a flowchart of a video processing program, the steps of which are performed during the operation of the surgical device in accordance with one example embodiment of the present invention. According to one example embodiment of the present invention, the video processing routine may be stored in and executed by, e.g., the processor 1161d shown in FIG. 10. However, it should be understood that other controllers, electronic devices, etc. may be configured to execute some or all of the steps illustrated in FIG. 24.

In step 2302, at least two image sensors, such as image sensors 1510a to 1510f illustrated in FIG. 22, provide image data in the form of an image frame. In step 2302, the image frames from each image sensor, such as the image frames 5401 to 5406 from the image sensors 1540a to 1540f, respectively, are provided as input to the video processor. For the purposes of example only, the flowchart of FIG. 24 is explained hereinbelow as being performed by the processor 1161d shown in FIG. 10, although it should be recognized that any video processor that is configured to perform the steps described hereinbelow may be employed in the present invention.

In step 2304, the processor 1161d performs a frame normalization procedure. More specifically, the processor 1161d normalizes the image frames, e.g., the image frames 5401 to 5406, received from each of the image sensors, e.g., 1540a to 1540f, respectively, by adjusting, if necessary, the image frames so as to be of the same size relative to each other. In addition, in step 2304, the processor 1161d performs a frame orientation procedure. More specifically, the processor 1161d orients the image frames, e.g., the image frames 5401 to 5406, received from each of the image sensors, e.g., 1540a to 1540f, respectively, by rotating, if necessary, the image frames so as to be similarly oriented relative to each other.

In step 2306, the processor 1161d performs a frame stitching procedure. More specifically, the processor 1161d stitches together the normalized and oriented image frames, e.g., the image frames 5401 to 5406, received from each of the image sensors, e.g., 1540a to 1540f, respectively. According to one embodiment, the processor 1161d performs the frame stitching procedure of step 2306 by identifying those portions, e.g., pixels, of the image frames 5401 to 5406 that are in common with each other, e.g., those portions of the image frames 5401 to 5406 that overlap relative to each other. One example of a frame stitching procedure that may be employed by the processor 1161d is set forth in additional detail below in connection with the flow chart illustrated in FIG. 26(c).

After performing the frame stitching procedure of step 2306, the processor 1161d then generates in step 2308 a full virtual field of view, such as the composite image 5407 illustrated in FIG. 23. Furthermore, at step 2308, the processor 1161d may be configured to perform an image stabilization procedure. The image stabilization procedure is advantageously performed in order to stabilize the image displayed to the user such that movement of the image sensors 1114a to 1114d, e.g., rotation in a first direction, does not result in a corresponding change, e.g., a rotation in a second direction in the image that is displayed to and viewed by the user. One example of a stabilization procedure that may be employed by the processor 1161d is set forth in additional detail below in connection with the flow chart illustrated in FIG. 25(c).

In step 2310, a user input device, such as the remote control unit 1147 illustrated in FIG. 19, may be employed in order to generate control signals, e.g., control signals 1148, that are received by the processor 1161d and that the processor 1161d employs to establish or adjust orientation data points for the composite image 5407. For instance, an operator may employ, e.g., a joystick or other control device, so as to establish or adjust the orientation of the composite image 5407 by moving one or more of the image sensors 1540. In the event that a user input device, e.g., the remote control unit 1147, is employed in order to establish or adjust orientation data points for the composite image 5407 in step 2310, the processor 1161d may re-perform step 2308 so as to again generate a full virtual field of view, such as a new composite image 5407, in accordance with the orientation data points that were established or adjusted in step 2310. The processor 1161d thereby insures via step 2308 that the composite image 5407 remains properly oriented regardless of, for instance, a movement or reorientation of the image sensors.

The processor 1161d may then selectively generate in step 2312 a region of interest corresponding to a portion of the full virtual field of view, e.g., a portion of the composite image 5407. In step 2316, a user input device, such as the remote control unit 1147, may be employed in order to generate control signals, e.g., control signals 1148, that are received by the processor 1161d and that the processor 1161d employs to select a portion of the composite image 5407. For instance, an operator may employ, e.g., a joystick or other control device, so as to selectively display a desired portion of the composite image 5407, e.g., the image frame of one or more of the image sensors 1540. In one embodiment, the processor 1161d also has an optional auto-track feature. According to this embodiment, in step 2316, the processor 1161d is configured to automatically adjust the region of interest selected by a user. In this manner, the region of interest originally selected by a user in step 2316 may be adjusted so as to, e.g., continue displaying a surgical instrument as the surgical instrument is moved within the abdominal cavity 1501.

In still another embodiment, a user input device, such as the remote control unit 1147, may be employed in order to zoom into or out of a portion of the composite image 5407. For instance, an operator may employ, e.g., a joystick or other control device, to generate control signals, e.g., control signals 1148, that are received by the processor 1161d and that the processor 1161d may employ to selectively zoom into or out of a desired portion of the composite image 5407. According to this embodiment, in step 2314, the processor 1161d is configured to automatically adjust the region of interest selected by a user in accordance with signals provided by an operator.

In step 2318, the processor 1161d generates a display, e.g., for viewing by an operator. Of course, the image that is displayed in step 2318 may be, e.g., the composite image 5407 of the entire abdominal cavity generated in step 2308, a region of interest of the composite image 5407 corresponding to a selected portion of the abdominal cavity as generated in step 2312, a zoomed image etc. In step 2318, the image may be displayed on any suitable display device, for instance in step 2320 on a wireless personal display monitor such as the wireless video display device 1150 illustrated in FIG. 19, in step 2332 on an overhead display monitor such as the wired video display device 145 illustrated in FIG. 1, etc.

Figure 25A:
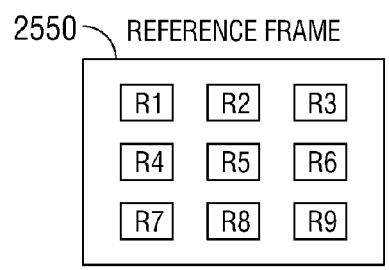
FIG. 25(*a*) illustrates a reference image frame according to one example embodiment of the present invention.
Figure 25B:
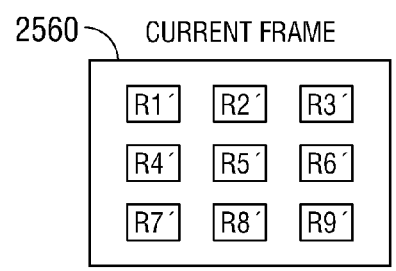
Figure 25C:
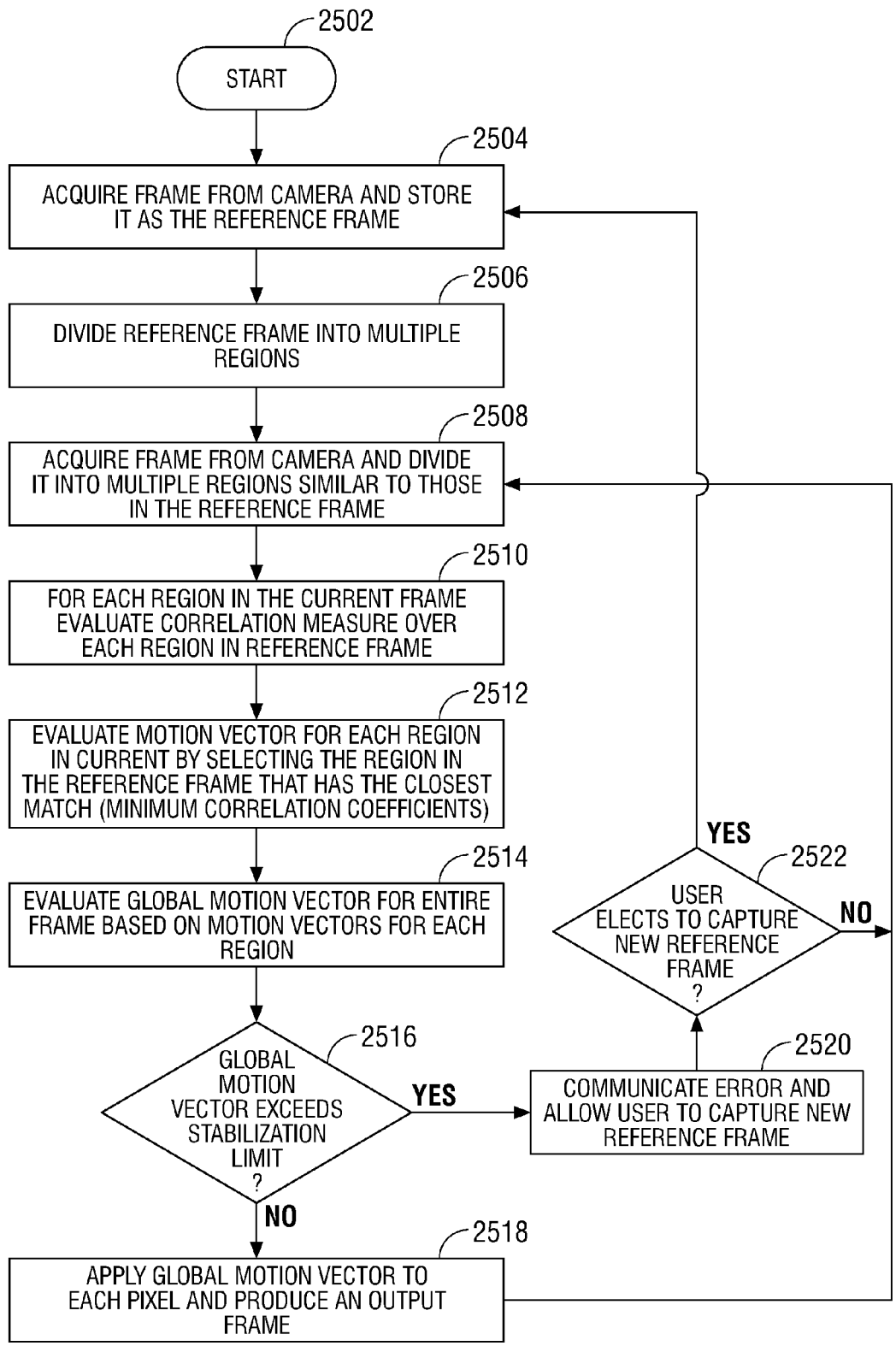

As previously mentioned, FIG. 25(c) is a flow chart that illustrates, according to one example embodiment of the present invention, a frame stabilization procedure that may be employed by the processor 1161d. At step 2502, the processor 1161d starts the frame stabilization process. At step 2504, the processor 1161d acquires an image frame, e.g., image frame 5401, from an image sensor, e.g., image sensor 540a, and stores the image frame 5401 as a reference image frame 2550. For instance, FIG. 25(a) illustrates a reference image frame 2550 according to one example embodiment of the present invention.

Referring back to FIG. 25(c), at step 2506, the processor 1161d divides the reference image frame 2550 into a plurality of image regions. For instance, FIG. 25(a) illustrates the reference image frame 2550 divided into nine reference image regions, designated as reference image regions R1 through R9. It should be understood that, FIG. 25(a) illustrates the reference image frame 2550 divided into nine reference image regions, in other embodiments, the reference image frame 2550 may be divided into any number of reference image regions.

At step 2508, the processor 1161d acquires a current image frame, e.g., image frame 5401, from an image sensor, e.g., image sensor 540a. For instance, FIG. 25(b) illustrates a current image frame 2560 according to one example embodiment of the present invention. In addition, at step 2508, the processor 1161d divides the current image frame 2560 into a plurality of current image regions. Advantageously, the processor 1161d divides the current image frame 2560 into a plurality of current image regions that are generally similarly disposed relative to the reference image regions into which the reference image frame 2550 was divided at step 2506. For instance, FIG. 25(b) illustrates the current image frame 2560 divided into nine current image regions, designated as image regions R1' through R9'.

At step 2510, the processor 1161d evaluates, for each region in the current image frame 2560, a correlation measurement relative to each region in the reference image frame 2550. At step 2512, the processor 1161d evaluates a motion vector for each current image region in the current image frame 2560. Preferably, the processor 1161d performs this evaluation by selecting, for each current image region in the current image frame 2560, the reference image region in the reference image frame 2550 that has the closest match, e.g., the minimum number of correlation co-efficients relative to the current image region in the current image frame 2560.

At step 2514, the processor 1161d evaluates a global motion vector corresponding to the entire current image frame 2560. Preferably, the processor 1161d evaluates the global motion vector corresponding to the entire current image frame 2560 such that the global motion vector is based on the individual motion vectors determined at step 2512 for each current image region in the current image frame 2560.

At step 2516, the processor 1161d determines whether the global motion vector determined at step 2514 exceeds a predetermined stabilization value. If the processor 1161d determines at step 2516 that the global motion vector does not exceed the predetermined stabilization value, then the processor 1161d proceeds to step 2518. At step 2518, the processor 1161d applies the global motion vector determined at step 2514 to each pixel of the current image frame 2560. In addition, at step 2518, the processor 1161d produces, from the pixels of the current image frame 2560 that have had applied thereto the global motion vector, an output frame. The output frame is, for instance, the image that is displayed to the user. The processor 1161d returns to step 2508 so as to acquire a new current image frame 2560 and to repeat the subsequent steps 2510, 2512, etc.

If the processor 1161d determines at step 2516 that the global motion vector does exceed the predetermined stabilization value, then the processor 1161d proceeds to step 2520. At step 2520, the processor 1161d communicates the stabilization error, for instance by providing an error message to the user. In addition, at step 2520, the processor 1161d provides to the user an opportunity to capture a new reference image frame 2550.

At step 2522, the processor 1161d determines whether user elected at step 2520 to capture a new reference image frame 2550. If the processor 1161d determines at step 2522 that the user did not elect to capture a new reference image frame 2550, then the processor 1161d returns to step 2508 so as to acquire a new current image frame 2560 and to repeat the subsequent steps 2510, 2512, etc. If the processor 1161d determines at step 2522 that the user did elect to capture a new reference image frame 2550, then the processor 1161d returns to step 2504 so as to acquire a new reference image frame 2560 and to repeat the subsequent steps 2506, 2508, etc.

Additional methods for performing a frame stabilization procedure may be employed by the processor 1161d. For instance, according to one example embodiment of the present invention, the processor 1161d is configured to perform the image stabilization procedure described in "Implementing a Gray-Code Bit-Plane Matching Image Stabilization Algorithm on a Xilinx FPGA", Allen et al., which is expressly incorporated herein by reference in its entirety. According to another example embodiment of the present invention, the processor 1161d is configured to perform the image stabilization procedure described in "Digital Image Stabilization", Samsung Electronics Co., 1997, which is also expressly incorporated herein by reference in its entirety.

Figure 26A:
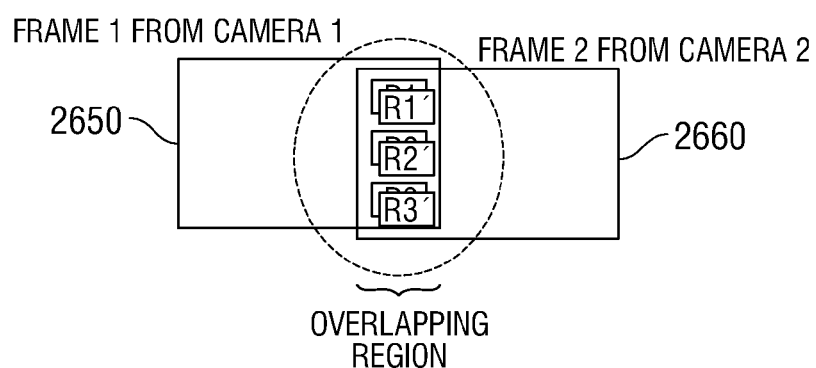
FIG. 26(*a*) illustrates a first image frame that overlaps with a second image frame, according to one example embodiment of the present invention.
Figure 26B:
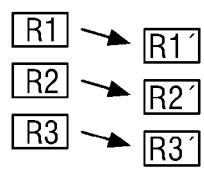
Figure 26C:
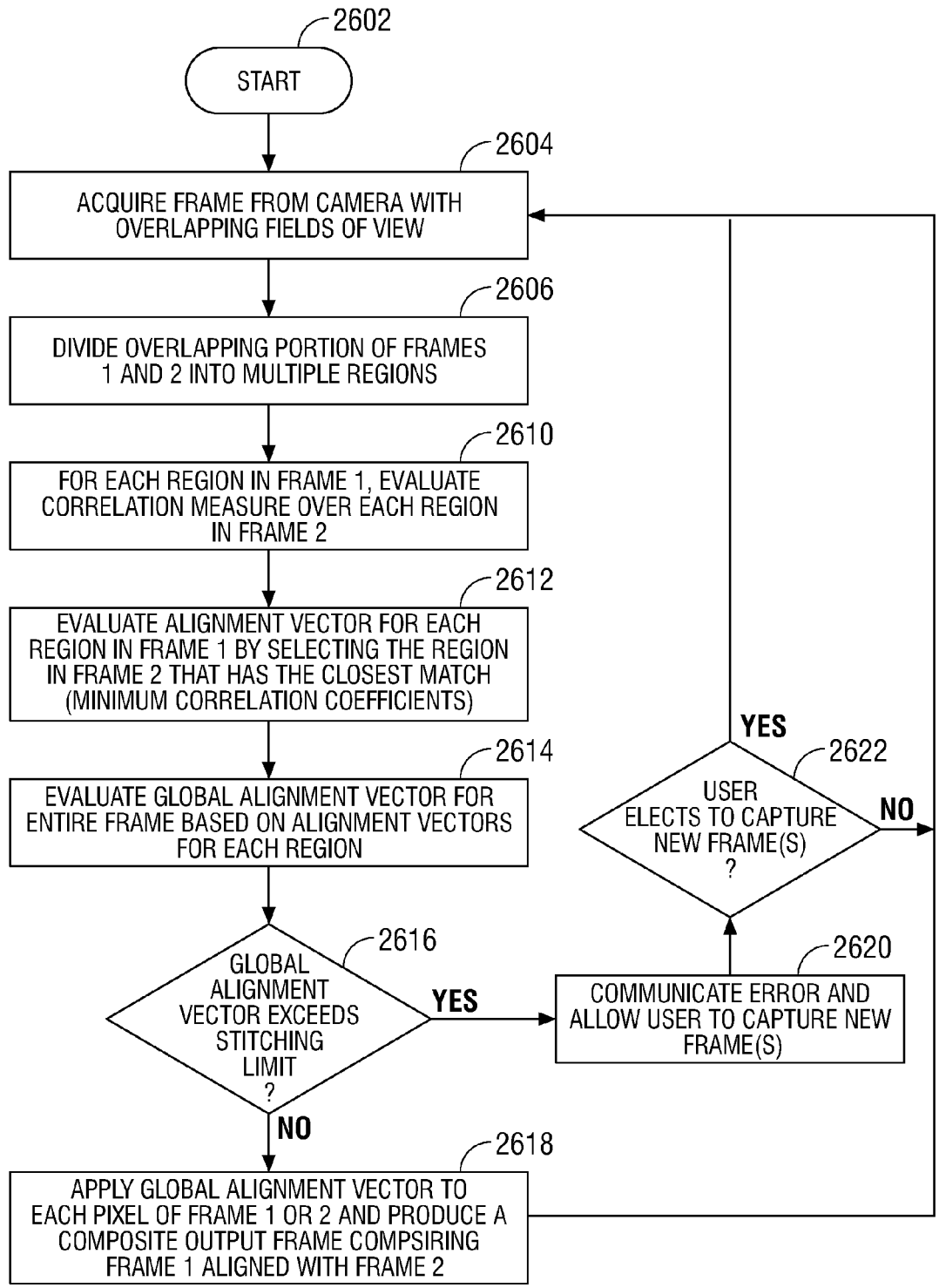

As previously mentioned, FIG. 26(c) is a flow chart that illustrates, according to one example embodiment of the present invention, a frame stitching procedure that may be employed by the processor 1161d. At step 2602, the processor 1161d starts the frame stitching process. At step 2604, the processor 1161d acquires an image frame from each image sensor, e.g., camera, having overlapping fields of view. For instance, the processor 1161d may acquire a first image frame from a first camera and a second image frame from a second camera. FIG. 26(a) illustrates a first image frame 2650 that overlaps with a second image frame 2660, according to one example embodiment of the present invention.

Referring back to FIG. 26(c), at step 2606, the processor 1161d divides the overlapping portions of the first image frame 2650 and the second image frame 2660 into a plurality of overlap image regions. For instance, FIG. 26(a) illustrates that, in the overlapping portions of the first image frame 2650 and the second image frame 2660, the first image frame 2650 is divided into three overlap image regions, designated as first overlap image regions R1 through R3, while the second image frame 2660 is divided into three overlap image regions, designated as second overlap image regions R1' through R3'. It should be understood that, while FIG. 26(a) illustrates the overlapping portions of each of the first image frame 2650 and the second image frame 2660 divided into three overlap image regions, in other embodiments, the overlapping portions of each of the first image frame 2650 and the second image frame 2660 may be divided into any number of overlap image regions.

At step 2610, the processor 1161d evaluates, for each overlap image region in the first image frame 2650, a correlation measurement relative to each overlap image region in the second image frame 2660. At step 2612, the processor 1161d evaluates an alignment vector for each overlap image region in the first image frame 2660. Preferably, the processor 1161d performs this evaluation by selecting, for each overlap image region in the first image frame 2560, the overlap image region in the second image frame 2550 that has the closest match, e.g., the minimum number of correlation coefficients relative to the overlap image region in the first image frame 2650.

At step 2614, the processor 1161d evaluates a global alignment vector corresponding to the entire second image frame 2660. Preferably, the processor 1161d evaluates the global alignment vector corresponding to the entire second image frame 2660 such that the global alignment vector is based on the individual alignment vectors determined at step 2612 for each second image region in the second image frame 2660.

At step 2616, the processor 1161d determines whether the global alignment vector determined at step 2614 exceeds a predetermined stitching value. If the processor 1161d determines at step 2616 that the global alignment vector does not exceed the predetermined stitching value, then the processor 1161d proceeds to step 2618. At step 2618, the processor 1161d applies the global alignment vector determined at step 2614 to each pixel of either the first or the second image frame 2650, 2660. In addition, at step 2618, the processor 1161d produces, from the pixels of either the first or second image frame 2560, 2660 that have had applied thereto the global alignment vector, a composite output frame. The composite output frame includes the first image frame 2560 aligned with the second image frame 2660. The composite output frame may be displayed to the user. The processor 1161d then returns to step 2604 so as to acquire an image frame from each camera having overlapping fields of view and to repeat the subsequent steps 2510, 2512, etc.

If the processor 1161d determines at step 2616 that the global alignment vector does exceed the predetermined stitching value, then the processor 1161d proceeds to step 2620. At step 2620, the processor 1161d communicates the stitching error, for instance by providing an error message to the user. In addition, at step 2620, the processor 1161d provides to the user an opportunity to capture new first and second image frames 2650, 2660.

At step 2622, the processor 1161d determines whether the user elected at step 2620 to capture new first and second image frames 2650, 2660. If the processor 1161d determines at step 2622 that the user did not elect to capture new first and second image frames 2650, 2660, then the processor 1161d returns to step 2604 so as to acquire an image frame from each camera having overlapping fields of view and to repeat the subsequent steps 2606, 2608, etc. If the processor 1161d determines at step 2622 that the user did elect to capture new first and second image frames 2650, 2660, then the processor 1161d returns to step 2604 so as to acquire an image frame from each camera having overlapping fields of view and to repeat the subsequent steps 2606, 2608, etc.

As set forth more fully above, it is typically important that during a surgical operation a surgeon be able to view a surgical site, and the instruments that are employed within a surgical site, in order to insure that the surgical procedure is performed correctly. The present invention also contemplates various embodiments that accomplish the objective in connection with surgical instruments such as surgical staplers and the like. FIGS. 27(a) to 27(e) are a series of side cross-sectional views that illustrate various portions of a circular cutting/stapling device 2800 having an off-axis image system, according to one example embodiment of the present invention. FIGS. 28(a) to 28(e), on the other hand, are a series of side cross-sectional views that illustrate various portions of a circular cutting/stapling device 2900 having an on-axis image system, according to another example embodiment of the present invention.

Figure 27A:
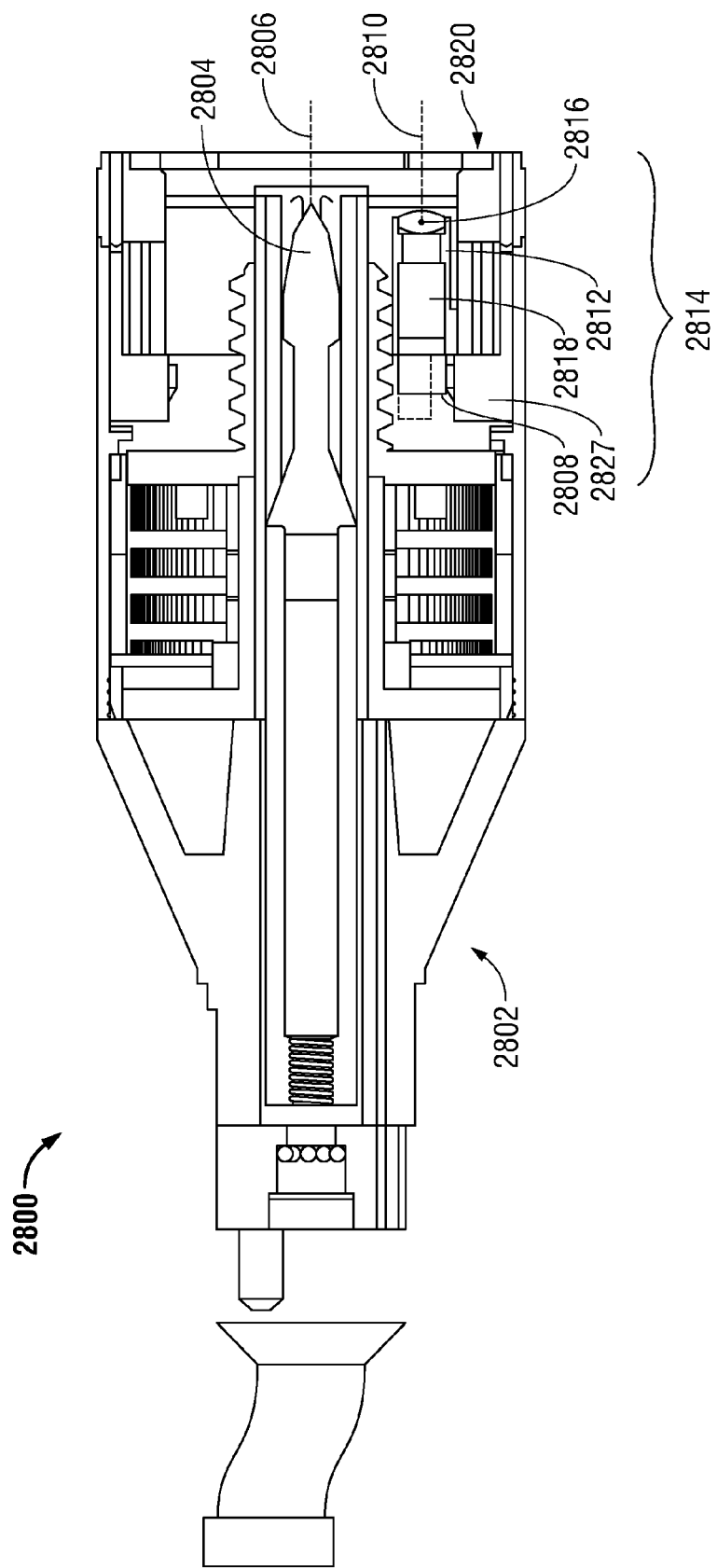
FIGS. 27(*a*) to 27(*e*) are side cross-sectional views that illustrate various portions of a circular cutting/stapling device having an "off-axis" image system, according to one example embodiment of the present invention.

Referring to FIG. 27(a), there is shown a side cross-sectional view that illustrates a DLU portion 2802 of a surgical device 2800, e.g., a circular cutting/stapling device such as may be employed in an anastomosing surgical procedure. The DLU portion 2802 includes a trocar 2804 which is axially moveable relative to the DLU portion 2802 along a central axis 2806, for instance by operation of a first rotatable drive shaft driven by the electromechanical driver device 110 and housed within the flexible shaft 170 illustrated in FIG. 13. FIG. 27(a) illustrates the trocar 2804 in a retracted position within the DLU portion 2802.

The DLU portion 2802 also includes a first image sensor portion 2808. The first image sensor portion 2808 is positioned within the DLU portion 2802 along a second axis 2810. The second axis 2810 is different from the central axis 2806, e.g., off-axis. The first image sensor portion 2808 includes a housing 2812 having an opening at its distal end. Within the housing 2812 is positioned an image capture arrangement 2814. According to one embodiment of the present invention, the image capture arrangement 2814 may include a first lens 2816 and an image sensor 2818, e.g., a camera, positioned behind the opening of the housing 2812. Advantageously, the first image sensor portion 2808 is positioned within the DLU portion 2802 such that it is axially recessed relative to a clamping surface 2820 of the DLU portion 2802. The image capture arrangement 2814 may be configured to generate image data in accordance with an image and to communicate the image data to a processor, e.g., the circuit arrangement 320 shown in FIG. 3(b) via a data transmission cable, e.g., the data bus 430 shown in FIG. 4(b).

It should be recognized that, while FIG. 27(a) illustrates the image sensor 2818 being positioned directly behind the first lens 2816, in other embodiments, the image sensor 2818 may be arranged in a position remote from the first lens 2816, with light from the first lens 2816 being transmitted to the image sensor 2818 via, for example, fiber optic connections. In one exemplary embodiment, the image sensor 2818 is positioned in the DLU portion 2802. In another exemplary embodiment, the image sensor 2818 is positioned in a shaft, e.g., the flexible shaft 170 shown in FIG. 1, in a coupling thereto, e.g., the first coupling 175 and/or the second coupling 185 shown in FIG. 1, and/or in a driver device, e.g., the electromechanical driver device 110 shown in FIG. 1. In any event, image data may be transmitted to the driver device, e.g., the electromechanical driver device 110 shown in FIG. 1, via a wireless or wired connection. The surgical device 2800 may also include a cleaning system 2827. The cleaning system 2827 may be configured to clean the image sensor 2818 and/or the first lens 2816.

Figure 27B:
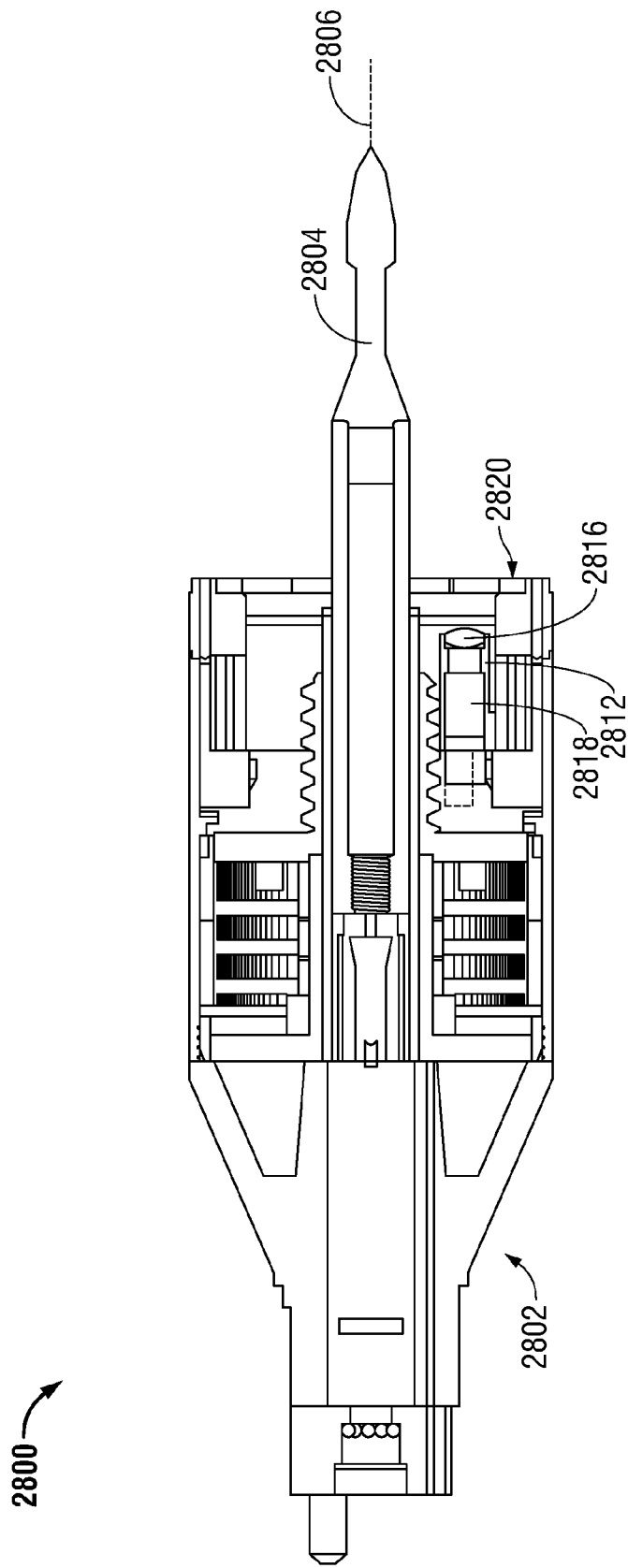

FIG. 27(b) is a side cross-sectional view that illustrates the DLU portion 2802 of a surgical device 2800. In FIG. 27(b), the trocar 2804 is axially advanced in a distal direction along a central axis 2806, so as to be in an extended position within the DLU portion 2802.

Figure 27C:
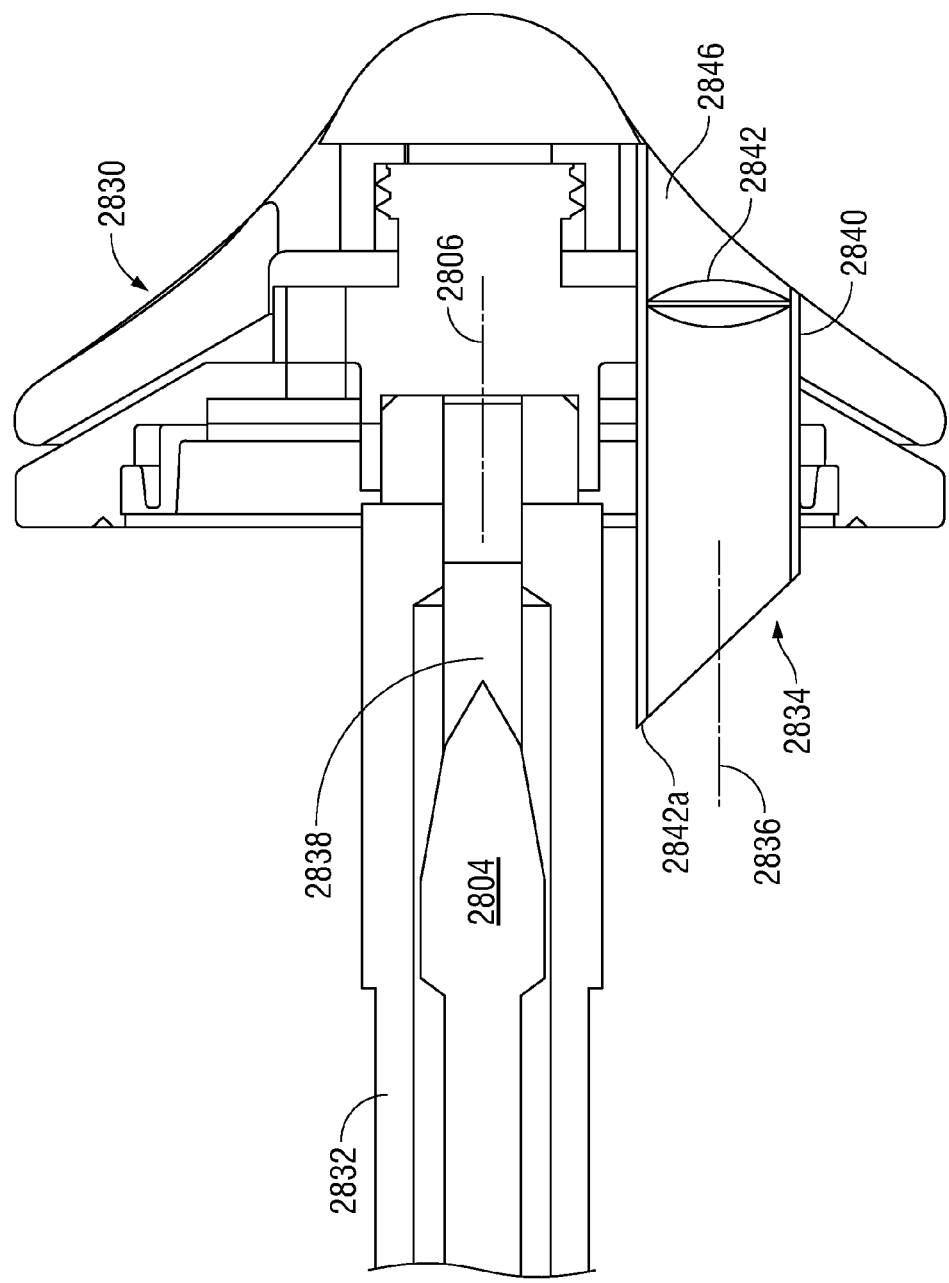

FIG. 27(c) is a side cross-sectional view that illustrates an anvil portion 2830 that is mounted on the DLU portion 2802 of the surgical device 2800. Specifically, the anvil portion 2830 is mounted via a trocar receiving sleeve 2832 on the DLU portion 2802 so as to be axially fixed relative to the trocar 2804, and so as to be axially moveable relative to the DLU portion 2802 along a central axis 2806 when the trocar 2804 is moved between the retracted and the extended positions. FIG. 27(c) illustrates the trocar 2804 and the anvil portion 2832 in the extended position relative to the DLU portion 2802.

The anvil portion 2830 also includes a second image sensor portion 2834. The second image sensor portion 2834 is positioned within the anvil portion 2830 along a third axis 2836. The third axis 2836 is different from the central axis 2806, e.g., off-axis. In the preferred embodiment, DLU portion 2802 and the anvil portion 2830 are configured so as to have an alignment mechanism 2838, e.g., corresponding keys and/or keyways, slots, etc., such that, when the anvil portion 2830 is mounted via a trocar receiving sleeve 2832 on the trocar 2804 of the DLU portion 2802, the third axis 2836 is aligned with the second axis 2810.

The second image sensor portion 2834 includes a tube 2840. Within the tube 2840 is positioned a second lens 2842. According to one embodiment of the present invention, the tube 2840 has a sharp end 2842a that extends in the proximal direction. The cleaning system 2827 shown in FIG. 27(a) may also be configured to clean the second lens 2842. Advantageously, the tube 2840 has an inner diameter that corresponds to, e.g., is slightly larger than, an outer diameter of the housing 2812 of the first image sensor portion 2808 in the DLU portion 2802. The tube 2840 extends through the anvil portion 2830 so as to enable light to be conveyed from a distal end of the tube 2840, e.g., through an opening 2846 in the anvil, through the second lens 2842 and through the proximal sharp end 2842a of the tube 2840.

Figure 27D:
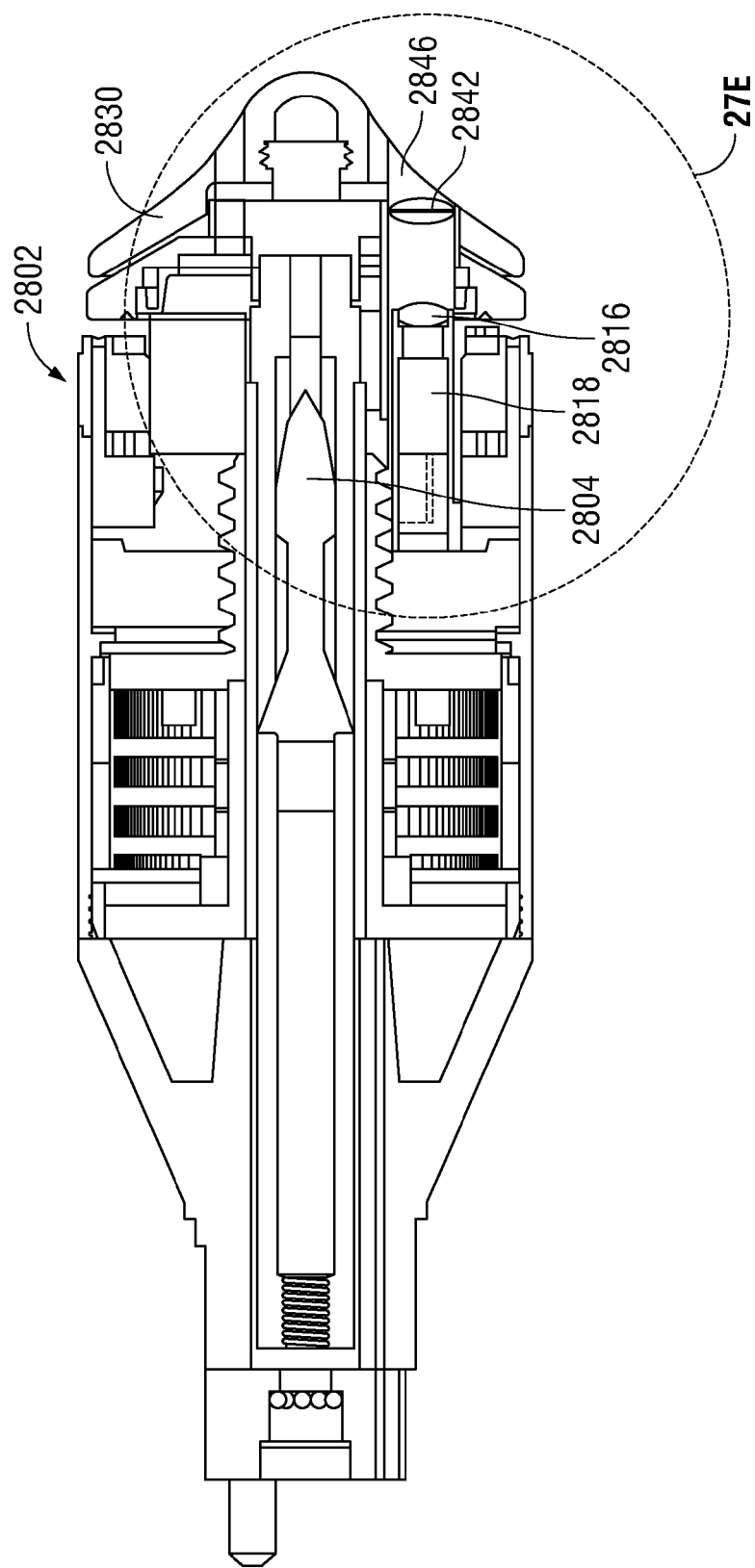
Figure 27E:
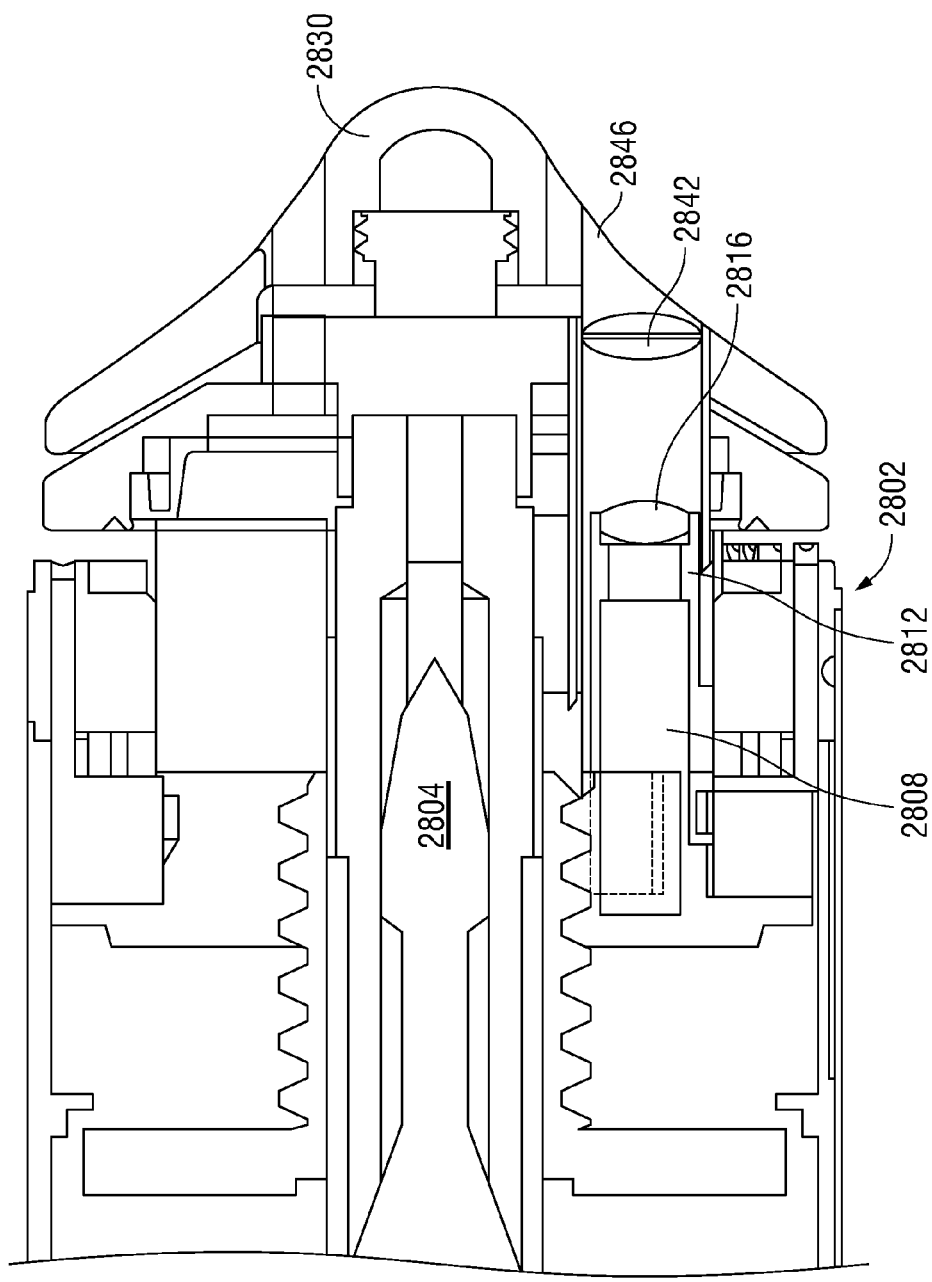

FIG. 27(d) is a side cross-sectional view that illustrates the trocar 2804 and the anvil portion 2830 in the retracted position relative to the DLU portion 2802. FIG. 27(e) is a side cross-sectional view that illustrates the trocar 2804 and the anvil portion 2832 in the retracted position relative to the DLU portion 2802 as shown in FIG. 27(d) but in greater detail. As illustrated in FIG. 27(e), the anvil portion 2830 is retracted relative to, e.g., so as to be adjacent to, the DLU portion 2802. In this position, the tube 2840 of the anvil portion 2830 surrounds the housing 2812, and the first lens 2816 of the first image sensor portion 2808 is aligned with the second lens 2842 of the second image sensor portion 2834.

In operation, the trocar 2804 is initially retracted to the position illustrated in FIG. 27(a) so as to enable the DLU portion to be inserted into a body of a patient, e.g., a gastrointestinal tract. The trocar 2804 is then extended into the position illustrated in FIG. 27(b), and the trocar 2804 is used to puncture a closed section of the gastrointestinal tract. The anvil portion 2830 is positioned within a second, adjoining section of the gastro-intestinal tract, and the trocar 2804 is inserted within the trocar receiving sleeve 2832 of the anvil portion 2830 so as to mount the anvil portion 2830 to the trocar 2804. The alignment mechanism 38 ensures that the DLU portion 2802 is rotationally aligned relative to the anvil portion 2830. The trocar 2804 is then retracted until the anvil portion 2830 is approximately adjacent to the clamping surface 2820 of the DLU portion 2802. In this position, tissue of the gastrointestinal tract is clamped between the anvil portion 2830 and the clamping surface 2820 of the DLU portion 2802. While the trocar 2804 is being retracted relative to the DLU portion 2802, the sharp end 2842a of the tube 2842 punctures the tissue of the gastro-intestinal tract that is clamped between the anvil portion 2830 and the clamping surface 2820 of the DLU portion 2802. The cleaning system 2827 may be employed, either automatically or manually, to clean the image sensor 2816, the first lens 2818 and the second lens 2842 of blood or other bodily fluids or tissue that result from the puncturing of the section of tissue with sharp end 2842a of the tube 2842.

As the trocar 2804 is further retracted relative to the DLU portion 2802, the tube 2840 of the anvil portion 2830 slides over the housing 2812 of the first image sensor portion 2808 such that the first lens 2816 of the first image sensor portion 2808 is aligned with the second lens 2842 of the second image sensor portion 2834. In this manner, light, e.g., an image, is conveyed from a distal end of the tube 2840, e.g., through an opening 2846 in the anvil, through the second lens 2842, towards the proximal sharp end 2842a of the tube 2840, through the first lens 2816 and to the image sensor 2818. The image sensor 2818 of the image capture arrangement 2814 may then generate image data corresponding to the image and communicate the image data for further processing to a processor, e.g., the circuit arrangement 320 shown in FIG. 3(b) via a data transmission cable, e.g., the data bus 430 shown in FIG. 4(b).

The surgical device 2800 illustrated in FIGS. 27(a) to 27(e) provides an arrangement that enables a user to view the a surgical site without first removing the surgical device 2800 from the surgical site. For instance, in accordance with the above-described embodiment of the invention, a surgeon may perform an anastomosing procedure by clamping and stapling a section of tissue between the anvil portion 2830 and the DLU portion 2802 of the surgical device 2800. The surgeon may then view the integrity of the stapled section of tissue via the image sensor 2818, which is configured to provide an image of the surgical site through the tube 2840, without the need to remove the surgical device 2800 from the surgical site. To obtain a full view of the surgical site, e.g., the staple line, the DLU portion 2802 may be rotated within the surgical site, depending, e.g., on the geometry of the anvil portion 2830. The surgical device 2800 illustrated in FIGS. 27(a) to 27(e) also provides an advantage in that many of the components of the surgical device 2800 are similar or common to components that may be employed in a surgical device without such an optics/imaging system, thereby promoting interchangability of parts between such surgical devices.

Figure 28A:
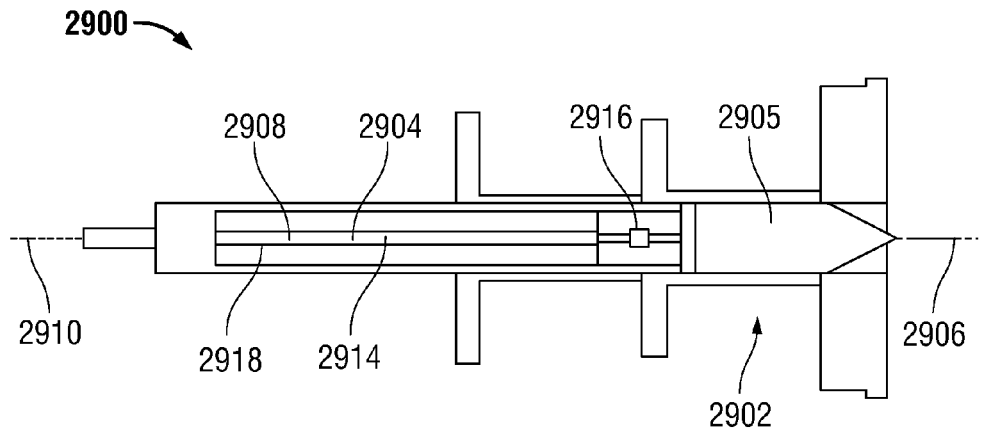
FIGS. 28(*a*) to 28(*e*) are side cross-sectional views that illustrate various portions of a circular cutting/stapling device having an "on-axis" image system, according to another example embodiment of the present invention.

As previously mentioned, FIGS. 28(a) to 28(e) are a series of side cross-sectional views that illustrate various portions of a circular cutting/stapling device 2900 having an "on-axis" image system, according to another example embodiment of the present invention. Referring to FIG. 28(a), there is shown a side cross-sectional view that illustrates a DLU portion 2902 of a surgical device 2900, e.g., a circular cutting/stapling device such as may be employed in an anastomosing surgical procedure. The DLU portion 2902 includes a trocar extension 2904 onto which is mounted a trocar head 2905. Preferably, the trocar head 2905 is removably mounted onto the trocar extension 2904. The trocar extension 2904, and thus the trocar head 2905 mounted thereon, are axially moveable relative to the DLU portion 2902 along a central axis 2906, for instance by operation of a first rotatable drive shaft driven by the electromechanical driver device 110 and housed within the flexible shaft 170 illustrated in FIG. 13. FIG. 28(a) illustrates the trocar extension 2904 and the trocar head 2905 in a retracted position within the DLU portion 2902.

The trocar extension 2904 is at least partially hollow and has an opening at its distal end. In addition, the trocar head 2905 has a bore extending therethrough in the axial direction. By virtue of its at least partially hollow interior, the trocar extension 2904 may include therewithin a first image sensor portion 2908. The first image sensor portion 2908 is positioned within the trocar extension 2904 along a second axis 2910. Preferably, the second axis 2910 coincides with, e.g., is coaxial relative to, the central axis 2906, e.g., "on-axis". The first image sensor portion 2908 includes an image capture arrangement 2914. According to one embodiment of the present invention, the image capture arrangement 2914 may include a first lens 2916 and an image sensor 2918, e.g., a camera. The image capture arrangement 2914 may be configured to generate image data in accordance with an image and to communicate the image data to a processor, e.g., the circuit arrangement 320 shown in FIG. 3(b) via a data transmission cable, e.g., the data bus 430 shown in FIG. 4(b).

It should be recognized that, while FIG. 28(a) illustrates the image sensor 2918 being positioned directly behind the first lens 2916, in other embodiments, the image sensor 2918 may be arranged in a position remote from the first lens 2916, with light from the first lens 2916 being transmitted to the image sensor 2918 via, for example, fiber optic connections. In one exemplary embodiment, the image sensor 2918 is positioned in the trocar extension 2904. In another exemplary embodiment, the image sensor 2918 is positioned in a shaft, e.g., the flexible shaft 170 shown in FIG. 1, in a coupling thereto, e.g., the first coupling 175 and/or the second coupling 185 shown in FIG. 1, and/or in a driver device, e.g., the electromechanical driver device 110 shown in FIG. 1. In any event, image data may be transmitted to the driver device, e.g., the electromechanical driver device 110 shown in FIG. 1, via a wireless or wired connection.

Figure 28B:
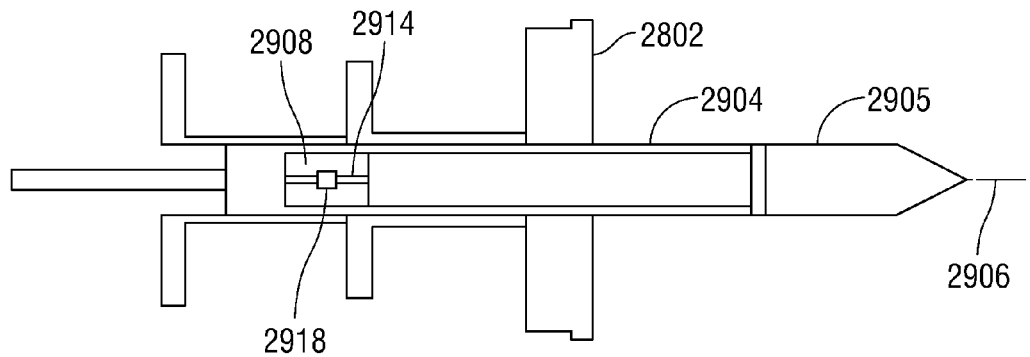
Figure 28C:
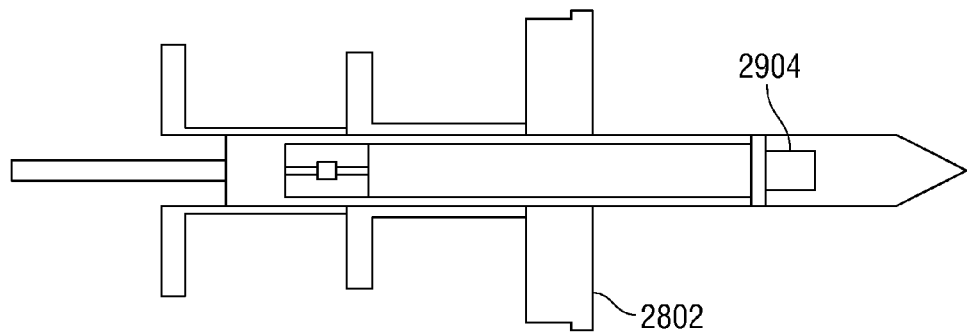

FIG. 28(b) is a side cross-sectional view that illustrates the DLU portion 2902 of a surgical device 2900. In FIG. 28(c), the trocar extension 2904, onto which is mounted the trocar head 2905, is axially advanced in a distal direction along a central axis 2906, so as to be in an extended position relative to the DLU portion 2902. In FIG. 28(c), the trocar head 2905 is removed from the distal end of the trocar extension 2904.

Figure 28D:
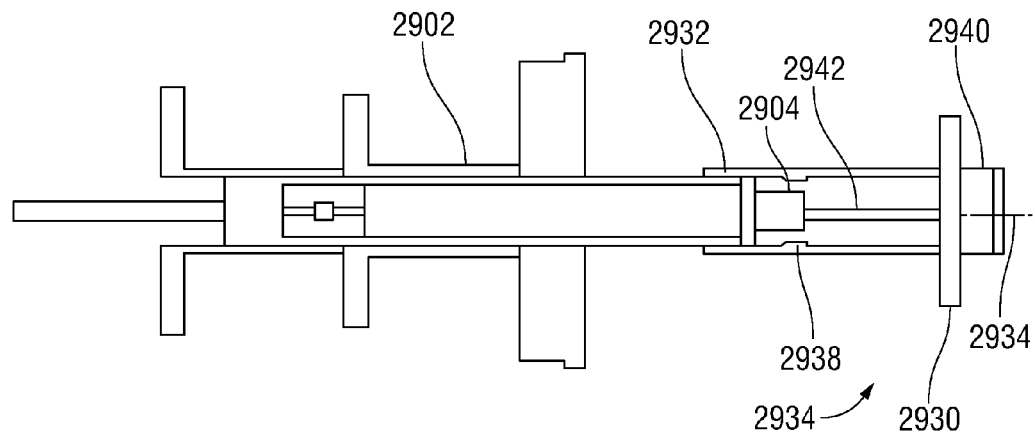
Figure 28E:
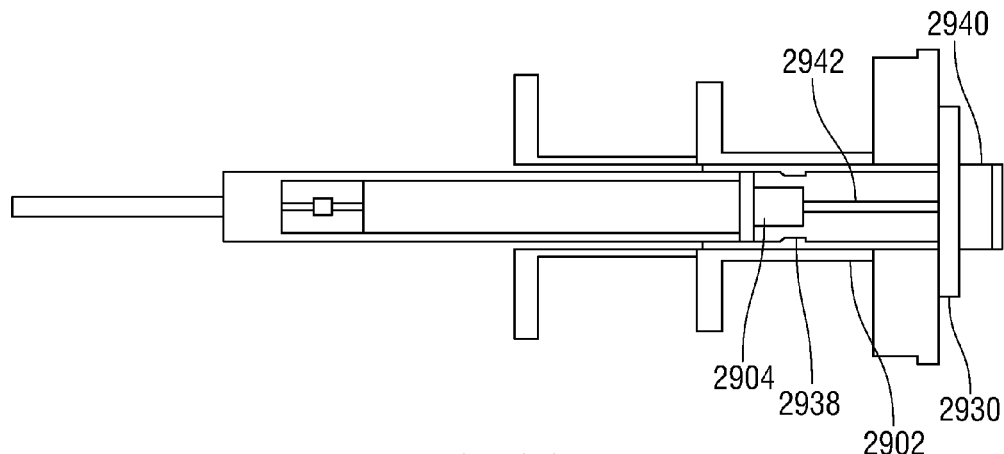

FIG. 28(d) is a side cross-sectional view that illustrates an anvil portion 2930 being mounted on the DLU portion 2902 of the surgical device 2900. Specifically, the anvil portion 2930 is mounted via a trocar receiving sleeve 2932 on the trocar 2904 so as to be axially fixed relative to the trocar 2904, and so as to be axially moveable relative to the DLU portion 2902 along the central axis 2906 when the trocar 2904 is moved between the retracted and the extended positions. FIG. 28(d) illustrates the trocar 2904 and the anvil portion 2932 in the extended position relative to the DLU portion 2902.

The anvil portion 2930 also includes a second image sensor portion 2934. The second image sensor portion 2934 is positioned within a centrally-disposed and axially-extending bore 2940 defined by the anvil portion 2930. Preferably, the bore 2940 defines a third axis 2936, which coincides with, e.g., is coaxial relative to, the central axis 2906, e.g., "on-axis".

The second image sensor portion 2934 includes within the bore 2940 a second lens 2942. Advantageously, the tube 2940 has an inner diameter that corresponds to, e.g., is slightly larger than, an outer diameter of the trocar extension 2904 of the DLU portion 2902. The inner diameter of the tube 2940 and the outer diameter of the trocar extension 2904 of the DLU portion 2902 advantageously have corresponding engagement mechanisms 2938 which enable the anvil portion 2930 to be mounted to and axially fixed in position relative to the trocar extension 2904. The bore 2940 extends through the anvil portion 2930 so as to enable light to be conveyed from a distal end of the bore 2940, through the second lens 2942 and through the proximal end of the tube 2940.

FIG. 28(*e*) is a side cross-sectional view that illustrates the trocar extension 2904 and the anvil portion 2930 in the retracted position relative to the DLU portion 2902. As illustrated in FIG. 28(*e*), the anvil portion 2930 is retracted relative to, e.g., generally adjacent to, the DLU portion 2902.

In operation, the trocar extension 2904, with the trocar head 2905 mounted thereon, is initially retracted to the position illustrated in FIG. 28(*a*) so as to enable the DLU portion 2902 to be inserted into a body of a patient, e.g., a gastrointestinal tract. The trocar extension 2904 and the trocar head 2905 are then extended into the position illustrated in FIG. 28(*b*), and the trocar head 2905 is used to puncture a closed section of the gastro-intestinal tract. The trocar head 2905 is then removed from the distal end of the trocar extension 2904. The anvil portion 2930 is positioned within a second, adjoining section of the gastro-intestinal tract, and the trocar extension 2904 is inserted within the trocar receiving sleeve 2932 of the anvil portion 2930 until the engagement mechanisms 2938 of the trocar extension and the trocar receiving sleeve 2932 are engaged. In this manner, the anvil portion 2930 is mounted to the trocar extension 2904. The trocar extension 2904 is then retracted until the anvil portion 2930 is approximately adjacent to the clamping surface 2920 of the DLU portion 2902. In this position, tissue of the gastrointestinal tract is clamped between the anvil portion 2930 and the clamping surface 2920 of the DLU portion 2902. While the trocar extension 2904 is being retracted relative to the DLU portion 2902, the trocar receiving sleeve 2934 of the anvil 2930 is pulled through the opening in the tissue that was previously made by the trocar head 2905 of the DLU portion 2902.

As the trocar extension 2904 is further retracted relative to the DLU portion 2902, the first lens 2916 of the first image sensor portion 2908, is brought into closer proximity to the second lens 2942 of the second image sensor portion 2934. In this manner, light, e.g., an image, is conveyed from a distal end of the bore 2940 of the anvil portion 2930, through the second lens 2942, through the first lens 2916 and to the image sensor 2918. The image sensor 2918 of the image capture arrangement 2914 may then generate image data corresponding to the image and communicate the image data for further processing to a processor, e.g., the circuit arrangement 320 shown in FIG. 3(*b*) via a data transmission cable, e.g., the data bus 430 shown in FIG. 4(*b*).

As previously mentioned, the surgical device 2900 illustrated in FIGS. 28(*a*) to 28(*e*) provides an arrangement that enables a user to view the a surgical site without first removing the surgical device 2900 from the surgical site. For instance, in accordance with the above-described embodiment of the invention, a surgeon may perform an anastomosing procedure by clamping and stapling a section of tissue between the anvil portion 2930 and the DLU portion 2902 of the surgical device 2900. The surgeon may then view the integrity of the stapled section of tissue via the image sensor 2918, which is configured to provide an image of the surgical site through the bore 2940, without the need to remove the surgical device 2900 from the surgical site. Preferably, the surgical device 2900 illustrated in FIGS. 28(*a*) to 28(*e*) may enable a full view of the surgical site, e.g., the staple line, to be obtained by a user without requiring the DLU portion 2802 to be rotated within the surgical site.

In addition, the surgical device 2900 described hereinabove has the advantage of eliminating the step of rotationally aligning the anvil portion 2930 with the DLU portion 2902 because, by virtue of the centrally-disposed, "on-axis" arrangement, the image sensor 2918 of the trocar extension 2904 is automatically aligned with the bore 2940 in the anvil portion 2930. Furthermore, the surgical device 2900 described hereinabove has the advantage of eliminating the need for a sharp part, e.g., such as the sharp end 2942*a* of the tube 2940 shown in FIG. 27(*c*), since the trocar receiving sleeve 2934 of the anvil 2930 is pulled, during the retraction of the trocar extension 2904 relative to the DLU portion 2902, through an opening in the tissue that was previously made by the trocar head 2905 of the DLU portion 2902. The elimination of the sharp part reduces the likelihood of unintentionally puncturing a section of tissue during operation. In addition, the elimination of the need to puncture the section of tissue with a sharp part may reduce the likelihood that blood or other bodily fluids or tissue will obscure the image received by the image sensor 2918. Consequently the need for a cleaning system to clean the image sensors and/or lenses of blood or other bodily fluids or tissue that result from the puncturing of the section of tissue with a sharp part may also be eliminated, since the lens 2942 in the anvil portion 2930 may be manually cleaned by a user prior to being mounted to the DLU portion 2902.

While there is described above various embodiments of a circular stapler, it should be recognized that the present invention may be employed in any type of surgical device that is configured to be used in a surgical site. For instance, the present invention may be employed in any type of surgical device that has a first part, e.g., a DLU portion, that includes an image sensor, and a second part, e.g., an anvil portion, that is moveable relative to the first part and that includes an arrangement for conveying light, e.g., an image, to the image sensor. Advantageously, the arrangement of the surgical device enables an image to be received by the image sensor without removing the surgical device from the surgical site.

In various embodiments of the present invention, it may be advantageous that the imaging sensor(s) and the lighting source(s) be separately disposed. For instance, while it may be desirable that the imaging sensor(s) and the light source(s) be disposed together at various times, e.g., to ensure that sufficient light is provided to enable the imaging sensor(s) to operate correctly, in other embodiments it may be advantageous to integrate the light source with a different surgical component or attachment. In this manner, the light sources may be employed for various purposes other than provided sufficient light to enable operation of the imaging sensors.

Referring now to FIG. 29(*a*), there is illustrated a surgical system 3100, which may include components that are similar to the surgical system 100 illustrated in FIG. 1 and are not further discussed. The surgical system 3100 includes an electro-mechanical driver device 3110 detachably coupled via a flexible shaft 3170 to a surgical attachment 3120. The surgical attachment 3120 may include any type of surgical component configured to perform any type of surgical operation. For the purposes of example only, the surgical attachment 3120 is further described below as an aorta clamping attachment. It should be recognized that, in other embodiments, the surgical attachment 3120 may be merely a housing for the light sources and may not perform any other surgical function.

The surgical attachment 3120, according to this embodiment of the present invention, includes one or more light sources 3150. The light sources 3150 may be any device that is capable of providing illumination, e.g., a light emitting diode, a phosfluorescent source, fiber optics, etc. In one embodiment, the light sources 3150 may be integrally disposed within the surgical attachment 3120. Alternatively, the light sources 3120 may be permanently attached to, or may be temporarily attachable to, the surgical attachment 3120. The surgical attachment 3120 may also have a power source 3745, such as a small battery. The power source 3745 may be operable to provide electrical power to the one or more light sources 3120.

In addition, the surgical system 3100 may include an image capture arrangement 3715. The image capture arrangement 3715 may be a device, or part of a device, that is configured to be attachable to the flexible shaft 3170. In this manner, the image capture arrangement 3715 may constitute a second surgical attachment, such as the second surgical attachment 3700 illustrated in FIG. 29(b), and may be operated and/or controlled by the electromechanical driver device 3110. Alternatively, the image capture arrangement 3715 may be a device, or part of a device, that is not configured to be attachable to the flexible shaft 3170 but rather is operable and functions independently of the electro-mechanical driver device 3110. For example, the image capture arrangement 3715 may be an image pod, such as the image pod illustrated in, e.g., FIG. 4(a), or a surgical imaging device, such as the surgical imaging device illustrated in, e.g., FIG. 10. Alternatively, the image capture arrangement 3715 may have any other possible arrangement.

Figure 29A:
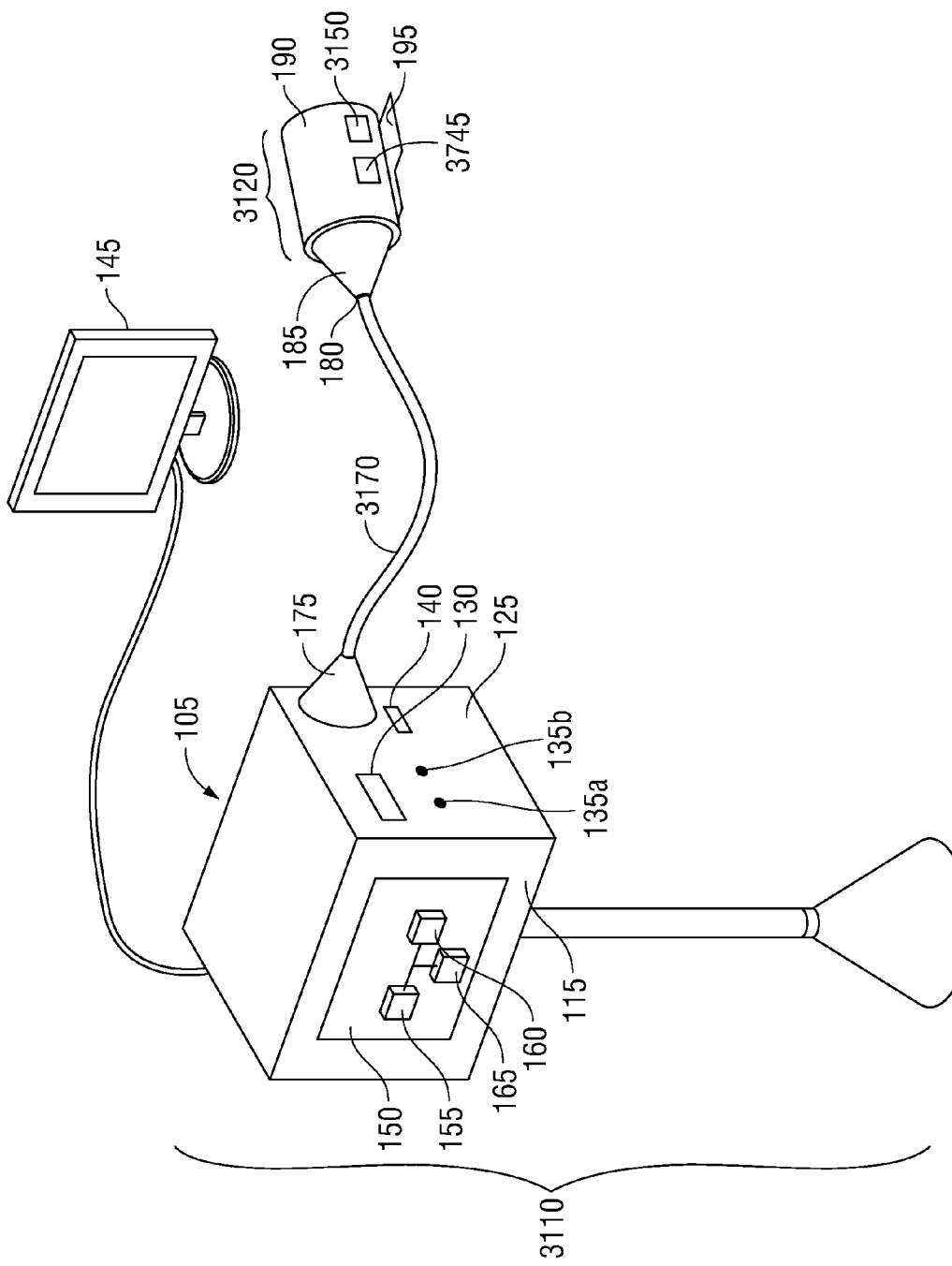
FIG. 29(*a*) is a perspective view of a surgical system, according to one embodiment of the present invention.
Figure 29B:
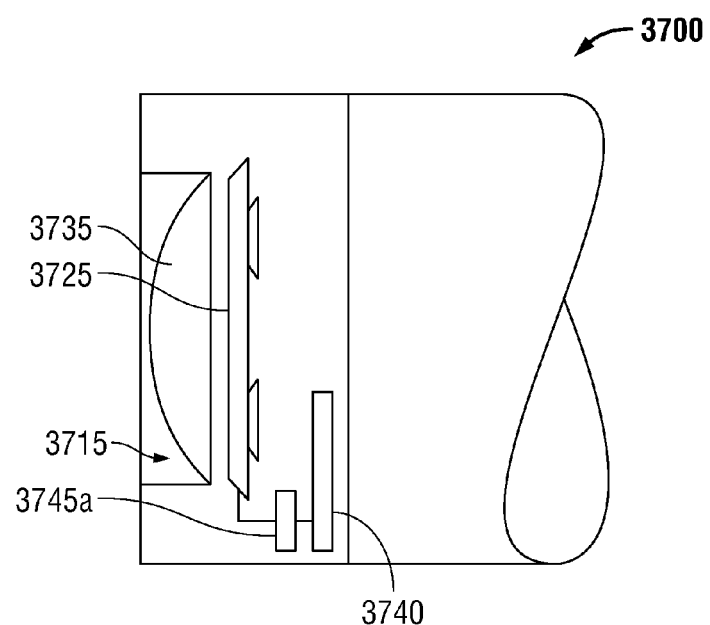

FIG. 29(b) illustrates one example embodiment of the image capture arrangement 3715. The image capture arrangement 3715 may include an optical system 3720 with a focusing lens 3735. In addition, the image capture arrangement 3715 may further include an imaging sensor, e.g., a light sensitive device such as a CCD 3725. When the image capture arrangement 3715 is directed toward an object to be imaged, the focusing lens 3735 focuses reflected light onto the CCD 3725. A wireless transmitter (or, e.g., a transceiver) 3740 may be situated in the image capture arrangement 3715 and may be communicatively coupled to the CCD 3725. An example of such a wireless transmitter is described in U.S. Pat. No. 5,604,531, expressly incorporated herein by reference in its entirely. Additionally, a power source 3745a, such as a small battery, is situated in the image capture arrangement 3715 and is operable to provide electrical power to the CCD 3725 and the wireless transmitter 3740. In operation, images captured by the CCD 3725 may be wirelessly transmitted via the wireless transmitter 3740 to a corresponding receiver (or transceiver) in a remote device, such as the electromechanical driver device 110.

Although, the present embodiment is described as using a CCD as an image sensor, other suitable image sensors may also be used, such as a CMOS type image sensor. The CMOS sensor may require less power than a CCD image sensor, due to its greater sensitivity to light. A CMOS image sensor may include, for example, a photo diode and/or a photo transistor to detect reflected light from an object to be imaged. The CMOS image sensor may transmit the image data as an analog signal or, alternatively, as a digital signal after processing by an analog-digital converter.

In operation, the surgical attachment 3120 may be inserted into a surgical site. The surgical attachment 3120, once located in the surgical site, may then be employed to perform the type of surgical operation for which it is configured. In the example embodiment described above, e.g., wherein the surgical attachment 3120 is an aorta clamping attachment, the surgical attachment 3120 may be inserted into a surgical site such that an aorta is positioned between its clamping surfaces. The surgical attachment 3120 may then be operated, for instance by and under the control of the electro-mechanical driver device 3110, to clamp the aorta. In one embodiment, the light sources 3150 are then activated so as to provide illumination within the surgical site. Of course, it should be recognized that the light sources 3150 may be activated prior to the surgical attachment 3120 being inserted into the surgical site.

In one embodiment, once the surgical attachment 3120 has been employed within the surgical site and the light sources 3150 have been activated, the surgical attachment 3120 may be detached from the flexible shaft 3170. The surgical attachment 3170 may then be left within the surgical site such that the light sources 3150 provide illumination within the surgical site, while the flexible shaft 3170 is removed from the surgical site. Thereafter, the image capture arrangement 3715 may be positioned within the surgical site so as to obtain image data corresponding to the surgical site. As set forth more fully above, in one embodiment, the image capture arrangement 3715 is attached to the flexible shaft 3170 and is operated and controlled by the electromechanical driver device 3110, while in other embodiments, the image capture arrangement 3715 is operated independently from the electro-mechanical driver device 3110.

Advantageously, the light sources 3120 provide sufficient light in the surgical site so as to enable the image capture arrangement 3715 to obtain adequate image data corresponding to the surgical site. For instance, the light sources 3120 may operate to provide sufficient light so that a user that views an image corresponding to the image data may determine whether or not the surgical attachment 3120 has been employed properly. In the embodiment described above, the light sources 3120 may operate to provide sufficient light so that a user that views an image corresponding to the image data may determine whether or not an aorta has been sufficiently clamped by the aorta clamp. Additionally or alternatively, the light sources 3150 may remain in the surgical site of the patient, and may be employed to continue providing illumination of the surgical site for any other function that is required to be performed by the operator, e.g., the insertion of a different surgical instrument, a physical inspection of the surgical site by the operator, etc.

While FIGS. 29(a) and 29(b) illustrate one example embodiment of a surgical system that includes imaging sensors and lighting source(s) that are separately disposed, it should be recognized that the present invention may also include various other configurations by which the imaging sensors and the lighting source(s) may be separately disposed or disposable.

Several embodiments of the present invention are specifically illustrated and/or described herein. However, it will be appreciated that modifications and variations of the present invention are covered by the above teachings without departing from the spirit and intended scope of the present invention.

What is claimed is:

1. A surgical imaging device, comprising:
   at least one light source for illuminating an object;
   at least two image sensors, each image sensor configured to generate image data corresponding to the object in the form of an image frame, each image frame partially overlapping with at least one other image frame, each of the image sensors corresponding to a different point of view with respect to the object; and a video processor configured to receive simultaneously from each image sensor the image data corresponding to the image frames and to process the image data by combining the image frames to generate a composite image from the combined image frames, each image frame corresponding to a subportion of the composite image, wherein the at least two image sensors are positioned opposite from one another such that the composite image is generated therebetween and each opposing image sensor is angled towards its respective point of view to generate the composite image between the at least two opposing image sensors.

2. The device of claim 1, wherein the surgical imaging device is configured to be inserted into a body of a patient.

3. The device of claim 2, wherein the video processor stitches the image data received from each image sensor by processing a portion of image data received from one image sensor that overlaps with a portion of image data received from another image sensor.

4. The device of claim 1, wherein the surgical imaging device is configured to be inserted into an abdominal cavity of a patient.

5. The device of claim 1, wherein the composite image corresponds to an entire abdominal cavity of a patient.

6. The device of claim 1, wherein the video processor is configured to normalize the image data received from each image sensor.

7. The device of claim 1, wherein the video processor is configured to orient the image data received from each image sensor.

8. The device of claim 1, wherein the video processor is configured to stitch the image data received from each image sensor so as to generate the composite image.

9. The device of claim 1, wherein the video processor is configured to one of establish or adjust orientation data points of the composite image.

10. The device of claim 9, wherein the video processor one of establishes or adjusts orientation data points of the composite image by a control device that moves one or more of the image sensors.

11. The device of claim 1, wherein the video processor is configured to selectively generate a region of interest corresponding to a portion of the composite image.

12. The device of claim 11, wherein the video processor selectively generates the region of interest corresponding to a portion of the composite image in accordance with signals received from a control device.

13. The device of claim 11, wherein the video processor is configured to automatically adjust the region of interest.

14. The device of claim 13, wherein the video processor automatically adjusts the region of interest so as to continuously display a surgical instrument as the surgical instrument is moved.

15. The device of claim 1, wherein the video processor is configured to selectively generate a region of interest corresponding to signals received from a user input device to zoom into or out of a portion of the composite image.

16. The device of claim 1, further comprising a display device coupled to the video processor, the video processor configured to generates a display image for display on the display device.

17. The device of claim 16, wherein the display device is a wireless personal display monitor.

18. The device of claim 16, wherein the display device is an overhead display monitor.

19. The device of claim 1, wherein the composite image has an aspect ratio of 16:9.

20. The device of claim 1, wherein the composite image has an aspect ratio of 4:3.

21. A method for generating an image comprising the steps of:

illuminating an object in a surgical site;

simultaneously generating, via at least two image sensors, at least two sets of image data corresponding to the object, each of the image sensors corresponding to a different point of view, each set of image data partially overlapping at least one other set of image data, wherein the at least two image sensors are positioned opposite from one another such that the composite image is generated therebetween and each opposing image sensor is angled towards its respective point of view to generate the composite image between the at least two opposing image sensors; and combining the at least two sets of image data so as to generate a composite image from the combined image data, each set of image data corresponding to a subportion of the composite image.

22. The method of claim 21, further comprising the step of generating the image inside a body of a patient.

23. The method of claim 21, further comprising the step of inserting the surgical imaging device into an abdominal cavity of a patient.

24. The method of claim 23, wherein the processing step includes generating the composite image of an entire abdominal cavity of a patient.

25. The method of claim 21, further comprising the step of normalizing the image data received from each image sensor.

26. The method of claim 21, further comprising the step of orienting the image data received from each image sensor.

27. The method of claim 21, further comprising the step of stitching the image data received from each image sensor so as to generate the composite image.

28. The method of claim 27, wherein the stitching includes processing a portion of image data received from one image sensor that overlaps with a portion of image data received from another image sensor.

29. The method of claim 21, further comprising the step of establishing or adjusting orientation data points of the composite image.

30. The method of claim 29, wherein the step of establishing or adjusting the orientation data points of the composite image is performed by a control device that moves one or more of the image sensors.

31. The method of claim 21, further comprising the step of selectively generating a region of interest corresponding to a portion of the composite image.

32. The method of claim 31, wherein the step of selectively generating the region of interest corresponding to a portion of the composite image includes processing signals received from a control device.

33. The method of claim 31, further comprising the step of automatically adjusting the region of interest.

34. The method of claim 33, wherein the step of automatically adjusting the region of interest includes continuously displaying a surgical instrument as the surgical instrument is moved.

35. The method of claim 31, wherein the step of selectively generating a region of interest includes processing signals received from a user input device to zoom into or out of a portion of the composite image.

36. The method of claim 21, further comprising the steps of:
   generating a display image; and
   display the display image on the display device.

37. The method of claim 36, wherein the displaying step includes displaying the display image on a wireless personal display monitor.

38. The method of claim 36, wherein the displaying step includes displaying the display image on an overhead display monitor.

39. The method of claim 21, wherein the processing step includes generating the composite image so as to have an aspect ratio of 16:9.

40. The method of claim 21, wherein the processing step includes generating the composite image so as to have an aspect ratio of 4:3.

* * * * *